United States Patent [19]

Mosley et al.

[11] Patent Number: 5,767,065
[45] Date of Patent: Jun. 16, 1998

[54] USE OF INTERLEUKIN-4 RECEPTORS TO INHIBIT BIOLOGICAL RESPONSES MEDIATED BY INTERLEUKIN-4

[75] Inventors: Bruce Mosley; David J. Cosman; Linda Park, all of Seattle; M. Patricia Beckmann, Poulsbo; Carl J. March; Rejean Idzerda, both of Seattle, all of Wash.

[73] Assignee: Immunex Corporation, Seattle, Wash.

[21] Appl. No.: 466,324

[22] Filed: Jun. 6, 1995

Related U.S. Application Data

[62] Division of Ser. No. 94,669, Jul. 20, 1993, Pat. No. 5,599,905, which is a division of Ser. No. 480,694, Feb. 14, 1990, which is a continuation-in-part of Ser. No. 370,924, Jun. 23, 1989, abandoned, which is a continuation-in-part of Ser. No. 326,156, Mar. 20, 1989, abandoned, which is a continuation-in-part of Ser. No. 319,438, Mar. 2, 1989, abandoned, which is a continuation-in-part of Ser. No. 265,047, Oct. 31, 1988, abandoned.

[51] Int. Cl.$^6$ .................................................. A61K 38/04
[52] U.S. Cl. ................. 514/2; 514/8; 514/12; 514/826; 514/885; 514/886; 424/85.1
[58] Field of Search ................. 514/2, 8, 12; 424/85.1

[56] References Cited

U.S. PATENT DOCUMENTS

| | | | |
|---|---|---|---|
| 4,551,433 | 11/1985 | DeBoer | 435/253 |
| 4,675,285 | 6/1987 | Clark et al. | 435/6 |
| 4,683,199 | 7/1987 | Palladino | 435/68 |
| 5,246,701 | 9/1993 | Dugas et al. | |
| 5,449,756 | 9/1995 | Taniguchi et al. | 530/350 |

FOREIGN PATENT DOCUMENTS

| | | |
|---|---|---|
| A-44950/30 | 3/1994 | Australia . |
| 0 327 283 B1 | 9/1989 | European Pat. Off. . |
| WO 87/02990 | 5/1987 | WIPO . |
| WO 89/09621 | 10/1989 | WIPO . |
| WO 91/03555 | 3/1991 | WIPO . |
| WO 93/11234 | 6/1993 | WIPO . |
| WO 94/21282 | 9/1994 | WIPO . |

OTHER PUBLICATIONS

Ohara and Paul, "Receptors for B-cell stimulatory factor-1 expressed on cells of haematopietic lineage", *Nature* 325:537–540, 1987.

Park et al., "Characterization of the high-affinity cell-surface receptor for murine B-cell-stimulating factor 1", *Proc. Nat. Acad. Sci. USA,* 84:1669–1673, 1987.

Park et al., "Characterization of the Human B Cell Stimulatory Factor 1 Receptor", *J. Exp. Med.,* 166:476–488, 1987.

Nakajima et al., "Detection of Receptors for Murine B Cell Stimulatory Factor 1 (BSF1): Presence of Functional Receptors on CBA/N Splenic B Cells", *J. Immunol.* 139:774–779, 1987.

Cabrillat et al., "High Affinity Binding of Human Interleukin 4 to Cell Lines", *Biochem. & Biophys. Res. Commun.* 149:995–1001, 1987.

Lowenthal et al., "Expression of High Affinity Receptors for Murin Interleukin 4 (BSF1)", *J. Immunol.* 140:456–464, 1988.

Lowenthal et al., "Up-Regulation of Interleukin 4 Receptor Expression on Immature (Lyt-2$^-$/L3T4$^-$) Thymocytes", *J. Immunol.* 140:474–478, 1988.

Park et al., "Interleukin-4 Binds to Murine Fibroblasts: Receptor Characterization and Induction of Colony Stimulating Activity Production", *UCLA Symposia Abstracts, J. Cell Biochem. Suppl. 12A,* 1988.

Dower et al., "Interleukin Receptors", *ISI Atlas of Science: Immunology,* 116–120, 1988.

Okayama and Berg, "High-Efficiency Cloning of Full-Length cDNA", *Mol. Cell. Biol.* 2:161–170, 1983.

Okayama and Berg, "A cDNA Cloning Vector that Permits Expression of cDNA Inserts in Mammalian Cells", *Mol. Cell. Biol.* 3:280–289, 1983.

Aruffo and Seed, "Molecular cloning of a CD28 cDNA by a high-efficiency COS cell expression system", *Proc. Natl. Acad. Sci. USA* 84:8573–8577, 1987.

Yamasaki et al., "Cloning and Expression of the Human Interleukin-6 (BSF-2/IFNβ 2) Receptor", *Science* 241:825–828, 1988.

Sims et al., "cDNA Expression Cloning of the IL-1 Receptor, a Member of the Immunoglobulin Superfamily", *Science* 241:585–589, 1988.

De Maagd et al., "The human thymus microenvironment: heterogeneity detected by monoclonal anti-epithelial cell antibodies", *Immunology* 54:745–754, 1985.

Larche et al., "A novel T-lymphocyte molecule that may function in the induction of self-tolerance and MHC-restriction within the human thymic microenvironment", *Immunology* 64:101–105, 1988.

Larche et al., "Functional evidence for a monoclonal antibody that binds to the human IL-4 receptor", *Immunology* 65:617–622, 1988.

Jabaari et al., *British J. Cancer* 59 (6) 910–914, 1989.

Salari et al., *Biochem. J.* 262:897–908, 1989.

Urdal et al., "Studies on Hematopoietic Growth Factor Receptors Using Human Recombinant IL-3, GM-CSF, G-CSF, M-CSF, IL-1 and IL-4", *Behring Inst. Mitt.* 83:27–39, Aug., 1988.

Harada et al., "Expression cloning of a cDNA encoding the murine interleukin 4 receptor based on ligand binding", *Proc. Natl. Acad. Sci. USA* 87:857–861, 1990.

Mosley et al., "The Murine Interleukin-4 Receptor: Molecular Cloning and Characterization of Secreted and Membrane Bound Forms", *Cell* 59:335–348, Oct., 1989.

(List continued on next page.)

*Primary Examiner*—Garnette D. Draper
*Attorney, Agent, or Firm*—Kathryn A. Anderson; Christopher L. Wight

[57] ABSTRACT

Mammalian Interleukin-4 receptor proteins find use in inhibiting biological activities of IL-4. A method for suppressing an IL-4-dependent immune or inflammatory response in a mammal, including a human, by administering an effective amount of soluble IL-4 receptor (sIL-4R) and a suitable diluent or carrier.

21 Claims, 21 Drawing Sheets

OTHER PUBLICATIONS

Finkelman et al., "IL–4 Is Required to Generate and Sustain In Vivo IgE Responses", *J. Immunol.* 141:2335–2341, 1988.

Finkelman et al., "Suppression of in vivo polyclonal IgE responses by monoclonal antibody to the lymphokine B–cell stimulatory factor 1", *Proc. Natl. Acad. Sci. USA* 83:9675–9678, 1986.

Snapper et al., "Differential Regulation IgG1 and IgE Synthesis by Interleukin 4", *J. Exp. Med.* 167:183–196, 1988.

Finkelman et al., "T Help Requirements for the Generation of an In Vivo IgE Response: A Late Acting Form of T Cell Help Other Than IL–4 Is Required for IgE but not for IgG1 Production", *J. Immunol.* 142:403–408, 1989.

Galizzi et al., "Purification of a 130–kDa T Cell Glycoprotein That Binds Human Interleukin 4 with High Affinity", *J. Biol. Chem.* 265:439–444, 1990.

Galizzi et al., "Internalization of Human Interleukin 4 and Transient Down–regulation of Its Receptor in the C23–inducible Jijoye Cells", *J. Biol. Chem.* 264:6984–6989, 1989.

Chester and Hawkins, "Clinical issues in antibody design", *Tibtech* 13:294–300, 1995.

Paul, William E., Ed., *Fundamental Immunology*, Raven Press, New York, 1993, p. 826.

Borish et al., "Phase I Nebulization Study of Recombinant Human IL–4 Receptor (rhuIL–4R) in Adult Patients with Mild Atopic Asthma", Abstract for American Academy of Allergy, Asthma and Immunology/AAI/CIS Joint Meeting Feb. 21–26, 1997; published in *J. Allergy Clin Immunol* 99: S413, Abstract 1678, Jan. 1997.

Borish et al., "Phase I Neubulization Study of Recombinant Human IL–4 Receptor (rhuIL–4R) in Adult Patients with Mild Atopic Asthma", Poster presented at American Academy of Allergy, Asthma and Immunology/AAI/CIS Joint Meeting Feb. 21–26, 1997.

Knight, "Allergy: Big Market, Big Risks", *Bio/Technology* 8:717–719, Aug. 1990.

Renz et al., "Inhibition of Allergen–Induced IgE and IgG1 Production by Soluble IL–4 Receptor",*Int Arch Allergy Immunol* 106: 46–54, 1995.

Renz et al., "Inhibition of Allergen–Induced and Allergen–Specific IgE and IgG1 Production by Soluble IL–4 Receptor", *J. Allergy Clin Immunol:*, p. 234, Abstract 373, Jan. 1993.

Mowat et al., "A role for IL–4 in immunology mediated enteropathy", *Clin Exp Immunol* 99: 65–69, 1995.

Finkelman et al., "Regulation of murine in vivo IgG and IgE responses by a monoclonal anti–IL–4 receptor antibody", *International Immunology* 3: 599–607, Jun. 1991.

Finkelman et al., "Lymphokine Control of In Vivo Immunoglobulin Isotype Selection", *Annu. Rev. Immunol.* 8: 303–33, 1990.

Ryan, "Interleukin–4 and its receptor: Essential mediators of the allergic response", *J. Allergy Clin Immunol* 99: 1–5, 1997.

Renz et al., "Enhanced IL–4 Production and IL–4 Receptor Expression in Atopic Dermatitis and Their Modulation by Interferon–Gamma", *The Journal of Investigative Dermatology* 99: 403–408, Oct. 1992.

Jujo et al., "Decreased interferon gamma and increased interleukin–4 production in atopic dermatitis promotes IgE synthesis", *J. Allergy Clin Immunol 90*: 323–331, Sep. 1992.

Jacobs et al., "Characterization and Pharmacokinetic Parameters of Recombinant Soluble Interleukin–4 Receptor", *Blood* 77: 2396–2403, Jun. 1991.

Maliszewski et al., "Recombinant Soluble Receptors Specifically Inhibit IL–1 and IL–4 Induced B Cell Activities In Vitro", *The Journal of Immunology 144*: 3028–3033, Apr. 1990.

Spiegelberg et al., "Role of Interleukin–4 in Human Immunoglobulin E Formation in hu–PBL–SCID Mice", *Journal of Clinical Invest.* 93: 711–717, Feb. 1994.

Garrone et al., "A recombinant extracellular domain of the human interleukin 4 receptor inhibits the biological effects of interleukin 4 on T and B lymphocytes", *Eur. J. Immunol.* 21: 1365–1369, 1991.

Fanslow et al., "Regulation of Alloreactivity in Vivo by IL–4 and the Soluble IL–4 Receptor", *Journal of Immunology* 147: 535–540, Jul. 1991.

Maliszewski et al., "The Interleukin–4 Receptor: Potential Therapeutic Applications in the Allergic Response", *Allergy & Clinical Immunology News* 2: 86–90, May/Jun. 1990.

Müller et al., "Th2 Cells Mediate IL–4–Dependent Local Tissue Inflammation", *The Journal of Immunology 150*: 5576–5584, Jun. 1993.

Sato et al., "Recombinant Soluble Murine IL–4 Receptor Can Inhibit or Enhance IgE Responses in Vivo", *The Journal of Immunology 150*: 2717–2723, Apr. 1993.

Weber et al., "Soluble IL–4 Receptor (sIL–4R) Modulates the Effects of IL–4 on HIV–1 Replication in Human Monocytes", Abstract of poster presented at International Cytokine Society Meeting, Banff, Alberta, Canada, Oct. 1–5, 1994.

Bergese, et al., "Regulation of Endothelial VCAM–1 Expression in Murine Cardiac Grafts", *American Journal of Pathology 147*: 166–175, Jul. 1995.

FIGURE 2A

| | | | | | | | | | | | | | | |
|---|---|---|---|---|---|---|---|---|---|---|---|---|---|---|
| ATG | GGG | CGG | CTT | TGC | ACC | AAG | TTC | CTG | ACC | TCT | GTG | GGC | TGT | CTG | -31 |
| Met | Gly | Arg | Leu | Cys | Thr | Lys | Phe | Leu | Thr | Ser | Val | Gly | Cys | Leu | -11 |

```
ATG GGG CGG CTT TGC ACC AAG TTC CTG ACC TCT GTG GGC TGT CTG    -31
Met Gly Arg Leu Cys Thr Lys Phe Leu Thr Ser Val Gly Cys Leu    -11

ATT TTG CTG TTG GTG ACT GGA TCT GGG AGC ATC AAG GTC CTG GGT     15
Ile Leu Leu Leu Val Thr Gly Ser Gly Ser Ile Lys Val Leu Gly      5

GAG CCC ACC TGC TTC TCT GAC TAC ATC CGC ACT TCC ACG TGT GAG     60
Glu Pro Thr Cys Phe Ser Asp Tyr Ile Arg Thr Ser Thr Cys Glu     20

TGG TTC CTG GAT AGC GCT GTG GAC TGC AGT TCT CAG CTC TGC CTA    105
Trp Phe Leu Asp Ser Ala Val Asp Cys Ser Ser Gln Leu Cys Leu     35

CAC TAC AGG CTG ATG TTC TTC GAG TTC TCT GAA AAC CTC ACA TGC    150
His Tyr Arg Leu Met Phe Phe Glu Phe Ser Glu Asn Leu Thr Cys     50

ATC CCG AGG AAC AGT GCC AGC ACT GTG TGT GTG TGC CAC ATG GAA    195
Ile Pro Arg Asn Ser Ala Ser Thr Val Cys Val Cys His Met Glu     65

ATG AAT AGG CCG GTC CAA TCA GAC AGA TAC CAG ATG GAA CTG TGG    240
Met Asn Arg Pro Val Gln Ser Asp Arg Tyr Gln Met Glu Leu Trp     80

GCT GAG CAC AGA CAG CTG TGG CAG GGC TCC TTC AGC CCA AGT GGT    285
Ala Glu His Arg Gln Leu Trp Gln Gly Ser Phe Ser Pro Ser Gly     95

AAT GTG AAG CCC CTA GCT CCA GAC AAC CTC ACA CTC CAC ACC AAT    330
Asn Val Lys Pro Leu Ala Pro Asp Asn Leu Thr Leu His Thr Asn    110

GTG TCC GAC GAA TGG CTG CTG ACC TGG AAT AAC CTG TAC CCA TCG    375
Val Ser Asp Glu Trp Leu Leu Thr Trp Asn Asn Leu Tyr Pro Ser    125

AAC AAC TTA CTG TAC AAA GAC CTC ATC TCC ATG GTC AAC ATC TCC    420
Asn Asn Leu Leu Tyr Lys Asp Leu Ile Ser Met Val Asn Ile Ser    140

AGA GAG GAC AAC CCT GCA GAA TTC ATA GTC TAT AAT GTG ACC TAC    465
Arg Glu Asp Asn Pro Ala Glu Phe Ile Val Tyr Asn Val Thr Tyr    155

AAG GAA CCC AGG CTG AGC TTC CCG ATC AAC ATC CTG ATG TCA GGG    510
Lys Glu Pro Arg Leu Ser Phe Pro Ile Asn Ile Leu Met Ser Gly    170

GTC TAC TAT ACG GCG CGT GTG AGG GTC AGA TCC CAG ATA CTC ACT    555
Val Tyr Tyr Thr Ala Arg Val Arg Val Arg Ser Gln Ile Leu Thr    185

GGC ACC TGG AGT GAG TGG AGT CCT AGC ATC ACG TGG TAC AAC CAC    600
Gly Thr Trp Ser Glu Trp Ser Pro Ser Ile Thr Trp Tyr Asn His    200

TTC CAG CTG CCC CTG ATA CAG CGC CTT CCA CTG GGG GTC ACC ATC    645
Phe Gln Leu Pro Leu Ile Gln Arg Leu Pro Leu Gly Val Thr Ile    215

TCC TGC CTC TGC ATC CCG TTG TTT TGC CTG TTC TGT TAC TTC AGC    690
Ser Cys Leu Cys Ile Pro Leu Phe Cys Leu Phe Cys Tyr Phe Ser    230

ATT ACC AAG ATT AAG AAG ATA TGG TGG GAC CAG ATT CCC ACC CCA    735
Ile Thr Lys Ile Lys Lys Ile Trp Trp Asp Gln Ile Pro Thr Pro    245
```

FIGURE 2B

| | | | | | | | | | | | | | |
|---|---|---|---|---|---|---|---|---|---|---|---|---|---|
| GCA | CGC | AGT | CCC | TTG | GTG | GCC | ATC | ATC | ATT | CAG | GAT | GCA | CAG GTG | 780 |
| Ala | Arg | Ser | Pro | Leu | Val | Ala | Ile | Ile | Ile | Gln | Asp | Ala | Gln Val | 260 |

```
GCA CGC AGT CCC TTG GTG GCC ATC ATC ATT CAG GAT GCA CAG GTG     780
Ala Arg Ser Pro Leu Val Ala Ile Ile Ile Gln Asp Ala Gln Val     260

CCC CTC TGG GAT AAG CAG ACC CGA AGC CAG GAG TCA ACC AAG TAC     825
Pro Leu Trp Asp Lys Gln Thr Arg Ser Gln Glu Ser Thr Lys Tyr     275

CCG CAC TGG AAA ACT TGT CTA GAC AAG CTG CTG CCT TGC TTG CTG     870
Pro His Trp Lys Thr Cys Leu Asp Lys Leu Leu Pro Cys Leu Leu     290

AAG CAC AGA GTA AAG AAG AAG ACA GAC TTC CCG AAG GCT GCC CCA     915
Lys His Arg Val Lys Lys Lys Thr Asp Phe Pro Lys Ala Ala Pro     305

ACC AAG TCT CTC CAG AGT CCT GGA AAG GCA GGC TGG TGT CCC ATG     960
Thr Lys Ser Leu Gln Ser Pro Gly Lys Ala Gly Trp Cys Pro Met     320

GAG GTC AGC AGG ACC GTC CTC TGG CCA GAG AAT GTT AGT GTC AGT    1005
Glu Val Ser Arg Thr Val Leu Trp Pro Glu Asn Val Ser Val Ser     335

GTG GTG CGC TGT ATG GAG CTG TTT GAG GCC CCA GTA CAG AAT GTG    1050
Val Val Arg Cys Met Glu Leu Phe Glu Ala Pro Val Gln Asn Val     350

GAG GAG GAA GAA GAT GAG ATA GTC AAA GAG GAC CTG AGC ATG TCA    1095
Glu Glu Glu Glu Asp Glu Ile Val Lys Glu Asp Leu Ser Met Ser     365

CCT GAG AAC AGC GGA GGC TGC GGC TTC CAG GAG aGC CAG GCA GAC    1140
Pro Glu Asn Ser Gly Gly Cys Gly Phe Gln Glu Ser Gln Ala Asp     380

ATC ATG GCT CGG CTC ACT GAG AAC CTG TTT TCC GAC TTG TTG GAG    1185
Ile Met Ala Arg Leu Thr Glu Asn Leu Phe Ser Asp Leu Leu Glu     395

GCT GAG AAT GGG GGC CTT GGC CAG TCA GCC TTG GCA GAG TCA TGC    1230
Ala Glu Asn Gly Gly Leu Gly Gln Ser Ala Leu Ala Glu Ser Cys     410

TCC CCT CTG CCT TCA GGA AGT GGG CAG GCT TCT GTA TCC TGG GCC    1275
Ser Pro Leu Pro Ser Gly Ser Gly Gln Ala Ser Val Ser Trp Ala     425

TGC CTC CCC ATG GGG CCC AGT GAG GAG GCC ACA TGC CAG GTC ACA    1320
Cys Leu Pro Met Gly Pro Ser Glu Glu Ala Thr Cys Gln Val Thr     440

GAG CAG CCT TCA CAC CCA GGC CCT CTT TCA GGC AGC CCA GCC CAG    1365
Glu Gln Pro Ser His Pro Gly Pro Leu Ser Gly Ser Pro Ala Gln     455

AGT GCA CCT ACT CTG GCT TGC ACG CAG GTC CCA CTT GTC CTT GCA    1410
Ser Ala Pro Thr Leu Ala Cys Thr Gln Val Pro Leu Val Leu Ala     470

GAC AAT CCT GCC TAC CGG AGT TTT AGT GAC TGC TGT AGC CCG GCC    1455
Asp Asn Pro Ala Tyr Arg Ser Phe Ser Asp Cys Cys Ser Pro Ala     485

CCA AAT CCT GGA GAG CTG GCT CCA GAG CAG CAG CAG GCT GAT CAT    1500
Pro Asn Pro Gly Glu Leu Ala Pro Glu Gln Gln Gln Ala Asp His     500

CTG GAA GAA GAG GAG CCT CCA AGC CCG GCT GAC CCC CAT TCT TCA    1545
Leu Glu Glu Glu Glu Pro Pro Ser Pro Ala Asp Pro His Ser Ser     515
```

FIGURE 2C

```
GGG CCA CCA ATG CAG CCA GTG GAG AGC TGG GAG CAG ATC CTT CAC   1590
Gly Pro Pro Met Gln Pro Val Glu Ser Trp Glu Gln Ile Leu His    530

ATG AGT GTC CTG CAG CAT GGG GCA GCT GCT GGC TCC ACC CCA GCC   1635
Met Ser Val Leu Gln His Gly Ala Ala Ala Gly Ser Thr Pro Ala    545

CCT GCC GGT GGC TAC CAG GAG TTT GTG CAG GCA GTG AAG CAG GGT   1680
Pro Ala Gly Gly Tyr Gln Glu Phe Val Gln Ala Val Lys Gln Gly    560

GCC GCC CAG GAT CCT GGG GTG CCT GGT GTC AGG CCT TCT GGA GAC   1725
Ala Ala Gln Asp Pro Gly Val Pro Gly Val Arg Pro Ser Gly Asp    575

CCC GGT TAC AAG GCC TTC TCG AGC CTG CTC AGC AGC AAT GGC ATC   1770
Pro Gly Tyr Lys Ala Phe Ser Ser Leu Leu Ser Ser Asn Gly Ile    590

CGC GGG GAC ACA GCA GCA GCG GGG ACT GAC GAT GGG CAT GGA GGC   1815
Arg Gly Asp Thr Ala Ala Ala Gly Thr Asp Asp Gly His Gly Gly    605

TAC AAG CCC TTC CAG AAT CCT GTT CCT AAC CAG TCC CCT AGC TCC   1860
Tyr Lys Pro Phe Gln Asn Pro Val Pro Asn Gln Ser Pro Ser Ser    620

GTG CCC TTA TTT ACT TTC GGA CTA GAC ACG GAG CTG TCA CCC AGT   1905
Val Pro Leu Phe Thr Phe Gly Leu Asp Thr Glu Leu Ser Pro Ser    635

CCT CTG AAC TCA GAC CCA CCC AAA AGC CCC CCA GAA TGC CTT GGT   1950
Pro Leu Asn Ser Asp Pro Pro Lys Ser Pro Pro Glu Cys Leu Gly    650

CTG GAG CTG GGG CTC AAA GGA GGT GAC TGG GTG AAG GCC CCT CCT   1995
Leu Glu Leu Gly Leu Lys Gly Gly Asp Trp Val Lys Ala Pro Pro    665

CCT GCA GAT GAG GTG CCC AAG CCC TTT GGG GAT GAC CTG GGC TTT   2040
Pro Ala Asp Glu Val Pro Lys Pro Phe Gly Asp Asp Leu Gly Phe    680

GGT ATT GTG TAC TCG TCC CTC ACT TGC CAC TTG TGT GGC CAC CTG   2085
Gly Ile Val Tyr Ser Ser Leu Thr Cys His Leu Cys Gly His Leu    695

AAG CAA CAC CAC AGC CAG GAG GAA GGT GGC CAG AGC CCC ATC GTT   2130
Lys Gln His His Ser Gln Glu Glu Gly Gly Gln Ser Pro Ile Val    710

GCT AGC CCT GGC TGT GGC TGC TGC TAC GAT GAC AGA TCA CCA TCC   2175
Ala Ser Pro Gly Cys Gly Cys Cys Tyr Asp Asp Arg Ser Pro Ser    725

CTG GGG AGC CTC TCG GGG GCC TTG GAA AGC TGT CCT GAG GGA ATA   2220
Leu Gly Ser Leu Ser Gly Ala Leu Glu Ser Cys Pro Glu Gly Ile    740

CCA CCA GAA GCC AAC CTC ATG TCA GCA CCC AAG ACA CCC TCA AAC   2265
Pro Pro Glu Ala Asn Leu Met Ser Ala Pro Lys Thr Pro Ser Asn    755

TTG TCA GGG GAG GGC AAG GGC CCT GGT CAC TCT CCT GTT CCC AGC   2310
Leu Ser Gly Glu Gly Lys Gly Pro Gly His Ser Pro Val Pro Ser    770

CAG ACG ACC GAG GTG CCT GTG GGC GCC CTG GGC ATT GCT GTT TCT   2355
Gln Thr Thr Glu Val Pro Val Gly Ala Leu Gly Ile Ala Val Ser    785
```

FIGURE 4A

| | | | | | | | | | | | | | |
|---|---|---|---|---|---|---|---|---|---|---|---|---|---|
| ATG | GGG | TGG | CTT | TGC | TCT | GGG | CTC | CTG | TTC | CCT | GTG | AGC | TGC | CTG | -31 |
| Met | Gly | Trp | Leu | Cys | Ser | Gly | Leu | Leu | Phe | Pro | Val | Ser | Cys | Leu | -11 |

| GTC | CTG | CTG | CAG | GTG | GCA | AGC | TCT | GGG | AAC | ATG | AAG | GTC | TTG | CAG | 15 |
| Val | Leu | Leu | Gln | Val | Ala | Ser | Ser | Gly | Asn | <u>Met</u> | Lys | Val | Leu | Gln | 5 |

| GAG | CCC | ACC | TGC | GTC | TCC | GAC | TAC | ATG | AGC | ATC | TCT | ACT | TGC | GAG | 60 |
| Glu | Pro | Thr | Cys | Val | Ser | Asp | Tyr | Met | Ser | Ile | Ser | Thr | Cys | Glu | 20 |

| TGG | AAG | ATG | AAT | GGT | CCC | ACC | AAT | TGC | AGC | ACC | GAG | CTC | CGC | CTG | 105 |
| Trp | Lys | Met | Asn | Gly | Pro | Thr | Asn | Cys | Ser | Thr | Glu | Leu | Arg | Leu | 35 |

| TTG | TAC | CAG | CTG | GTT | TTT | CTG | CTC | TCC | GAA | GCC | CAC | ACG | TGT | ATC | 150 |
| Leu | Tyr | Gln | Leu | Val | Phe | Leu | Leu | Ser | Glu | Ala | His | Thr | Cys | Ile | 50 |

| CCT | GAG | AAC | AAC | GGA | GGC | GCG | GGG | TGC | GTG | TGC | CAC | CTG | CTC | ATG | 195 |
| Pro | Glu | Asn | Asn | Gly | Gly | Ala | Gly | Cys | Val | Cys | His | Leu | Leu | Met | 65 |

| GAT | GAC | GTG | GTC | AGT | GCG | GAT | AAC | TAT | ACA | CTG | GAC | CTG | TGG | GCT | 240 |
| Asp | Asp | Val | Val | Ser | Ala | Asp | Asn | Tyr | Thr | Leu | Asp | Leu | Trp | Ala | 80 |

| GGG | CAG | CAG | CTG | CTG | TGG | AAG | GGC | TCC | TTC | AAG | CCC | AGC | GAG | CAT | 285 |
| Gly | Gln | Gln | Leu | Leu | Trp | Lys | Gly | Ser | Phe | Lys | Pro | Ser | Glu | His | 95 |

| GTG | AAA | CCC | AGG | GCC | CCA | GGA | AAC | CTG | ACA | GTT | CAC | ACC | AAT | GTC | 330 |
| Val | Lys | Pro | Arg | Ala | Pro | Gly | Asn | Leu | Thr | Val | His | Thr | Asn | Val | 110 |

| TCC | GAC | ACT | CTG | CTG | CTG | ACC | TGG | AGC | AAC | CCG | TAT | CCC | CCT | GAC | 375 |
| Ser | Asp | Thr | Leu | Leu | Leu | Thr | Trp | Ser | Asn | Pro | Tyr | Pro | Pro | Asp | 125 |

| AAT | TAC | CTG | TAT | AAT | CAT | CTC | ACC | TAT | GCA | GTC | AAC | ATT | TGG | AGT | 420 |
| Asn | Tyr | Leu | Tyr | Asn | His | Leu | Thr | Tyr | Ala | Val | Asn | Ile | Trp | Ser | 140 |

| GAA | AAC | GAC | CCG | GCA | GAT | TTC | AGA | ATC | TAT | AAC | GTG | ACC | TAC | CTA | 465 |
| Glu | Asn | Asp | Pro | Ala | Asp | Phe | Arg | Ile | Tyr | Asn | Val | Thr | Tyr | Leu | 155 |

| GAA | CCC | TCC | CTC | CGC | ATC | GCA | GCC | AGC | ACC | CTG | AAG | TCT | GGG | ATT | 510 |
| Glu | Pro | Ser | Leu | Arg | Ile | Ala | Ala | Ser | Thr | Leu | Lys | Ser | Gly | Ile | 170 |

| TCC | TAC | AGG | GCA | CGG | GTG | AGG | GCC | TGG | GCT | CAG | TGC | TAT | AAC | ACC | 555 |
| Ser | Tyr | Arg | Ala | Arg | Val | Arg | Ala | Trp | Ala | Gln | Cys | Tyr | Asn | Thr | 185 |

| ACC | TGG | AGT | GAG | TGG | AGC | CCC | AGC | ACC | AAG | TGG | CAC | AAC | TCC | TAC | 600 |
| Thr | Trp | Ser | Glu | Trp | Ser | Pro | Ser | Thr | Lys | Trp | His | Asn | Ser | Tyr | 200 |

| AGG | GAG | CCC | TTC | GAG | CAG | CAC | CTC | CTG | CTG | GGC | GTC | AGC | GTT | TCC | 645 |
| Arg | Glu | Pro | Phe | Glu | Gln | His | <u>Leu</u> | <u>Leu</u> | <u>Leu</u> | <u>Gly</u> | <u>Val</u> | <u>Ser</u> | <u>Val</u> | <u>Ser</u> | 215 |

| TGC | ATT | GTC | ATC | CTG | GCC | GTC | TGC | CTG | TTG | TGC | TAT | GTC | AGC | ATC | 690 |
| <u>Cys</u> | <u>Ile</u> | <u>Val</u> | <u>Ile</u> | <u>Leu</u> | <u>Ala</u> | <u>Val</u> | <u>Cys</u> | <u>Leu</u> | <u>Leu</u> | <u>Cys</u> | <u>Tyr</u> | <u>Val</u> | <u>Ser</u> | <u>Ile</u> | 230 |

| ACC | AAG | ATT | AAG | AAA | GAA | TGG | TGG | GAT | CAG | ATT | CCC | AAC | CCA | GCC | 735 |
| <u>Thr</u> | Lys | Ile | Lys | Lys | Glu | Trp | Trp | Asp | Gln | Ile | Pro | Asn | Pro | Ala | 245 |

FIGURE 4B

| | | | | | | | | | | | | | |
|---|---|---|---|---|---|---|---|---|---|---|---|---|---|
| CGC | AGC | CGC | CTC | GTG | GCT | ATA | ATA | ATC | CAG | GAT | GCT | CAG | GGG | TCA | 780 |
| Arg | Ser | Arg | Leu | Val | Ala | Ile | Ile | Ile | Gln | Asp | Ala | Gln | Gly | Ser | 260 |

```
CGC AGC CGC CTC GTG GCT ATA ATA ATC CAG GAT GCT CAG GGG TCA   780
Arg Ser Arg Leu Val Ala Ile Ile Ile Gln Asp Ala Gln Gly Ser   260

CAG TGG GAG AAG CGG TCC CGA GGC CAG GAA CCA GCC AAG TGC CCA   825
Gln Trp Glu Lys Arg Ser Arg Gly Gln Glu Pro Ala Lys Cys Pro   275

CAC TGG AAG AAT TGT CTT ACC AAG CTC TTG CCC TGT TTT CTG GAG   870
His Trp Lys Asn Cys Leu Thr Lys Leu Leu Pro Cys Phe Leu Glu   290

CAC AAC ATG AAA AGG GAT GAA GAT CCT CAC AAG GCT GCC AAA GAG   915
His Asn Met Lys Arg Asp Glu Asp Pro His Lys Ala Ala Lys Glu   305

ATG CCT TTC CAG GGC TCT GGA AAA TCA GCA TGG TGC CCA GTG GAG   960
Met Pro Phe Gln Gly Ser Gly Lys Ser Ala Trp Cys Pro Val Glu   320

ATC AGC AAG ACA GTC CTC TGG CCA GAG AGC ATC AGC GTG GTG CGA  1005
Ile Ser Lys Thr Val Leu Trp Pro Glu Ser Ile Ser Val Val Arg   335

TGT GTG GAG TTG TTT GAG GCC CCG GTG GAG TGT GAG GAG GAG GAG  1050
Cys Val Glu Leu Phe Glu Ala Pro Val Glu Cys Glu Glu Glu Glu   350

GAG GTA GAG GAA GAA AAA GGG AGC TTC TGT GCA TCG CCT GAG AGC  1095
Glu Val Glu Glu Glu Lys Gly Ser Phe Cys Ala Ser Pro Glu Ser   365

AGC AGG GAT GAC TTC CAG GAG GGA AGG GAG GGC ATT GTG GCC CGG  1140
Ser Arg Asp Asp Phe Gln Glu Gly Arg Glu Gly Ile Val Ala Arg   380

CTA ACA GAG AGC CTG TTC CTG GAC CTG CTC GGA GAG GAG AAT GGG  1185
Leu Thr Glu Ser Leu Phe Leu Asp Leu Leu Gly Glu Glu Asn Gly   395

GGC TTT TGC CAG CAG GAC ATG GGG GAG TCA TGC CTT CTT CCA CCT  1230
Gly Phe Cys Gln Gln Asp Met Gly Glu Ser Cys Leu Leu Pro Pro   410

TCG GGA AGT ACG AGT GCT CAC ATG CCC TGG GAT GAG TTC CCA AGT  1275
Ser Gly Ser Thr Ser Ala His Met Pro Trp Asp Glu Phe Pro Ser   425

GCA GGG CCC AAG GAG GCA CCT CCC TGG GGC AAG GAG CAG CCT CTC  1320
Ala Gly Pro Lys Glu Ala Pro Pro Trp Gly Lys Glu Gln Pro Leu   440

CAC CTG GAG CCA AGT CCT CCT GCC AGC CCG ACC CAG AGT CCA GAC  1365
His Leu Glu Pro Ser Pro Pro Ala Ser Pro Thr Gln Ser Pro Asp   455

AAC CTG ACT TGC ACA GAG ACG CCC CTC GTC ATC GCA GGC AAC CCT  1410
Asn Leu Thr Cys Thr Glu Thr Pro Leu Val Ile Ala Gly Asn Pro   470

GCT TAC CGC AGC TTC AGC AAC TCC CTG AGC CAG TCA CCG TGT CCC  1455
Ala Tyr Arg Ser Phe Ser Asn Ser Leu Ser Gln Ser Pro Cys Pro   485

AGA GAG CTG GGT CCA GAC CCA CTG CTG GCC AGA CAC CTG GAG GAA  1500
Arg Glu Leu Gly Pro Asp Pro Leu Leu Ala Arg His Leu Glu Glu   500

GTA GAA CCC GAG ATG CCC TGT GTC CCC CAG CTC TCT GAG CCA ACC  1545
Val Glu Pro Glu Met Pro Cys Val Pro Gln Leu Ser Glu Pro Thr   515
```

FIGURE 4C

```
ACT GTG CCC CAA CCT GAG CCA GAA ACC TGG GAG CAG ATC CTC CGC    1590
Thr Val Pro Gln Pro Glu Pro Glu Thr Trp Glu Gln Ile Leu Arg     530

CGA AAT GTC CTC CAG CAT GGG GCA GCT GCA GCC CCC GTC TCG GCC    1635
Arg Asn Val Leu Gln His Gly Ala Ala Ala Ala Pro Val Ser Ala     545

CCC ACC AGT GGC TAT CAG GAG TTT GTA CAT GCG GTG GAG CAG GGT    1680
Pro Thr Ser Gly Tyr Gln Glu Phe Val His Ala Val Glu Gln Gly     560

GGC ACC CAG GCC AGT GCG GTG GTG GGC TTG GGT CCC CCA GGA GAG    1725
Gly Thr Gln Ala Ser Ala Val Val Gly Leu Gly Pro Pro Gly Glu     575

GCT GGT TAC AAG GCC TTC TCA AGC CTG CTT GCC AGC AGT GCT GTG    1770
Ala Gly Tyr Lys Ala Phe Ser Ser Leu Leu Ala Ser Ser Ala Val     590

TCC CCA GAG AAA TGT GGG TTT GGG GCT AGC AGT GGG GAA GAG GGG    1815
Ser Pro Glu Lys Cys Gly Phe Gly Ala Ser Ser Gly Glu Glu Gly     605

TAT AAG CCT TTC CAA GAC CTC ATT CCT GGC TGC CCT GGG GAC CCT    1860
Tyr Lys Pro Phe Gln Asp Leu Ile Pro Gly Cys Pro Gly Asp Pro     620

GCC CCA GTC CCT GTC CCC TTG TTC ACC TTT GGA CTG GAC AGG GAG    1905
Ala Pro Val Pro Val Pro Leu Phe Thr Phe Gly Leu Asp Arg Glu     635

CCA CCT CGC AGT CCG CAG AGC TCA CAT CTC CCA AGC AGC TCC CCA    1950
Pro Pro Arg Ser Pro Gln Ser Ser His Leu Pro Ser Ser Ser Pro     650

GAG CAC CTG GGT CTG GAG CCG GGG GAA AAG GTA GAG GAC ATG CCA    1995
Glu His Leu Gly Leu Glu Pro Gly Glu Lys Val Glu Asp Met Pro     665

AAG CCC CCA CTT CCC CAG GAG CAG GCC ACA GAC CCC CTT GTG GAC    2040
Lys Pro Pro Leu Pro Gln Glu Gln Ala Thr Asp Pro Leu Val Asp     680

AGC CTG GGC AGT GGC ATT GTC TAC TCA GCC CTT ACC TGC CAC CTG    2085
Ser Leu Gly Ser Gly Ile Val Tyr Ser Ala Leu Thr Cys His Leu     695

TGC GGC CAC CTG AAA CAG TGT CAT GGC CAG GAG GAT GGT GGC CAG    2130
Cys Gly His Leu Lys Gln Cys His Gly Gln Glu Asp Gly Gly Gln     710

ACC CCT GTC ATG GCC AGT CCT TGC TGT GGC TGC TGC TGT GGA GAC    2175
Thr Pro Val Met Ala Ser Pro Cys Cys Gly Cys Cys Cys Gly Asp     725

AGG TCC TCG CCC CCT ACA ACC CCC CTG AGG GCC CCA GAC CCC TCT    2220
Arg Ser Ser Pro Pro Thr Thr Pro Leu Arg Ala Pro Asp Pro Ser     740

CCA GGT GGG GTT CCA CTG GAG GCC AGT CTG TGT CCG GCC TCC CTG    2265
Pro Gly Gly Val Pro Leu Glu Ala Ser Leu Cys Pro Ala Ser Leu     755

GCA CCC TCG GGC ATC TCA GAG AAG AGT AAA TCC TCA TCA TCC TTC    2310
Ala Pro Ser Gly Ile Ser Glu Lys Ser Lys Ser Ser Ser Ser Phe     770

CAT CCT GCC CCT GGC AAT GCT CAG AGC TCA AGC CAG ACC CCC AAA    2355
His Pro Ala Pro Gly Asn Ala Gln Ser Ser Ser Gln Thr Pro Lys     785

ATC GTG AAC TTT GTC TCC GTG GGA CCC ACA TAC ATG AGG GTC TCT    2400
Ile Val Asn Phe Val Ser Val Gly Pro Thr Tyr Met Arg Val Ser     800
```

FIGURE 5A

```
  1 MGWLCSGLLFPVSCLVLLQVASSGNMKVLQEPTCVSDYMSISTCEWKMNG  50
    || ||   |  || ||  |   ||   ||| ||||  ||   |||||
  1 MGRLCTKFLTSVGCLILLLVTGSGSIKVLGEPTCFSDYIRTSTCEWFLDS  50

51 PTNCSTELRLLYQLVFL.LSEAHTCIPENNGGAGCVCHLLMDDVVSADNY  99
    ||  | |  ||  |    ||  ||| ||  | |  ||||    |   |  | |
 51 AVDCSSQLCLHYRLMFFEFSENLTCIPRNSASTVCVCHMEMNRPVQSDRY 100

100 TLDLWAGQQLLWKGSFKPSEHVKPRAPGNLTVHTNVSDTLLLTWSNPYPP 149
    |||    || ||| ||   |||  || || ||||||  |||||  | ||
101 QMELWAEHRQLWQGSFSPSGNVKPLAPDNLTLHTNVSDEWLLTWNNLYPS 150

150 DNYLYNHLTYAVNIWSENDPADFRIYNVTYLEPSLRIAASTLKSGISYRA 199
    | ||   |  |||  |   || | ||||||  ||  |     ||  | |
151 NNLLYKDLISMVNISREDNPAEFIVYNVTYKEPRLSFPINILMSGVYYTA 200

200 RVRAWAQCYNTTWSEWSPSTKWHNSYREPFEQHLLLGVSVSCIVILAVCL 249
    ||| |   |   ||||||||| | |||| |   |  ||  |  |  ||
201 RVRVRSQILTGTWSEWSPSITWYNHFQLPLIQRLPLGVTISCLCIPLFCL 250

250 LCYVSITKIKKEWWDQIPNPARSRLVAIIQDAQGSQWEKRSRGQEPAKC 299
    || |||||||| |||||| |||| ||||||||||  |  |  |  | |
251 FCYFSITKIKKIWWDQIPTPARSPLVAIIIQDAQVPLWDKQTRSQESTKY 300

300 PHWKNCLTKLLPCFLEHNMKRDEDPHKAAKEMPFQGSGKSAWCPVEISKT 349
    |||| || |||||||| |   |  |    |  |   |  ||| |  | |
301 PHWKTCLDKLLPCLLKHRVKKKTDFPKAAPTKSLQSPGKAGWCPMEVSRT 350

350 VLWPE...SISVVRCVELFEAPVECEEEEVEEEKGSFCASPESSRD.DFQ 396
    ||||     |||||||| |||||| ||||  |||     ||||  ||
351 VLWPENVSVSVVRCMELFEAPVQNVEEEEDEIVKEDLSMSPENSGGCGFQ 400

397 EGREGIVARLTESLFLDLLGEENGGFCQQDMGESCLLPPSGSTSAHMPWD 446
    |    |||||||| | ||| ||| ||   |   |   ||||
401 ESQADIMARLTENLFSDLLEAENGGLGQSALAESCSPLPSGSGQASVSWA 450

447 EFPSAGPKEAPPWGKEQPLHLEPSPPASPTQSPDNLTCTETPLVIAGNPA 496
    |   ||    |||   |||||  ||  || || ||  |||| ||| |||
451 CLPMGPSEEATCQVTEQPSHPGP.LSGSPAQSAPTLACTQVPLVLADNPA 499

497 YRSFSNSLSQSPCPRELGPDPLLARHLEEVEPEMCVPQLSEPTTVPQPE 546
    ||||| |  |  | |   |  |  |||||  |   |   | |   |
500 YRSFSDCCSPAPNPGELAPEQQQADHLEEEEPPSPADPHSSGP...PMQP 546

547 PETWEQILRRNVLQHGAAAAPVSAPTSGYQEFVHAVEQGGTQASAVVGLG 596
    | ||||||  |||||||| | |  || ||||| |  | |  |   |
547 VESWEQILHMSVLQHGAAAGSTPAPAGGYQEFVQAVKQGAAQDPGVPGVR 596

597 PPGEAGYKAFSSLLASSAVSPEKCGFGASSGEEGYKPFQDLIPGCPGDPA 646
    |  | ||||||||||  |   |       |   ||||||   |   |
597 PSGDPGYKAFSSLLSSNGIRGDTAAGTDDGHGGYKPFQNPVP....NQS 642
```

FIGURE 5B

```
647 PVPVPLFTFGLDREPPRSPQSSHLPSSSPEHLGLEPGEKVEDMPKPPLPQ 696
        | ||||||||| |   ||  |  | | ||  ||||  | |   |  | |
643 PSSVPLFTFGLDTELSPSPLNSDPPKSPPECLGLELGLKGGDWVKAPPPA 692

697 EQATDPLVDSLGSGIVYSALTCHLCGHLKQCHGQEDGGQTPVMASPCCGC 746
     |   |  | || ||||||  |||||||||||| | ||| |  |  ||| |||
693 DQVPKPFGDDLGFGIVYSSLTCHLCGHLKQHHSQEEGGQSPIVASPGCGC 742

747 CCGDRSSPPTTPLRAPDPSPGGVPLEASLCPASLAPSGISEKSKSSSSFH 796
    |  |||       |    ||||| ||  | ||   || |   |
743 CYDDRSPSLGSLSGALESCPEGIPPEANLMSAPKTPSNLSGEGK...... 786

797 PAPGNAQSSSQTPKIVNFVSVGPTYMRVS 825
     ||       |||       | ||          ||
787 .GPGHSPVPSQTTE....VPVGALGIAVS 810
``` sIL-4R Inhibition of Anti-TNP-KLH
IgE Sera Levels

○ 1-No Boost
△ 1-2
▲ 25 μg sIL-4R
● 5 μg sIL-4R
■ 1 μg sIL-4R
□ 11B11
◇ Saline Control Effects of sIL-4R on DTH Response to SRBC in Mice

USE OF INTERLEUKIN-4 RECEPTORS TO INHIBIT BIOLOGICAL RESPONSES MEDIATED BY INTERLEUKIN-4

CROSS-REFERENCE TO RELATED APPLICATIONS

This is a divisional of application Ser. No. 08/094,669, filed Jul. 20, 1993, now U.S. Pat. No. 5,599,905, which is a divisional of application Ser. No. 07/480,694, filed Feb. 14, 1990, currently pending, which is a continuation-in-part of application Ser. No. 07/370,924, filed Jun. 23, 1989, now abandoned which is a continuation-in-part of Ser. No. 07/326,156, filed Mar. 20, 1989, now abandoned, which is a continuation-in-part of Ser. No. 07/319,438, filed Mar. 2, 1989, now abandoned, which is a continuation-in-part of Ser. No. 07/265,047, filed Oct. 31, 1988, now abandoned.

BACKGROUND OF THE INVENTION

The present invention relates generally to cytokine receptors and, more specifically, to Interleukin-4 receptors.

Interleukin-4 (IL-4, also known as B cell stimulating factor, or BSF-1) was originally characterized by its ability to stimulate the proliferation of B cells in response to low concentrations of antibodies directed to surface immunoglobulin. More recently, IL-4 has been shown to possess a far broader spectrum of biological activities, including growth co-stimulation of T cells, mast cells, granulocytes, megakaryocytes, and erythrocytes. In addition, IL-4 stimulates the proliferation of several IL-2- and IL-3-dependent cell lines, induces the expression of class II major histocompatibility complex molecules on resting B cells, and enhances the secretion of IgE and IgG1 isotypes by stimulated B cells. Both murine and human IL-4 have been definitively characterized by recombinant DNA technology and by purification to homogeneity of the natural murine protein (Yokota et al., *Proc. Natl. Acad. Sci. USA* 83:5894, 1986; Noma et al., *Nature* 319:640, 1986; and Grabstein et al., *J. Exp. Med.* 163:1405, 1986).

The biological activities of IL-4 are mediated by specific cell surface receptors for IL-4 which are expressed on primary cells and in vitro cell lines of mammalian origin. IL-4 binds to the receptor, which then transduces a biological signal to various immune effector cells. Purified IL-4 receptor (IL-4R) compositions will therefore be useful in diagnostic assays for IL-4 or IL-4 receptor, and in raising antibodies to IL-4 receptor for use in diagnosis or therapy. In addition, purified IL-4 receptor compositions may be used directly in therapy to bind or scavenge IL-4, providing a means for regulating the biological activities of this cytokine.

Although IL-4 has been extensively characterized, little progress has been made in characterizing its receptor. Numerous studies documenting the existence of an IL-4 receptor on a wide range of cell types have been published; however, structural characterization has been limited to estimates of the molecular weight of the protein as determined by SDS-PAGE analysis of covalent complexes formed by chemical cross-linking between the receptor and radiolabeled IL-4 molecules. Ohara et al. (*Nature* 325:537, 1987) and Park et al. (*Proc. Natl. Acad. Sci. USA* 84:1669, 1987) first established the presence of an IL-4 receptor using radioiodinated recombinant murine IL-4 to bind a high affinity receptor expressed in low numbers on B and T lymphocytes and a wide range of cells of the hematopoietic lineage. By affinity cross-linking $^{125}$I-IL-4 to IL-4R, Ohara et al. and Park et al. identified receptor proteins having apparent molecular weights of 60,000 and 75,000 daltons, respectively. It is possible that the small receptor size observed on the murine cells represents a proteolytically cleaved fragment of the native receptor. Subsequent experiments by Park et al. (*J. Exp. Med.* 166:476, 1987) using yeast-derived recombinant human IL-4 radiolabeled with $^{125}$I showed that human IL-4 receptor is present not only on cell lines of B, T, and hematopoietic cell lineages, but is also found on human fibroblasts and cells of epithelial and endothelial origin. IL-4 receptors have since been shown to be present on other cell lines, including CBA/N splenic B cells (Nakajima et al., *J. Immunol.* 139:774, 1987), Burkitt lymphoma Jijoye cells (Cabrillat et al., *Biochem. & Biophys. Res. Commun.* 149:995, 1987), a wide variety of hemopoietic and nonhemopoietic cells (Lowenthal et al., *J. Immunol.* 140:456, 1988), and murine Lyt-2$^-$/L3T4$^-$ thymocytes. More recently, Park et al. (UCLA Symposia, *J. Cell Biol.*, Suppl. 12A, 1988) reported that, in the presence of sufficient protease inhibitors, $^{125}$I-IL-4-binding plasma membrane receptors of 138–145 kDa could be identified on several murine cell lines. Considerable controversy thus remains regarding the actual size and structure of IL-4 receptors.

Further study of the structure and biological characteristics of IL-4 receptors and the role played by IL-4 receptors in the responses of various cell populations to IL-4 or other cytokine stimulation, or of the methods of using IL-4 receptors effectively in therapy, diagnosis, or assay, has not been possible because of the difficulty in obtaining sufficient quantities of purified IL-4 receptor. No cell lines have previously been known to express high levels of IL-4 receptors constitutively and continuously, and in cell lines known to express detectable levels of IL-4 receptor, the level of expression is generally limited to less than about 2000 receptors per cell. Thus, efforts to purify the IL-4 receptor molecule for use in biochemical analysis or to clone and express mammalian genes encoding IL-4 receptor have been impeded by lack of purified receptor and a suitable source of receptor mRNA.

SUMMARY OF THE INVENTION

The present invention provides DNA sequences encoding mammalian Interleukin-4 receptors (IL-4R) or subunits thereof. Preferably, such DNA sequences are selected from the group consisting of: (a) cDNA clones having a nucleotide sequence derived from the coding region of a native IL-4R gene; (b) DNA sequences capable of hybridization to the cDNA clones of (a) under moderately stringent conditions and which encode biologically active IL-4R molecules; and (c) DNA sequences which are degenerate, as a result of the genetic code, to the DNA sequences defined in (a) and (b) and which encode biologically active IL-4R molecules. The present invention also provides recombinant expression vectors comprising the DNA sequences defined above, recombinant IL-4R molecules produced using the recombinant expression vectors, and processes for producing the recombinant IL-4R molecules using the expression vectors.

The present invention also provides substantially homogeneous protein compositions comprising mammalian IL-4R. The full length murine molecule is a glycoprotein having a molecular weight of about 130,000 to about 140,000 $M_r$ by SDS-PAGE. The apparent binding affinity ($K_a$) for COS cells transfected with murine IL-4 receptor clones 16 and 18 from the CTLL 19.4 library is 1 to 8×10$^9$ M$^{-1}$. The $K_a$ for COS cells transfected with murine IL-4 receptor clones 7B9-2 and 7B9-4 from the murine 7B9 library is 2×10$^9$ to 1×10$^{10}$ M$^{-1}$. The mature murine IL-4 receptor molecule has an N-terminal amino acid sequence as follows: I K V L G E P T C F S D Y I R T S T C E W.

The human IL-4R molecule is believed to have a molecular weight of between about 110,000 and 150,000 $M_r$ and has an N-terminal amino acid sequence, predicted from the cDNA sequence and by analogy to the biochemically determined N-terminal sequence of the mature murine protein, as follows: M K V L Q E P T C V S D Y M S I S T C E W.

The present invention also provides compositions for use in therapy, diagnosis, assay of IL-4 receptor, or in raising antibodies to IL-4 receptors, comprising effective quantities of soluble receptor proteins prepared according to the foregoing processes. Such soluble recombinant receptor molecules include truncated proteins wherein regions of the receptor molecule not required for IL-4 binding have been deleted.

The present invention also provides a method for suppressing IL-4 mediated immune or inflammatory responses. This method comprises administering an effective quantity of soluble IL-4 receptor (sIL-4R), in association with a pharmaceutical carrier, to a mammal, including man. sIL-4R suppresses IL-4 dependent immune or inflammatory responses, including, for example, B cell mediated activities, such as B cell proliferation, immunoglobulin secretion, and expression of FcεR which are induced by IL-4. sIL-4R also suppresses cytotoxic T cell induction. Clinical applications of sIL-4R include, for example, use in allergy therapy to selectively suppress IgE synthesis and use in transplantation therapy to prevent allograft rejection. sIL-4R is also useful to suppress delayed-type hypersensitivity or contact hypersensitivity reactions. sIL-4R is highly specific in its immunosuppressive activity because it suppresses only IL-4 mediated immune responses.

These and other aspects of the present invention will become evident upon reference to the following detailed description and attached drawings.

BRIEF DESCRIPTION OF THE DRAWINGS

FIGS. 2A–C depict the cDNA sequence and the derived amino acid sequence of the coding region of a murine IL-4 receptor, as derived from clone 7B9-2 of the 7B9 library. The N-terminal isoleucine of the mature protein is designated amino acid number 1. The coding region of the full-length membrane-bound protein from clone 7B9-2 is defined by amino acids 1-785. The ATC codon specifying the isoleucine residue constituting the mature N-terminus is underlined at position 1 of the protein sequence; the putative transmembrane region at amino acids 209-232 is also underlined. The sequences of the coding regions of clones 7B9-4 and clones CTLL-18 and CTLL-16 of the CTLL 19.4 library are identical to that of 7B9-2 except as follows. The coding region of CTLL-16 encodes a membrane-bound IL-4-binding receptor defined by amino acids −25 through 233 (including the putative 25 amino acid signal peptide sequence), but is followed by a TAG terminator codon (not shown) which ends the open reading frame. The nucleic acid sequence indicates the presence of a splice donor site at this position (indicated by an arrow in FIG. 1) and a splice acceptor site near the 3' end (indicated by a second arrow), suggesting that CTLL-16 was derived from an unspliced mRNA intermediate. Clones 7B9-4 and CTLL-18 encode amino acids 23 through 199 and −25 through 199, respectively. After amino acid 199, a 114-base pair insert (identical in both clones and shown by an open box in FIG. 1) introduces six new amino acids, followed by a termination codon. This form of the receptor is soluble.

FIGS. 4A–C depict the coding sequence of a human IL-4 receptor cDNA from clone T22-8, which was obtained from a cDNA library derived from the T cell line T22. The predicted N-terminal methionine of the mature protein and the transmembrane region are underlined.

FIGS. 5A–B are a comparison of the predicted amino acid sequences of human (top line) and murine (bottom line) IL-4 receptor cDNA clones.

DETAILED DESCRIPTION OF THE INVENTION

Definitions

Figure 1:
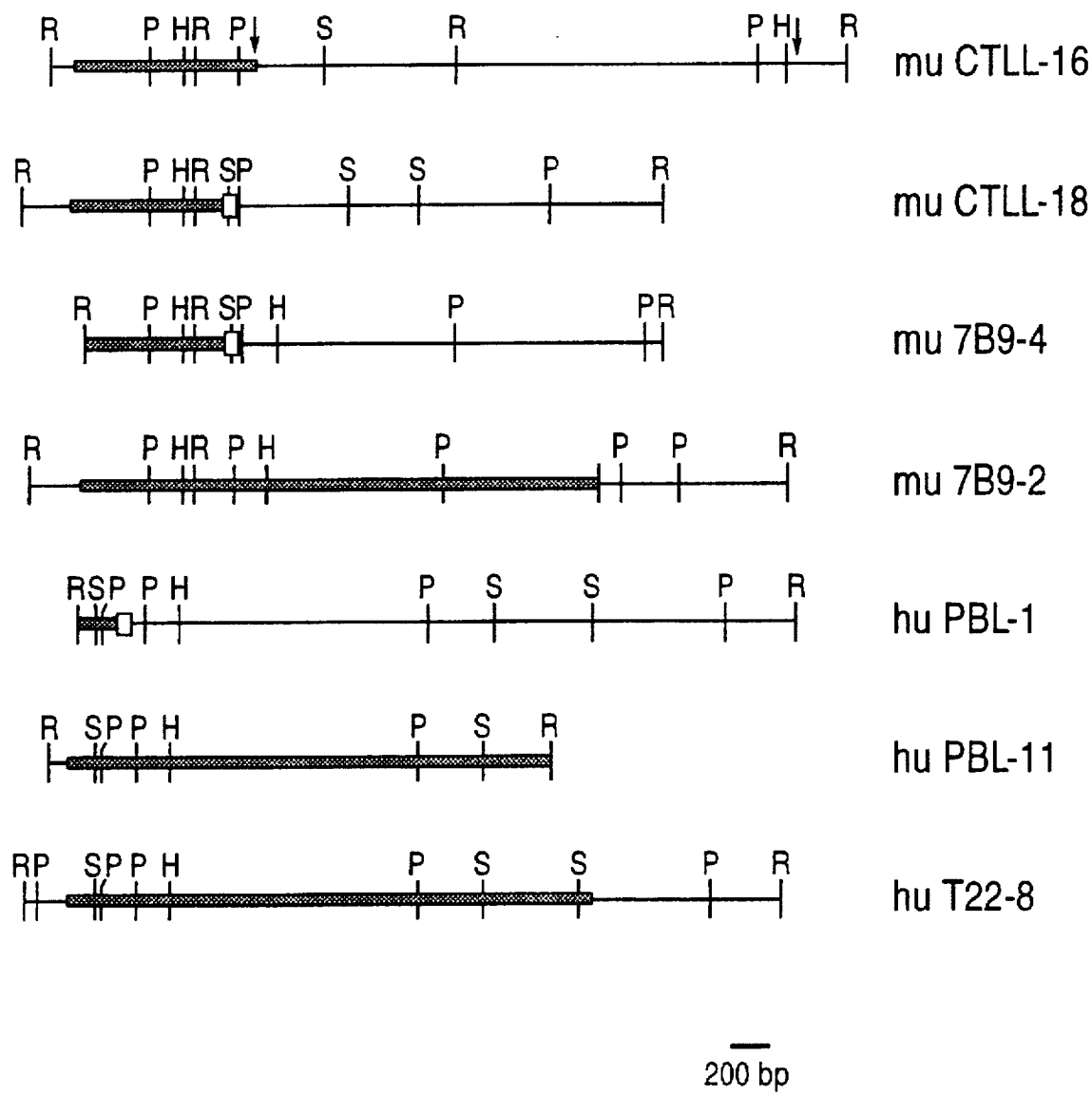
FIG. 1 shows restriction maps of cDNA clones containing the coding regions (denoted by a bar) of the murine and human IL-4R cDNAs. The restriction sites EcoRI, PvuII, Hinc II and Sst I are represented by the letters R, P, H and S, respectively.

"Interleukin-4" and "IL-4" (also referred to as B cell stimulating factor, or BSF-1) is a T cell-derived cytokine involved in the regulation of immune and inflammatory responses. The biological activities of IL-4 are mediated through binding to specific cell surface receptors, referred to as "Interleukin-4 receptors", "IL-4 receptors" or simply "IL-4R". "IL-4 mediated" immune or inflammatory responses include all biological responses which are caused by the binding of IL-4 to a native IL-4 receptor (bound to a cell surface) or which may be inhibited or suppressed by preventing IL-4 from binding to a native IL-4 receptor. IL-4 mediated biological responses include, for example, IL-4 induced proliferation of antigen-primed B lymphocytes, expression of class II major histocompatibility complex molecules on resting B cells, secretion and expression of antibodies of the IgE and IgG1 isotype, and regulation of the expression of the low affinity Fc receptor for IgE (CD23) on lymphocytes and monocytes. Outside the B lymphocyte compartment, IL-4 mediated biological responses include the proliferation of a variety of primary cells and in vitro cell lines, including factor-dependent T cell and mast cell lines, murine and human T lymphocytes, thymocytes, and connective tissue-type mast cells. IL-4 also induces both murine and human cytotoxic T cells. Under certain conditions, IL-4 inhibits the response of lymphoid cells to IL-2. IL-4 acts on both murine and human hematopoietic progenitor cells to either stimulate or suppress in vitro formation of colonies in combination with known colony stimulating factors. IL-4 also induces class I and class II MHC molecules on more mature cells of the monocytic lineage, enhances antigen presenting ability and promotes formation of giant multinucleated cells. Specific clinical conditions which may be mediated by IL-4 include, for example, graft rejection, graft versus host disease, allergy, asthma and delayed-type hypersensitivity responses.

As used herein, the terms "IL-4 receptor" or "IL-4R" refer to proteins which bind interleukin-4 (IL-4) molecules and, in their native configuration as intact human plasma membrane proteins, play a role in transducing the biological signal provided by IL-4 to a cell. Intact receptor proteins generally include an extracellular region which binds to a ligand, a hydrophobic transmembrane region which causes the protein to be immobilized within the plasma membrane lipid bilayer, and a cytoplasmic or intracellular region which interacts with cytoplasmic proteins and/or chemicals to deliver a biological signal to effector cells via a cascade of chemical reactions within the cytoplasm of the cell. The hydrophobic transmembrane region and a highly charged sequence of amino acids in the cytoplasmic region immediately following the transmembrane region cooperatively function to halt transport of the IL-4 receptor across the plasma membrane.

"IL-4 receptors" are proteins having amino acid sequences which are substantially similar to the native mammalian Interleukin-4 receptor amino acid sequences disclosed in FIGS. 2 and 4 or fragments thereof, and which are biologically active as defined below, in that they are capable of binding Interleukin-4 (IL-4) molecules or transducing a biological signal initiated by an IL-4 molecule binding to a cell, or cross-reacting with anti-IL-4R antibodies raised against IL-4R from natural (i.e., nonrecombinant) sources. The native human IL-4 receptor molecule has an apparent molecular weight by SDS-PAGE of about 140 kilodaltons (kDa). The native murine IL-4 receptor molecule has an apparent molecular weight by SDS-PAGE of about 140 kilodaltons (kDa). The terms "IL-4 receptor" or "IL-4R" include, but are not limited to, soluble IL-4 receptors, as defined below. Specific IL-4 receptor polypeptides are designated herein by parenthetically indicating the amino acid sequence numbers, followed by any additional amino acid sequences. For Example, human IL-4R (1-207) refers to a human IL-4R protein having the sequence of amino acids 1-207 as shown in FIG. 4A. Human IL-4R (1-184) Pro Ser Asn Glu Asn refers to a human IL-4R protein having the sequence of amino acids 1-184 as shown in FIG. 4A, followed by the amino acid sequence Pro Ser Asn Glu Asn. As used throughout the specification, the term "mature" means a protein expressed in a form lacking a leader sequence as may be present in full-length transcripts of a native gene. Various bioequivalent protein and amino acid analogs are described in the detailed description of the invention.

"Substantially similar" IL-4 receptors include those whose amino acid or nucleic acid sequences vary from the native sequences by one or more substitutions, deletions, or additions, the net effect of which is to retain biological activity of the IL-4R protein. For example, nucleic acid subunits and analogs are "substantially similar" to the specific DNA sequences disclosed herein if: (a) the DNA sequence is derived from the coding region of a native mammalian IL-4R gene; (b) the DNA sequence is capable of hybridization to DNA sequences of (a) under moderately stringent conditions and which encode biologically active IL-4R molecules; or DNA sequences which are degenerate as a result of the genetic code to the DNA sequences defined in (a) or (b) and which encode biologically active IL-4R molecules. Substantially similar analog proteins will generally be greater than about 30 percent similar to the corresponding sequence of the native IL-4R. Sequences having lesser degrees of similarity but comparable biological activity are considered to be equivalents. More preferably, the analog proteins will be greater than about 80 percent similar to the corresponding sequence of the native IL-4R, in which case they are defined as being "substantially identical." In defining nucleic acid sequences, all subject nucleic acid sequences capable of encoding substantially similar amino acid sequences are considered substantially similar to a reference nucleic acid sequence. Percent similarity may be determined, for example, by comparing sequence information using the GAP computer program, version 6.0, available from the University of Wisconsin Genetics Computer Group (UWGCG). The GAP program utilizes the alignment method of Needleman and Wunsch (*J. Mol. Biol.* 48:443, 1970), as revised by Smith and Waterman (*Adv. Appl. Math.* 2:482, 1981). Briefly, the GAP program defines similarity as the number of aligned symbols (i.e., nucleotides or amino acids) which are similar, divided by the total number of symbols in the shorter of the two sequences. The preferred default parameters for the GAP program include: (1) a unary comparison matrix (containing a value of 1 for identities and 0 for non-identities) for nucleotides, and the weighted comparison matrix of Gribskov and Burgess, *Nucl. Acids Res.* 14:6745, 1986, as described by Schwartz and Dayhoff, ed., *Atlas of Protein Sequence and Structure*, National Biomedical Research Foundation, pp. 353–358, 1979; (2) a penalty of 3.0 for each gap and an additional 0.10 penalty for each symbol in each gap; and (3) no penalty for end gaps.

"Soluble IL-4 receptor" or "sIL4-R" as used in the context of the present invention refers to a protein, or a substantially equivalent analog, having an amino acid sequence corresponding to the extracellular region of native IL-4 receptors, for example, polypeptides having the amino acid sequences substantially equivalent to the sequences of amino acids 1-208 of FIG. 2, amino acids 1-207 of FIG. 4 or to the amino acid sequences discussed in Examples 8C and 9. Equivalent sIL-4Rs include polypeptides which vary from the sequences shown in FIGS. 2 or 4 by one or more substitutions, deletions, or additions, and which retain the ability to bind IL-4 and inhibit the ability of IL-4 to transduce a signal via cell surface bound IL-4 receptor proteins. Because sIL-4R proteins are devoid of a transmembrane region, they are secreted from the host cell in which they are produced. When administered in therapeutic formulations, sIL-4R proteins circulate in the body and bind to circulating IL-4 molecules, preventing interaction of IL-4 with natural IL-4 receptors and inhibiting transduction of IL-4 mediated biological signals, such as immune or inflammatory responses. The ability of a polypeptide to inhibit IL-4 signal transduction can be determined by transfecting cells with recombinant IL-4 receptor DNAs to obtain recombinant receptor expression. The cells are then contacted with IL-4 and the resulting metabolic effects examined. If an effect results which is attributable to the action of the ligand, then the recombinant receptor has signal transducing activity. Exemplary procedures for determining whether a polypeptide has signal transducing activity are disclosed by Idzerda et al., *J. Exp. Med.*, March 1990 in press, Curtis et al., *Proc. Natl. Acad. Sci. USA* 86:3045 (1989), Prywes et al., *EMBO J.* 5:2179 (1986) and Chou et al., *J. Biol. Chem.* 262:1842 (1987). Alternatively primary cells of cell lines which express an endogenous IL-4 receptor and have a detectable biological response to IL-4 could also be utilized. Such is the case with the CTLL-2 cell line which responds by short term proliferation in response to either IL-2 or IL-4; the IL-4 induced proliferation can be blocked specifically by the addition of exogenous soluble IL-4R (Mosley et al., *Cell* 59:335 (1989). In addition, any one of the in vivo or in vitro assays described in Examples 14–23 can be utilized to determine whether a soluble IL-4R inhibits transduction of a specific IL-4 mediated biological signal. The cloning, sequencing and expression of full-length and soluble forms of the receptor for murine IL-4 have recently been described by the applicants, Mosley et al., *Cell* 59:335, 1989, which publication is incorporated herein by reference.

"Recombinant," as used herein, means that a protein is derived from recombinant (e.g., microbial or mammalian) expression systems. "Microbial" refers to recombinant proteins made in bacterial or fungal (e.g., yeast) expression systems. As a product, "recombinant microbial" defines a protein produced in a microbial expression system which is essentially free of native endogenous substances. Protein expressed in most bacterial cultures, e.g., *E. coli*, will be free of glycan. Protein expressed in yeast may have a glycosylation pattern different from that expressed in mammalian cells.

"Biologically active," as used throughout the specification as a characteristic of IL-4 receptors, means that a particular molecule shares sufficient amino acid sequence similarity with the embodiments of the present invention disclosed herein to be capable of binding detectable quantities of IL-4, transducing an IL-4 signal to a cell, for example, as a component of a hybrid receptor construct, or cross-reacting with anti-IL-4R antibodies raised against IL-4R from natural (i.e., nonrecombinant) sources. Preferably, biologically active IL-4 receptors within the scope of the present invention are capable of binding greater than 0.1 nmoles IL-4 per nmole receptor, and most preferably, greater than 0.5 nmole IL-4 per nmole receptor in standard binding assays (see below).

"DNA sequence" refers to a DNA molecule, in the form of a separate fragment or as a component of a larger DNA construct, which has been derived from DNA isolated at least once in substantially pure form, i.e., free of contaminating endogenous materials and in a quantity or concentration enabling identification, manipulation, and recovery of the sequence and its component nucleotide sequences by standard biochemical methods, for example, using a cloning vector. Such sequences are preferably provided in the form of an open reading frame uninterrupted by internal nontranslated sequences, or introns, which are typically present in eukaryotic genes. Genomic DNA containing the relevant sequences could also be used. Sequences of non-translated DNA may be present 5' or 3' from the open reading frame, where the same do not interfere with manipulation or expression of the coding regions.

"Nucleotide sequence" refers to a heteropolymer of deoxyribonucleotides. DNA sequences encoding the proteins provided by this invention can be assembled from cDNA fragments and short oligonucleotide linkers, or from a series of oligonucleotides, to provide a synthetic gene which is capable of being expressed in a recombinant transcriptional unit.

"Recombinant expression vector" refers to a replicable DNA construct used either to amplify or to express DNA which encodes IL-4R and which includes a transcriptional unit comprising an assembly of (1) a genetic element or elements having a regulatory role in gene expression, for example, promoters or enhancers, (2) a structural or coding sequence which is transcribed into mRNA and translated into protein, and (3) appropriate transcription and translation initiation and termination sequences. Structural elements intended for use in yeast expression systems preferably include a leader sequence enabling extracellular secretion of translated protein by a host cell. Alternatively, where recombinant protein is expressed without a leader or transport sequence, it may include an N-terminal methionine residue. This residue may optionally be subsequently cleaved from the expressed recombinant protein to provide a final product.

"Recombinant microbial expression system" means a substantially homogeneous monoculture of suitable host microorganisms, for example, bacteria such as *E. coli* or yeast such as *S. cerevisiae*, which have stably integrated a recombinant transcriptional unit into chromosomal DNA or carry the recombinant transcriptional unit as a component of a resident plasmid. Generally, cells constituting the system are the progeny of a single ancestral transformant. Recombinant expression systems as defined herein will express heterologous protein upon induction of the regulatory elements linked to the DNA sequence or synthetic gene to be expressed.

Proteins and Analogs

The present invention provides substantially homogeneous recombinant mammalian IL-4R polypeptides substantially free of contaminating endogenous materials and, optionally, without associated native-pattern glycosylation. The native murine and human IL-4 receptor molecules are recovered from cell lysates as glycoproteins having an apparent molecular weight by SDS-PAGE of about 130–145 kilodaltons (kDa). Mammalian IL-4R of the present invention includes, by way of example, primate, human, murine, canine, feline, bovine, ovine, equine and porcine IL-4R. Derivatives of IL-4R within the scope of the invention also include various structural forms of the primary protein which retain biological activity. Due to the presence of ionizable amino and carboxyl groups, for example, an IL-4R protein may be in the form of acidic or basic salts, or in neutral form. Individual amino acid residues may also be modified by oxidation or reduction.

The primary amino acid structure may be modified by forming covalent or aggregative conjugates with other chemical moieties, such as glycosyl groups, lipids, phosphate, acetyl groups and the like, or by creating amino acid sequence mutants. Covalent derivatives are prepared by linking particular functional groups to IL-4R amino acid side chains or at the N- or C-termini. Other derivatives of IL-4R within the scope of this invention include covalent or aggregative conjugates of IL-4R or its fragments with other proteins or polypeptides, such as by synthesis in recombinant culture as N-terminal or C-terminal fusions. For example, the conjugated peptide may be a signal (or leader) polypeptide sequence at the N-terminal region of the protein which co-translationally or post-translationally directs transfer of the protein from its site of synthesis to its site of function inside or outside of the cell membrane or wall (e.g., the yeast α-factor leader). IL-4R protein fusions can comprise peptides added to facilitate purification or identification of IL-4R (e.g., poly-His). Specific examples of a poly-HIS fusion construct that is biologically active are soluble human IL-4R (1-207) His His and soluble human IL-4R (1-207) His His His His His His. The amino acid sequence of IL-4 receptor can also be linked to the peptide Asp-Tyr-Lys-Asp-Asp-Asp-Asp-Lys (DYKDDDDK) (Hopp et al., Bio/Technology 6:1204, 1988.) The latter sequence is highly antigenic and provides an epitope reversibly bound by a specific monoclonal antibody, enabling rapid assay and facile purification of expressed recombinant protein. This sequence is also specifically cleaved by bovine mucosal enterokinase at the residue immediately following the Asp-Lys pairing. Fusion proteins capped with this peptide may also be resistant to intracellular degradation in *E. coli*. A specific example of such a peptide is soluble human IL-4R (1-207) Asp Tyr Lys Asp Asp Asp Asp Lys.

IL-4R derivatives may also be used as immunogens, reagents in receptor-based immunoassays, or as binding agents for affinity purification procedures of IL-4 or other binding ligands. IL-4R derivatives may also be obtained by cross-linking agents, such as M-maleimidobenzoyl succinimide ester and N-hydroxysuccinimide, at cysteine and lysine residues. IL-4R proteins may also be covalently bound through reactive side groups to various insoluble substrates, such as cyanogen bromide-activated, bisoxirane-activated, carbonyldiimidazole-activated or tosyl-activated agarose structures, or by adsorbing to polyolefin surfaces (with or without glutaraldehyde cross-linking). Once bound to a substrate, IL-4R may be used to selectively bind (for purposes of assay or purification) anti-IL-4R antibodies or IL-4.

The present invention also includes IL-4R with or without associated native-pattern glycosylation. IL-4R expressed in yeast or mammalian expression systems, e.g., COS-7 cells, may be similar or significantly different in molecular weight and glycosylation pattern than the native molecules, depending upon the expression system. Expression of IL-4R DNAs in bacteria such as *E. coli* provides non-glycosylated molecules. Functional mutant analogs of mammalian IL-4R having inactivated N-glycosylation sites can be produced by oligonucleotide synthesis and ligation or by site-specific mutagenesis techniques. These analog proteins can be produced in a homogeneous, reduced-carbohydrate form in good yield using yeast expression systems. N-glycosylation sites in eukaryotic proteins are characterized by the amino acid triplet Asn-$A_1$-Z, where $A_1$ is any amino acid except Pro, and Z is Ser or Thr. In this sequence, asparagine provides a side chain amino group for covalent attachment of carbohydrate. Such a site can be eliminated by substituting another amino acid for Asn or for residue Z, deleting Asn or Z, or inserting a non-Z amino acid between $A_1$ and Z, or an amino acid other than Asn between Asn and $A_1$.

IL-4R derivatives may also be obtained by mutations of IL-4R or its subunits. An IL-4R mutant, as referred to herein, is a polypeptide homologous to IL-4R but which has an amino acid sequence different from native IL-4R because of a deletion, insertion or substitution. Like most mammalian genes, mammalian IL-4 receptors are presumably encoded by multi-exon genes. Alternative mRNA constructs which can be attributed to different mRNA splicing events following transcription, and which share large regions of identity or similarity with the cDNAs claimed herein, are considered to be within the scope of the present invention.

Bioequivalent analogs of IL-4R proteins may be constructed by, for example, making various substitutions of residues or sequences or deleting terminal or internal residues or sequences not needed for biological activity. For example, cysteine residues can be deleted or replaced with other amino acids to prevent formation of incorrect intramolecular disulfide bridges upon renaturation. Other approaches to mutagenesis involve modification of adjacent dibasic amino acid residues to enhance expression in yeast systems in which KEX2 protease activity is present. Generally, substitutions should be made conservatively; i.e., the most preferred substitute amino acids are those having physicochemical characteristics resembling those of the residue to be replaced. Similarly, when a deletion or insertion strategy is adopted, the potential effect of the deletion or insertion on biological activity should be considered.

Subunits of IL-4R may be constructed by deleting terminal or internal residues or sequences. Particularly preferred subunits include those in which the transmembrane region and intracellular domain of IL-4R are deleted or substituted with hydrophilic residues to facilitate secretion of the receptor into the cell culture medium. The resulting protein is a soluble IL-4R molecule which may retain its ability to bind IL-4. Particular examples of soluble IL-4R include polypeptides having substantial identity to soluble murine IL-4R (1-208), soluble human IL-4R (1-207) and soluble human IL-4R (1-198), all of which retain the biological activity of soluble human IL-4R (1-207). Chimeric polypeptides comprising fragments of human and murine IL-4R may also be constructed, for example, IL-4R (1-197) Pro Ser Asn Glu Asn Leu, which is comprised of the sequence of amino acids 1-197 of human IL-4R followed by the N-terminal six amino acids of soluble murine IL-4R clone 18. This polypeptide has been found to retain the biological activity of soluble IL-4R (1-207).

Mutations in nucleotide sequences constructed for expression of analog IL-4Rs must, of course, preserve the reading frame phase of the coding sequences and preferably will not create complementary regions that could hybridize to produce secondary mRNA structures, such as loops or hairpins, which would adversely affect translation of the receptor mRNA. Although a mutation site may be predetermined, it is not necessary that the nature of the mutation per se be predetermined. For example, in order to select for optimum characteristics of mutants at a given site, random mutagenesis may be conducted at the target codon and the expressed IL-4R mutants screened for the desired activity.

Not all mutations in the nucleotide sequence which encodes IL-4R will be expressed in the final product, for example, nucleotide substitutions may be made to enhance expression, primarily to avoid secondary structure loops in the transcribed mRNA (see EPA 75,444A, incorporated herein by reference), or to provide codons that are more readily translated by the selected host, e.g., the well-known *E. coli* preference codons for *E. coli* expression.

Mutations can be introduced at particular loci by synthesizing oligonucleotides containing a mutant sequence, flanked by restriction sites enabling ligation to fragments of the native sequence. Following ligation, the resulting reconstructed sequence encodes an analog having the desired amino acid insertion, substitution, or deletion.

Alternatively, oligonucleotide-directed site-specific mutagenesis procedures can be employed to provide an altered gene having particular codons altered according to the substitution, deletion, or insertion required. Exemplary methods of making the alterations set forth above are disclosed by Walder et al. (*Gene* 42:133, 1986); Bauer et al. (*Gene* 37:73, 1985); Craik (*BioTechniques, January* 1985, 12–19); Smith et al. (*Genetic Engineering: Principles and Methods*, Plenum Press, 1981); and U.S. Pat. Nos. 4,518,584 and 4,737,462, which are incorporated by reference herein.

Expression of Recombinant IL-4R

The present invention provides recombinant expression vectors which include synthetic or cDNA-derived DNA fragments encoding mammalian IL-4R or bioequivalent analogs operably linked to suitable transcriptional or translational regulatory elements derived from mammalian, microbial, viral or insect genes. Such regulatory elements include a transcriptional promoter, an optional operator sequence to control transcription, a sequence encoding suitable mRNA ribosomal binding sites, and sequences which control the termination of transcription and translation, as described in detail below. The ability to replicate in a host, usually conferred by an origin of replication, and a selection gene to facilitate recognition of transformants may additionally be incorporated. DNA regions are operably linked when they are functionally related to each other. For example, DNA for a signal peptide (secretory leader) is operably linked to DNA for a polypeptide if it is expressed as a precursor which participates in the secretion of the polypeptide; a promoter is operably linked to a coding sequence if it controls the transcription of the sequence; or a ribosome binding site is operably linked to a coding sequence if it is positioned so as to permit translation. Generally, operably linked means contiguous and, in the case of secretory leaders, contiguous and in reading frame.

DNA sequences encoding mammalian IL-4 receptors which are to be expressed in a microorganism will preferably contain no introns that could prematurely terminate transcription of DNA into mRNA; however, premature termination of transcription may be desirable, for example, where it would result in mutants having advantageous C-terminal truncations, for example, deletion of a transmembrane region to yield a soluble receptor not bound to the cell membrane. Due to code degeneracy, there can be considerable variation in nucleotide sequences encoding the same amino acid sequence; exemplary DNA embodiments are those corresponding to the nucleotide sequences shown in the Figures. Other embodiments include sequences capable of hybridizing to the sequences of the Figures under moderately stringent conditions (50° C., 2×SSC) and other sequences hybridizing or degenerate to those described above, which encode biologically active IL-4 receptor polypeptides.

DNA which codes for soluble IL-4R proteins may be isolated using the cloning techniques described in the examples or may be made by constructing cDNAs which encode only the extracellular domain of IL-4 receptor (devoid of a transmembrane region) using well-known methods of mutagenesis. Soluble forms of human IL-4 receptor are not yet known to exist and must therefore be constructed from isolated recombinant IL-4 receptor cDNAs. cDNAs which encode sIL-4R may be constructed, for example, by truncating a cDNA encoding the full length IL-4 receptor 5' of the transmembrane region, ligating synthetic oligonucleotides to regenerate truncated portions of the extracellular domain, if necessary, and providing a stop codon to terminate transcription. DNA sequences encoding the soluble IL-4 receptor proteins can be assembled from cDNA fragments and short oligonucleotide linkers, or from a series of oligonucleotides, to provide a synthetic gene which is capable of being expressed in a recombinant transcriptional unit. Such DNA sequences are preferably provided in the form of an open reading frame uninterrupted by internal nontranslated sequences, or introns, which are typically present in eukaryotic genes. Genomic DNA containing the relevant sequences could also be used. Sequences of non-translated DNA may be present 5' or 3' from the open reading frame, where the same do not interfere with manipulation or expression of the coding regions.

Transformed host cells are cells which have been transformed or transfected with IL-4R vectors constructed using recombinant DNA techniques. Transformed host cells ordinarily express IL-4R, but host cells transformed for purposes of cloning or amplifying IL-4R DNA do not need to express IL-4R. Expressed IL-4R will be deposited in the cell membrane or secreted into the culture supernatant, depending on the IL-4R DNA selected. Suitable host cells for expression of mammalian IL-4R include prokaryotes, yeast or higher eukaryotic cells under the control of appropriate promoters. Prokaryotes include gram negative or gram positive organisms, for example *E. coli* or bacilli. Higher eukaryotic cells include established cell lines of mammalian origin as described below. Cell-free translation systems could also be employed to produce mammalian IL-4R using RNAs derived from the DNA constructs of the present invention. Appropriate cloning and expression vectors for use with bacterial, fungal, yeast, and mammalian cellular hosts are described by Pouwels et al. (*Cloning Vectors: A Laboratory Manual*, Elsevier, New York, 1985), the relevant disclosure of which is hereby incorporated by reference.

Prokaryotic expression hosts may be used for expression of IL-4Rs that do not require extensive proteolytic and disulfide processing. Prokaryotic expression vectors generally comprise one or more phenotypic selectable markers, for example a gene encoding proteins conferring antibiotic resistance or supplying an autotrophic requirement, and an origin of replication recognized by the host to ensure amplification within the host. Suitable prokaryotic hosts for transformation include *E. coli, Bacillus subtilis, Salmonella typhimurium*, and various species within the genera Pseudomonas, Streptomyces, and Staphylococcus, although others may also be employed as a matter of choice.

Useful expression vectors for bacterial use can comprise a selectable marker and bacterial origin of replication derived from commercially available plasmids comprising genetic elements of the well known cloning vector pBR322 (ATCC 37017). Such commercial vectors include, for example, pKK223-3 (Pharmacia Fine Chemicals, Uppsala, Sweden) and pGEM1 (Promega Biotec, Madison, Wis., USA). These pBR322 "backbone" sections are combined with an appropriate promoter and the structural sequence to be expressed. *E. coli* is typically transformed using derivatives of pBR322, a plasmid derived from an *E. coli* species (Bolivar et al., *Gene* 2:95, 1977). pBR322 contains genes for ampicillin and tetracycline resistance and thus provides simple means for identifying transformed cells.

Promoters commonly used in recombinant microbial expression vectors include the β-lactamase (penicillinase) and lactose promoter system (Chang et al., *Nature* 275:615, 1978; and Goeddel et al., *Nature* 281:544, 1979), the tryptophan (trp) promoter system (Goeddel et al., *Nucl. Acids Res* 8:4057, 1980; and EPA 36,776) and tac promoter (Maniatis, *Molecular Cloning: A Laboratory Manual*, Cold Spring Harbor Laboratory, p. 412, 1982). A particularly useful bacterial expression system employs the phage $\lambda$ $P_L$ promoter and cl857ts thermolabile repressor. Plasmid vectors available from the American Type Culture Collection which incorporate derivatives of the $\lambda$ $P_L$ promoter include plasmid pHUB2, resident in *E. coli* strain JMB9 (ATCC 37092) and pPLc28, resident in *E. coli* RR1 (ATCC 53082).

Recombinant IL-4R proteins may also be expressed in yeast hosts, preferably from the Saccharomyces genus, such as *S. cerevisiae*. Yeast of other genera, such as Pichia or Kluyveromyces may also be employed. Yeast vectors will generally contain an origin of replication from the 2μ yeast plasmid or an autonomously replicating sequence (ARS), promoter, DNA encoding IL-4R, sequences for polyadenylation and transcription termination and a selection gene. Preferably, yeast vectors will include an origin of replication and selectable marker permitting transformation of both yeast and *E. coli*, e.g., the ampicillin resistance gene of *E. coli* and *S. cerevisiae* trp1 gene, which provides a selection marker for a mutant strain of yeast lacking the ability to grow in tryptophan, and a promoter derived from a highly expressed yeast gene to induce transcription of a structural sequence downstream. The presence of the trp1 lesion in the yeast host cell genome then provides an effective environment for detecting transformation by growth in the absence of tryptophan.

Suitable promoter sequences in yeast vectors include the promoters for metallothionein, 3-phosphoglycerate kinase (Hitzeman et al., *J. Biol. Chem.* 255:2073, 1980) or other glycolytic enzymes (Hess et al., *J. Adv. Enzyme Reg.* 7:149, 1968; and Holland et al., *Biochem.* 17:4900, 1978), such as enolase, glyceraldehyde-3-phosphate dehydrogenase, hexokinase, pyruvate decarboxylase, phosphofructokinase, glucose-6-phosphate isomerase, 3-phosphoglycerate mutase, pyruvate kinase, triosephosphate isomerase, phosphoglucose isomerase, and glucokinase. Suitable vectors and promoters for use in yeast expression are further described in Hitzeman, EPA 73,657.

Preferred yeast vectors can be assembled using DNA sequences from pBR322 for selection and replication in *E. coli* (Amp$^r$ gene and origin of replication) and yeast DNA sequences including a glucose-repressible ADH2 promoter and α-factor secretion leader. The ADH2 promoter has been described by Russell et al. (*J. Biol. Chem.* 258:2674, 1982) and Beier et al. (*Nature* 300:724, 1982). The yeast α-factor leader, which directs secretion of heterologous proteins, can be inserted between the promoter and the structural gene to be expressed. See, e.g., Kurjan et al., *Cell* 30:933, 1982; and Bitter et al., *Proc. Natl. Acad. Sci. USA* 81:5330, 1984. The leader sequence may be modified to contain, near its 3' end, one or more useful restriction sites to facilitate fusion of the leader sequence to foreign genes.

Suitable yeast transformation protocols are known to those of skill in the art; an exemplary technique is described by Hinnen et al., *Proc. Natl. Acad. Sci. USA* 75:1929, 1978, selecting for Trp$^+$ transformants in a selective medium consisting of 0.67% yeast nitrogen base, 0.5% casamino acids, 2% glucose, 10 μg/ml adenine and 20 μg/ml uracil.

Host strains transformed by vectors comprising the ADH2 promoter may be grown for expression in a rich medium consisting of 1% yeast extract, 2% peptone, and 1% glucose supplemented with 80 μg/ml adenine and 80 μg/ml uracil. Derepression of the ADH2 promoter occurs upon exhaustion of medium glucose. Crude yeast supernatants are harvested by filtration and held at 4° C. prior to further purification.

Various mammalian or insect cell culture systems can be employed to express recombinant protein. Baculovirus systems for production of heterologous proteins in insect cells are reviewed by Luckow and Summers, *Bio/Technology* 6:47 (1988). Examples of suitable mammalian host cell lines include the COS-7 lines of monkey kidney cells, described by Gluzman (*Cell* 23:175, 1981), and other cell lines capable of expressing an appropriate vector including, for example, L cells, C127, 3T3, Chinese hamster ovary (CHO), HeLa and BHK cell lines. Mammalian expression vectors may comprise nontranscribed elements such as an origin of replication, a suitable promoter and enhancer linked to the gene to be expressed, and other 5' or 3' flanking nontranscribed sequences, and 5' or 3' nontranslated sequences, such as necessary ribosome binding sites, a polyadenylation site, splice donor and acceptor sites, and transcriptional termination sequences.

The transcriptional and translational control sequences in expression vectors to be used in transforming vertebrate cells may be provided by viral sources. For example, commonly used promoters and enhancers are derived from Polyoma, Adenovirus 2, Simian Virus 40 (SV40), and human cytomegalovirus. DNA sequences derived from the SV40 viral genome, for example, SV40 origin, early and late promoter, enhancer, splice, and polyadenylation sites may be used to provide the other genetic elements required for expression of a heterologous DNA sequence. The early and late promoters are particularly useful because both are obtained easily from the virus as a fragment which also contains the SV40 viral origin of replication (Fiers et al., *Nature* 273:113, 1978). Smaller or larger SV40 fragments may also be used, provided the approximately 250 bp sequence extending from the Hind III site toward the Bgl I site located in the viral origin of replication is included. Further, mammalian genomic IL-4R promoter, control and/ or signal sequences may be utilized, provided such control sequences are compatible with the host cell chosen. Additional details regarding the use of mammalian high expression vectors to produce a recombinant mammalian IL-4 receptor are provided in Example 8 below. Exemplary vectors can be constructed as disclosed by Okayama and Berg (*Mol. Cell. Biol.* 3:280, 1983).

A useful system for stable high level expression of mammalian receptor cDNAs in C127 murine mammary epithelial cells can be constructed substantially as described by Cosman et al. (*Mol. Immunol.* 23:935, 1986).

A particularly preferred eukaryotic vector for expression of IL-4R DNA is disclosed below in Example 2. This vector, referred to as pCAV/NOT, was derived from the mammalian high expression vector pDC201 and contains regulatory sequences from SV40, adenovirus-2, and human cytomegalovirus. pCAV/NOT containing a human IL-7 receptor insert has been deposited with the American Type Culture Collection (ATCC) under deposit accession number 68014.

Purification of IL-4 Receptors

Purified mammalian IL-4 receptors or analogs are prepared by culturing suitable host/vector systems to express the recombinant translation products of the DNAs of the present invention, and purifying IL-4 receptor from the culture media or cell extracts.

For example, supernatants from systems which secrete recombinant protein into culture media can be first concentrated using a commercially available protein concentration filter, for example, an Amicon or Millipore Pellicon ultrafiltration unit. Following the concentration step, the concentrate can be applied to a suitable purification matrix. For example, a suitable affinity matrix can comprise an IL-4 or lectin or antibody molecule bound to a suitable support. Alternatively, an anion exchange resin can be employed, for example, a matrix or substrate having pendant diethylaminoethyl (DEAE) groups. The matrices can be acrylamide, agarose, dextran, cellulose or other types commonly employed in protein purification. Alternatively, a cation exchange step can be employed. Suitable cation exchangers include various insoluble matrices comprising sulfopropyl or carboxymethyl groups. Sulfopropyl groups are preferred.

Finally, one or more reversed-phase high performance liquid chromatography (RP-HPLC) steps employing hydrophobic RP-HPLC media, e.g., silica gel having pendant methyl or other aliphatic groups, can be employed to further purify an IL-4R composition. Some or all of the foregoing purification steps, in various combinations, can also be employed to provide a homogeneous recombinant protein.

Recombinant protein produced in bacterial culture is usually isolated by initial extraction from cell pellets, followed by one or more concentration, salting-out, aqueous ion exchange or size exclusion chromatography steps. Finally, high performance liquid chromatography (HPLC) can be employed for final purification steps. Microbial cells employed in expression of recombinant mammalian IL-4R can be disrupted by any convenient method, including freeze-thaw cycling, sonication, mechanical disruption, or use of cell lysing agents.

Fermentation of yeast which express mammalian IL-4R as a secreted protein greatly simplifies purification. Secreted recombinant protein resulting from a large-scale fermentation can be purified by methods analogous to those disclosed by Urdal et al. (*J. Chromatog.* 296:171, 1984). This reference describes two sequential, reversed-phase HPLC steps for purification of recombinant human IL-2 on a preparative HPLC column.

Human IL-4R synthesized in recombinant culture is characterized by the presence of non-human cell components, including proteins, in amounts and of a character which depend upon the purification steps taken to recover human IL-4R from the culture. These components ordinarily will be of yeast, prokaryotic or non-human higher eukaryotic origin and preferably are present in innocuous contaminant quantities, on the order of less than about 1 percent by weight. Further, recombinant cell culture enables the production of IL-4R free of proteins which may be normally associated with IL-4R as it is found in nature in its species of origin, e.g. in cells, cell exudates or body fluids.

Administration of Soluble IL-4 Receptor Compositions

The present invention provides methods of using therapeutic compositions comprising an effective amount of soluble IL-4 receptor proteins and a suitable diluent and carrier, and methods for suppressing IL-4-dependent immune responses in humans comprising administering an effective amount of soluble IL-4 receptor protein.

For therapeutic use, purified soluble IL-4 receptor protein is administered to a patient, preferably a human, for treatment in a manner appropriate to the indication. Thus, for example, soluble IL-4 receptor protein compositions administered to suppress immune function can be given by bolus injection, continuous infusion, sustained release from implants, or other suitable technique. Typically, a soluble IL-4 receptor therapeutic agent will be administered in the form of a composition comprising purified protein in conjunction with physiologically acceptable carriers, excipients or diluents. Such carriers will be nontoxic to recipients at the dosages and concentrations employed. Ordinarily, the preparation of such compositions entails combining the IL-4R with buffers, antioxidants such as ascorbic acid, low molecular weight (less than about 10 residues) polypeptides, proteins, amino acids, carbohydrates including glucose, sucrose or dextrins, chelating agents such as EDTA, glutathione and other stabilizers and excipients. Neutral buffered saline or saline mixed with conspecific serum albumin are exemplary appropriate diluents. Preferably, product is formulated as a lyophilizate using appropriate excipient solutions (e.g., sucrose) as diluents. Appropriate dosages can be determined in trials; generally, soluble IL-4 receptor dosages of from about 1 ng/kg/day to about 10 mg/kg/day, more preferably from about 500 ng/kg/day to about 5 mg/kg/day, and most preferably from about 5 ug/kg/day to about 2 mg/kg/day, are appropriate for inducing a biological effect. The amount and frequency of administration will depend, of course, on such factors as the nature and severity of the indication being treated, the desired response, the condition of the patient, and so forth.

Soluble IL-4R proteins are administered for the purpose of inhibiting IL-4 dependent responses, such as suppressing immune responses in a human. A variety of diseases or conditions are caused by IL-4 dependent immune responses as determined by the ability of sIL-4R to inhibit the response. Soluble IL-4R compositions may be used, for example, to regulate the function of B cells. Soluble IL-4R inhibits IL-4 dependent B cell proliferation and isotype specific (IgGl and IgE) secretions. sIL-4R may therefore be used to suppress IgE antibody formation in the treatment of IgE-induced immediate hypersensitivity reactions, such as allergic rhinitis (common hay fever), bronchial asthma, atopic dermatitis and gastrointestinal food allergy.

sIL-4R compositions may also be used to regulate the function of T cells. Although T cell dependent functions were formerly thought to be mediated principally by IL-2, recent studies have shown that under some circumstances T cell growth and proliferation can be mediated by growth factors such as IL-4. Examples 20 through 23 below, for example, indicate that sIL-4R suppresses or inhibits T-cell dependent responses to alloantigen. A variety of diseases or conditions are caused by an immune response to alloantigen, including allograft rejection and graft-versus-host reaction. In alloantigen-induced immune responses, sIL-4R suppresses lymphoproliferation and inflammation which result upon activation of T cells. sIL-4R has therefore been shown to be potentially effective in the clinical treatment of, for example, rejection of allografts (such as skin, kidney, heart, lung liver and pancreas transplants), and graft-versus-host reactions in patients who have received bone marrow transplants.

sIL-4R may also be used in clinical treatment of autoimmune dysfunctions, such as rheumatoid arthritis, diabetes, which are dependent upon the activation of T cells against antigens not recognized as being indigenous to the host.

Because of the primary role IL-2 plays in the proliferation and differentiation of T cells, combination therapy using both IL-4 and IL-2 may be used in the treatment of T cell dependent dysfunctions. Use in conjunction with other soluble cytokine receptors, e.g., IL-1 receptor, is also contemplated.

The following examples are offered by way of illustration, and not by way of limitation.

EXAMPLES

Example 1

Binding assays for IL-4 receptor

A. Radiolabeling of IL-4. Recombinant murine and human IL-4 were expressed in yeast and purified to homogeneity as described by Park, et al., *Proc. Natl. Acad. Sci. USA* 84:5267 (1987) and Park et al., *J. Exp. Med.* 166:476 (1987), respectively. The purified protein was radiolabeled using a commercially available enzymobead radioiodination reagent (BioRad). In this procedure 2.5 μg rIL-4 in 50 μl 0.2M sodium phosphate, pH 7.2 are combined with 50 μl enzymobead reagent, 2 MCi of sodium iodide in 20 μl of 0.05M sodium phosphate pH 7.0 and 10 μl of 2.5% b-D-glucose. After 10 min at 25° C., sodium azide (10 μl of 50 mM) and sodium metabisulfite (10 μl of 5 mg/ml) were added and incubation continued for 5 min. at 25° C. The reaction mixture was fractionated by gel filtration on a 2 ml bed volume of Sephadex® G-25 (Sigma) equilibrated in Roswell Park Memorial Institute (RPMI) 1640 medium containing 2.5% (w/v) bovine serum albumin (BSA), 0.2% (w/v) sodium azide and 20 mM Hepes pH 7.4 (binding medium). The final pool of $^{125}$I-IL-4 was diluted to a working stock solution of $2 \times 10^{-8}$M in binding medium and stored for up to one month at 4° C. without detectable loss of receptor binding activity. The specific activity is routinely in the range of $1-2 \times 10^{16}$ cpm/mmole IL-4.

B. Binding to Adherent Cells. Binding assays done with cells grown in suspension culture (i.e., CTLL and CTLL-19.4) were performed by a phthalate oil separation method (Dower et al., *J. Immunol.* 132:751, 1984) essentially as described by Park et al., *J. Biol. Chem.* 261:4177, 1986 and Park et al., supra. Binding assays were also done on COS cells transfected with a mammalian expression vector containing cDNA encoding an IL-4 receptor molecule. For Scatchard analysis of binding to adherent cells, COS cells were transfected with plasmid DNA by the method of Luthman et al., *Nucl. Acids. Res.* 11:1295, 1983, and McCutchan et al., *J. Natl. Cancer Inst.* 41:351, 1968. Eight hours following transfection, cells were trypsinized, and reseeded in six well plates (Costar, Cambridge, Mass.) at a density of $1 \times 10^4$ COS-IL-4 receptor transfectants/well mixed with $5 \times 10^5$ COS control transfected cells as carriers. Two days later monolayers were assayed for $^{125}$I-IL-4 binding at 4° C. essentially by the method described by Park et al., *J. Exp. Med.* 166:476, 1987. Nonspecific binding of $^{125}$I-IL-4 was measured in the presence of a 200-fold or greater molar excess of unlabeled IL-4. Sodium azide (0.2%) was included in all binding assays to inhibit internalization of $^{125}$I-IL-4 by cells at 37° C.

For analysis of inhibition of binding by soluble IL-4R, supernatants from COS cells transfected with recombinant IL-4R constructs were harvested three days after transfection. Serial two-fold dilutions of conditioned media were pre-incubated with $3 \times 10^{-10}$M $^{125}$I-IL-4 (having a specific activity of about $1 \times 10^{16}$ cpm/mmol) for one hour at 37° C. prior to the addition of $2 \times 10^6$ CTLL cells. Incubation was continued for 30 minutes at 37° C. prior to separation of free and cell-bound murine $^{125}$I-IL-4.

C. Solid Phase Binding Assays. The ability of IL-4 receptor to be stably adsorbed to nitrocellulose from detergent extracts of CTLL 19.4 cells yet retain IL-4 binding activity provided a means of monitoring purification. One ml aliquots of cell extracts (see Example 3), IL-4 affinity column fractions (see Example 4) or other samples are placed on dry BA85/21 nitrocellulose membranes (Schleicher and Schuell, Keene, N.H.) and allowed to dry. The membranes are incubated in tissue culture dishes for 30 minutes in Tris (0.05M) buffered saline (0.15M) pH 7.5 containing 3% w/v BSA to block nonspecific binding sites. The membrane is then covered with $4 \times 10^{-11}$M $^{125}$I-IL-4 in PBS+3% BSA with or without a 200 fold molar excess of unlabeled IL-4 and incubated for 2 hr at 4° C. with shaking. At the end of this time, the membranes are washed 3 times in PBS, dried and placed on Kodak X-Omat™ AR film for 18 hr at −70° C.

Example 2

Selection of CTLL cells with high IL-4 receptor expression by fluorescence activated cell sorting (FACS)

The preferred cell line for obtaining high IL-4 receptor selection is CTLL, a murine IL-2 dependent cytotoxic T cell line (ATCC TIB 214) which typically exhibits 2,000 to 5,000 IL-4 receptors per cell and responds to IL-4 by short-term proliferation. To obtain higher levels of IL-4 receptor expression, CTLL cells (parent cells) were subjected to multiple rounds of fluorescence-activated cell sorting with labeled IL-4. A highly fluorescent derivative of IL-4 was derived by conjugating rmIL-4 fluorescein hydrazide to periodate oxidized sugar moieties of IL-4 which was produced in yeast as described by Park et al., *Proc. Natl. Acad. Sci. USA* 84:1669 (1987). The fluorescein-conjugated IL-4 was prepared by combining aliquots of hyperglycosylated rmIL-4 (300 μg in 300 μl of 0.1M citrate-phosphate buffer, pH 5.5) with 30 μl of 10 mM sodium m-periodate (Sigma), freshly prepared in 0.1M citrate-phosphate, pH 5.5 and the mixture incubated at 4° C. for 30 minutes in the dark. The reaction was quenched with 30 μl of 0.1M glycerol and dialyzed for 18 hours at 4° C. against 0.1M citrate-phosphate pH 5.5. Following dialysis, a 1/10 volume of 100 mM 5-(((2-(carbohydrazino)methyl)thio)acetyl)-aminofluorescein (Molecular Probes, Eugene Oreg.) dissolved in DMSO was added to the sample and incubated at 25° C. for 30 minutes. The IL-4-fluorescein was then exhaustively dialyzed at 4° C. against PBS, pH 7.4 and protein concentration determined by amino acid analysis. The final product was stored at 4° C. following the addition of 1% (w/v) BSA and sterile filtration.

CTLL cells ($5 \times 10^6$) were then incubated for 30 min at 37° C. in 150 μl PBS+1% BSA containing $1 \times 10^{-9}$M IL-4-fluorescein under sterile conditions. The mixture was then chilled to 4° C., washed once in a large volume of PBS+1% BSA and sorted using an EPICS® C flow cytometer (Coulter Instruments). The cells providing the highest level fluorescence signal (top 1.0%) were collected in bulk and the population expanded in liquid cell culture and subjected to additional rounds of sorting as described below. Alternatively, for single cell cloning, cells exhibiting a fluorescence signal in the top 1.0% were sorted into 96 well tissue culture microtiter plates at 1 cell per well.

Progress was monitored by doing binding assays with $^{125}$I-IL-4 following each round of FACS selection. Unsorted CTLL cells (CTLL parent) typically exhibited 1000–2000 IL-4 receptors per cell. CTLL cells were subjected to 19 rounds of FACS selection. The final CTLL cells selected (CTLL-19) exhibited $5 \times 10^5$ to $1 \times 10^6$ IL-4 receptors per cell. At this point the CTLL-19 population was subjected to EPICS® C-assisted single cell cloning and individual clonal populations were expanded and tested for $^{125}$I-IL-4 binding. A single clone, designated CTLL-19.4, exhibited $1 \times 10^6$ IL-4 receptors per cell and was selected for purification and cloning studies. While the calculated apparent $K_a$ values are similar for the two lines, CTLL-19.4 expresses approximately 400-fold more receptors on its surface than does the CTLL parent.

Example 3

Detergent extraction of CTLL cells

CTLL 19.4 cells were maintained in RPMI 1640 containing 10% fetal bovine serum, 50 U/ml penicillin, 50 µg/ml streptomycin and 10 ng/ml of recombinant human IL-2. Cells were grown to $5 \times 10^5$ cells/ml in roller bottles, harvested by centrifugation, washed twice in serum free DMEM and segmented at 2000×g for 10 minutes to form a packed pellet (about $2 \times 10^8$ cells/ml). To the pellet was added an equal volume of PBS containing 1% Triton® X-100 and a cocktail of protease inhibitors (2 mM phenylmethysulfonylfluoride, 10 µM pepstatin, 10 µM leupeptin, 2 mM o-phenanthroline and 2 mM EGTA). The cells were mixed with the extraction buffer by vigorous vortexing and the mixture incubated on ice for 20 minutes after which the mixture was centrifuged at 12,000×g for 20 minutes at 8° C. to remove nuclei and other debris. The supernatant was either used immediately or stored at –70° C. until use.

Example 4

IL-4 receptor purification by IL-4 affinty chromatography

In order to obtain sufficient quantities of murine IL-4R to determine its N-terminal sequence or to further characterize human IL-4R, protein obtained from the detergent extraction of cells was further purified by affinity chromatography. Recombinant murine or human IL-4 was coupled to Affigel®-10 (BioRad) according to the manufacturer's suggestions. For example, to a solution of IL-4 (3.4 mg/ml in 0.4 ml of 0.1M Hepes pH 7.4) was added 1.0 ml of washed Affigel®-10. The solution was rocked overnight at 4° C. and an aliquot of the supernatant tested for protein by a BioRad protein assay per the manufacturer's instructions using BSA as a standard. Greater than 95% of the protein had coupled to the gel, suggesting that the column had a final load of 1.3 mg IL-4 per ml gel. Glycine ethyl ester was added to a final concentration of 0.05M to block any unreacted sites on the gel. The gel was washed extensively with PBS-1% Triton® followed by 0.1 Glycine-HCl, pH 3.0. A 0.8×4.0 cm column was prepared with IL-4-coupled Affigel® prepared as described (4.0 ml bed volume) and washed with PBS containing 1% Triton® X-100 for purification of murine IL-4R. Alternatively, 50 µl aliquots of 20% suspension of IL-4-coupled Affigel® were incubated with $^{35}$S-cysteine/methionine-labeled cell extracts for small-scale affinity purifications and gel electrophoresis.

Aliquots (25 ml) of detergent extracted IL-4 receptor bearing CTLL 19.4 cells were slowly applied to the murine IL-4 affinity column at 4° C. (flow rate of 3.0 ml/hr). The column was then washed sequentially with PBS containing 1% Triton® X-100, RIPA buffer (0.05M Tris, 0.15M NaCl, 1% NP-40, 1% deoxycholate and 0.1% SDS), PBS containing 0.1% Triton® X-100 and 10 mM ATP, and PBS with 1% Triton® X-100 to remove all contaminating material except the mIL-4R. The column was then eluted with pH 3.0 glycine HCl buffer containing 0.1% Triton® X-100 to remove the IL-4R and washed subsequently with PBS containing 0.1% Triton® X-100. One milliliter fractions were collected for the elution and 2 ml fractions collected during the wash. Immediately following elution, samples were neutralized with 80 µl of 1M Hepes, pH 7.4. The presence of receptor in the fractions was detected by the solid phase binding assay as described above, using $^{125}$I-labeled IL-4. Aliquots were removed from each fraction for analysis by SDS-PAGE and the remainder frozen at –70° C. until use. For SDS-PAGE, 40 µl of each column fraction was added to 40 µl of 2×SDS sample buffer (0.125M Tris HCl pH 6.8, 4% SDS, 20% glycerol, 10% 2-mercaptoethanol). The samples were placed in a boiling water bath for 3 minutes and 80 µl aliquots applied to sample wells of a 10% polyacrylamide gel which was set up and run according to the method of Laemmli (*Nature* 227:680, 1970). Following electrophoresis, gels were silver stained as previously described by Urdal et al. (*Proc. Natl. Acad. Sci. USA* 81:6481, 1984).

Purification by the foregoing process permitted identification by silver staining of polyacrylamide gels of two mIL-4R protein bands averaging 45–55 kDa and 30–40 kDa that were present in fractions exhibiting IL-4 binding activity. Experiments in which the cell surface proteins of CTLL-19.4 cells were radiolabeled and $^{125}$I-labeled receptor was purified by affinity chromatography suggested that these two proteins were expressed on the cell surface. The ratio of the lower to higher molecular weight bands increased upon storage of fractions at 4° C., suggesting a precursor product relationship, possibly due to slow proteolytic degradation. The mIL-4 receptor protein purified by the foregoing process remains capable of binding IL-4, both in solution and when adsorbed to nitrocellulose.

Example 5

Sequencing of IL-4 receptor protein

CTLL 19.4 mIL-4 receptor containing fractions from the mIL-4 affinity column purification were prepared for amino terminal protein sequence analysis by fractionating on an SDS-PAGE gel and then transferred to a PVDF membrane. Prior to running the protein fractions on polyacrylamide gels, it was first necessary to remove residual detergent from the affinity purification process. Fractions containing proteins bound to the mIL-4 affinity column from three preparations were thawed and concentrated individually in a speed vac under vacuum to a final volume of 1 ml. The concentrated fractions were then adjusted to pH 2 by the addition of 50% (v/v) TFA and injected onto a Brownlees RP-300 reversed-phase HPLC column (2.1×30 mm) equilibrated with 0.1% (v/v) TFA in $H_2O$ at a flow rate of 200 µl/min running on a Hewlett Packard Model 1090M HPLC. The column was washed with 0.1% TFA in $H_2O$ for 20 minutes post injection. The HPLC column containing the bound protein was then developed with a gradient as follows:

| Time | % Acetonitrile in 0.1% TFA |
|---|---|
| 0 | 0 |
| 5 | 30 |
| 15 | 30 |
| 25 | 70 |
| 30 | 70 |
| 35 | 100 |
| 40 | 0 |

1 ml fractions were collected every five minutes and analyzed for the presence of protein by SDS PAGE followed by silver staining.

Each fraction from the HPLC run was evaporated to dryness in a speed vac and then resuspended in Laemmli reducing sample buffer, prepared as described by Laemmli, U.K. Nature 227:680, 1970. Samples were applied to a 5–20% gradient Laemmli SDS gel and run at 45 mA until the dye front reached the bottom of the gel. The gel was then transferred to PVDF paper and stained as described by Matsudaira, J. Biol. Chem. 262:10035, 1987. Staining bands were clearly identified in fractions from each of the three preparations at approximately 30,000 to 40,000 $M_r$.

The bands from the previous PVDF blotting were excised and subjected to automated Edman degradation on an Applied Biosystems Model 477A Protein Sequencer essentially as described by March et al. (Nature 315:641, 1985), except that PTH amino acids were automatically injected and analyzed on line with an Applied Biosystems Model 120A HPLC using a gradient and detection system supplied by the manufacturer. The following amino terminal sequence was determined from the results of sequencing: NH$_2$-Ile-Lys-Val-Leu-Gly-Glu-Pro-Thr-(Cys/Asn)-Phe-Ser-Asp-Tyr-Ile. Position 9 was assigned as a cysteine or glycosylated asparagine owing to the lack of an observable PTH-amino acid signal in the cycle. The bands from the second preparation used for amino terminal sequencing were treated with CNBr using the in situ technique described by March et al. (Nature 315:641, 1985) to cleave the protein after internal methionine residues. Sequencing of the resulting cleavage products yielded the following data, indicating that the CNBr cleaved the protein after two internal methionine residues:

| Cycle | Residues Observed |
|-------|------------------|
| 1 | Val, Ser |
| 2 | Gly, Leu |
| 3 | Ile, Val |
| 4 | Tyr, Ser |
| 5 | Arg, Tyr |
| 6 | Glu, Thr |
| 7 | Asp, Ala |
| 8 | Asn, Leu |
| 9 | Pro, Val |
| 10 | Ala |
| 11 | Glu, Val |
| 12 | Phe, Gly |
| 13 | Ile, Asn |
| 14 | Val, Gln |
| 15 | Tyr, Ile |
| 16 | Lys, Asn |
| 17 | Val, Thr |
| 18 | Thr, Gly |

When compared with the protein sequences derived from clones 16 and 18 (see FIG. 2), the sequences matched as follows:

The above data support the conclusion that clones 16 and 18 are derived from the message for the IL-4 receptor.

Example 6

Synthesis of hybrid-subtracted cDNA probe

In order to screen a library for clones encoding a murine IL-4 receptor, a highly enriched IL-4 receptor cDNA probe was obtained using a subtractive hybridization strategy. Polyadenylated (polyA$^+$) mRNA was isolated from two similar cell lines, the parent cell line CTLL (which expresses approximately 2,000 receptors per cell) and the sorted cell line CTLL 19.4 (which expresses 1×10$^6$ receptors per cell). The mRNA content of these two cell lines is expected to be identical except for the relative level of IL-4 receptor mRNA. A radiolabeled single-stranded cDNA preparation was then made from the mRNA of the sorted cell line CTLL 19.4 by reverse transcription of polyadenylated mRNA from CTLL 19.4 cells by a procedure similar to that described by Maniatis et al., Molecular Cloning, A Laboratory Manual (Cold Spring Harbor Laboratory, New York, 1982). Briefly, polyA$^+$ mRNA was purified as described by March et al. (Nature 315:641–647, 1985) and copied into cDNA by reverse transcriptase using oligo dT as a primer. To obtain a high level of $^{32}$P-labeling of the cDNA,100 μCi of $^{32}$P-dCTP (s.a.=3000 Ci/mmol) was used in a 50 μl reaction with non-radioactive dCTP at 10 μM. After reverse transcription at 42° C. for 2 hours, EDTA was added to 20 mM and the RNA was hydrolyzed by adding NaOH to 0.2M and incubating the cDNA mixture at 68° C. for 20 minutes. The single-stranded cDNA was extracted with a phenol/chloroform (50/50) mixture previously equilibrated with 10 mM Tris-Cl, 1 mM EDTA. The aqueous phase was removed to a clean tube and made alkaline again by the addition of NaOH to 0.5M. The cDNA was then size-fractionated by chromatography on a 6 ml Sephadex® G50 column in 30 mM NaOH and 1 mM EDTA to remove small molecular weight contaminants.

The resulting size-fractionated cDNA generated from the sorted CTLL 19.4 cells was then hybridized with an excess of mRNA from the unsorted parental CTLL cells by ethanol-precipitating the cDNA from CTLL 19.4 cells with 30 μg of polyA$^+$ mRNA isolated from unsorted CTLL cells, resuspending in 16 μl of 0.25M NaPO$_4$, pH 6.8, 0.2% SDS, 2 mM EDTA and incubating for 20 hours at 68° C. The cDNAs from the sorted CTLL 19.4 cells that are complementary to mRNAs from the unsorted CTLL cells form double stranded cDNA/mRNA hybrids, which can then be separated from the single stranded cDNA based on their different binding affinities on hydroxyapatite. The mixture was diluted with 30 volumes of 0.02M NaPO$_4$, pH 6.8, bound to hydroxya-

```
                    1              5               10              15      18
Sequence 1: (Met)—Val—Asn—Ile—Ser—Arg—Glu—Asp—Asn—Pro—Ala—Glu—Phe—Ile—Val—Tyr—Asn—Val—Thr 1              5               10              15      18
Sequence 2: (Met)—Ser—Gly—Val—Tyr—Tyr—Thr—Ala—Arg—Val—Arg—Val—Arg—Ser—Gln—Ile—Leu—Thr—Gly
```

Identical matches were found for all positions of sequence 1 except Asn(2) and sequence 2, except Arg at positions 8, 10, and 12, Ser at position 13, and Leu at position 16. The above sequences correspond to amino acid residues 137–154 and 169–187 of FIG. 2A.

In addition, the amino terminal sequence matched a sequence derived from the clone with position 9 being defined as a Cys.

patite at room temperature, and single-stranded cDNA was then eluted from the resin with 0.12M NaPO$_4$, pH 6.8, at 60° C., as described by Sims et al., Nature 312:541, 1984. Phosphate buffer was then removed by centrifugation over 2 ml Sephadex® G50 spin columns in water. This hybrid subtraction procedure removes a majority of common sequences between CTLL 19.4 and unsorted CTLL cells, and leaves a single-stranded cDNA pool enriched for radiolabeled IL-4 receptor cDNA which can be used to probe a cDNA library (as described below).

Example 7

Synthesis of cDNA library and plaque screening

A cDNA library was constructed from polyadenylated mRNA isolated from CTLL 19.4 cells using standard techniques (Gubler, et al., *Gene* 25:263, 1983; Ausubel et al., eds., *Current Protocols in Molecular Biology*, Vol. 1, 1987). After reverse transcription using oligo dT as primer, the single-stranded cDNA was rendered double-stranded with DNA polymerase I, blunt-ended with T4 DNA polymerase, methylated with EcoR I methylase to protect EcoR I cleavage sites within the cDNA, and ligated to EcoR I linkers. The resulting constructs were digested with EcoR I to remove all but one copy of the linkers at each end of the cDNA, and ligated to an equimolar concentration of EcoR I cut and dephosphorylated λZAP® arms and the resulting ligation mix was packaged in vitro (Gigapack®) according to the manufacturer's instructions. Other suitable methods and reagents for generating cDNA libraries in λ phage vectors are described by Huynh et al., *DNA Cloning Techniques: A Practical Approach*, IRL Press, Oxford (1984); Meissner et al., *Proc. Natl. Acad. Sci. USA* 84:4171 (1987), and Ausubel et al., supra. λZAP® is a phage λ cloning vector similar to λgt11 (U.S. Pat. No. 4,788,135) containing plasmid sequences from pUC19 (Norrander et al., *Gene* 26:101, 1987), a polylinker site located in a lacZ gene fragment, and an f1 phage origin of replication permitting recovery of ssDNA when host bacteria are superinfected with f1 helper phage. DNA is excised in the form of a plasmid comprising the foregoing elements, designated Bluescript®. Gigapack® is a sonicated *E. coli* extract used to package λ phage DNA. λZAP®, Bluescript®, and Gigapack® are registered trademarks of Stratagene, San Diego, Calif., USA.

The radiolabeled hybrid-subtracted cDNA from Example 6 was then used as a probe to screen the cDNA library. The amplified library was plated on BB4 cells at a density of 25,000 plaques on each of 20 150 mm plates and incubated overnight at 37° C. All manipulations of λZAP® and excision of the Bluescript® plasmid were as described by Short et al., (*Nucl. Acids Res.* 16:7583, 1988) and Stratagene product literature. Duplicate plaque lift filters were incubated with hybrid-subtracted cDNA probes from Example 6 in hybridization buffer containing 50% formamide, 5×SSC, 5×Denhardt's reagent and 10% dextran sulfate at 42° C. for 48 hours as described by Wahl et al., *Proc. Natl. Acad. Sci. USA* 76:3683, 1979. Filters were then washed at 68° C. in 0.2×SSC. Sixteen positive plaques were purified for further analysis.

Bluescript® plasmids containing the cDNA inserts were excised from the phage as described by the manufacturer and transformed into *E. coli*. Plasmid DNA was isolated from individual colonies, digested with EcoR I to release the cDNA inserts and electrophoresed on standard 1% agarose gels. Four duplicate gels were blotted onto nylon filters to produce identical Southern blots for analysis with various probes which were (1) radiolabeled cDNA from unsorted CTLL cells, (2) radiolabeled cDNA from CTLL 19.4 sorted cells, (3) hybrid subtracted cDNA from CTLL 19.4 sorted cells, and (4) hybrid subtracted cDNA from CTLL 19.4 sorted cells after a second round of hybridization to poly A$^+$ mRNA from an IL-4 receptor negative mouse cell line (LBRM 33 1A5B6). These probes were increasingly enriched for cDNA copies of mRNA specific for the sorted cell line CTLL 19.4. Of the 16 positive plaques isolated from the library, four clones (11A,14,16 and 18) showed a parallel increase in signal strength with enrichment of the probe.

Restriction mapping (shown in FIG. 1) and DNA sequencing of the isolated CTLL clones indicated the existence of at least two distinct mRNA populations. Both mRNA types have homologous open reading frames over most of the coding region yet diverge at the 3' end, thus encoding homologous proteins with different COOH-terminal sequences. DNA sequence from inside the open reading frames of both clones code for protein sequence that is identical to protein sequence derived from sequencing of the purified IL-4 receptor described in more detail in Example 5. Clone 16 and clone 18 were used as the prototypes for these two distinct message types. Clone 16 contains an open reading frame that encodes a 258-amino acid polypeptide which includes amino acids −25 to 233 of FIG. 2A. Clone 18 encodes a 230-amino acid soluble receptor protein, the N-terminal 224 amino acids of which are identical to the N-terminus of clone 16 but diverge 9 amino acids upstream of the putative transmembrane region beginning with nucleotide number 598. This insertion adds the 3' nucleotide sequence CCAAGTAATGAAAATCTG which encodes the C-terminal 6 amino acids, Pro-Ser-Asn-Glu-Asn-Leu, followed by a termination codon TGA. Both clones were expressed in a mammalian expression system, as described in Example 8.

Example 8

Expression of IL-4R in mammalian cells

Figure 3:
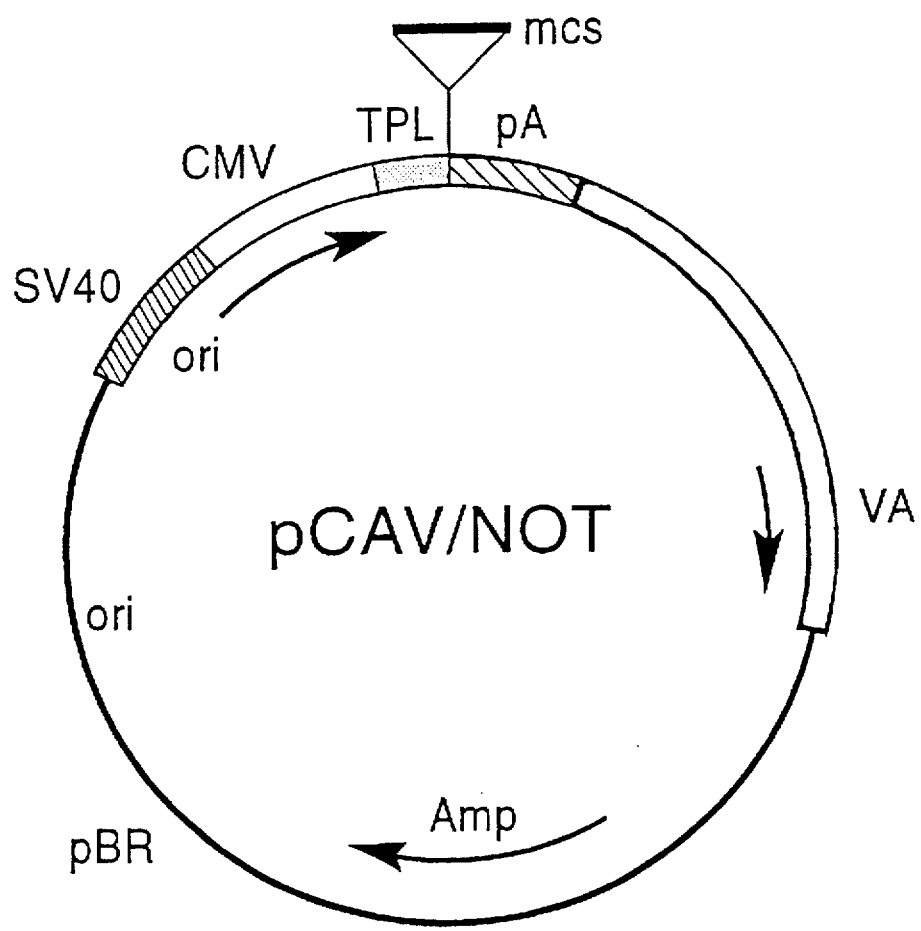
FIG. 3 is a schematic illustration of the mammalian high expression plasmid pCAV/NOT, which is described in greater detail in Example 8.

A. Expression in COS-7 Cells. A eukaryotic expression vector pCAV/NOT, shown in FIG. 3, was derived from the mammalian high expression vector pDC201, described by Sims et al., *Science* 241:585, 1988). pDC201 is a derivative of pMLSV, previously described by Cosman et al., *Nature* 312:768, 1984. pCAV/NOT is designed to express cDNA sequences inserted at its multiple cloning site (MCS) when transfected into mammalian cells and includes the following components: SV40 (hatched box) contains SV40 sequences from coordinates 5171-270 including the origin of replication, enhancer sequences and early and late promoters. The fragment is oriented so that the direction of transcription from the early promoter is as shown by the arrow. CMV contains the promoter and enhancer regions from human cytomegalovirus (nucleotides −671 to +7 from the sequence published by Boshart et al., *Cell* 41:521–530, 1985). The tripartite leader (stippled box) contains the first exon and part of the intron between the first and second exons of the adenovirus-2 tripartite leader, the second exon and part of the third exon of the tripartite leader and a multiple cloning site (MCS) containing sites for Xho I, Kpn I, Sma I, Not I and Bgl II. pA (hatched box) contains SV40 sequences from 4127-4100 and 2770-2533 that include the polyadenylation and termination signals for early transcription. Clockwise from pA are adenovirus-2 sequences 10532-11156 containing the VAI and VAII genes (designated by a black bar), followed by pBR322 sequences (solid line) from 4363-2486 and 1094-375 containing the ampicillin resistance gene and origin of replication. The resulting expression vector was designated pCAV/NOT.

Inserts in clone 16 and clone 18 were both released from Bluescript® plasmid by digestion with Asp 718 and Not I. The 3.5 kb insert from clone 16 was then ligated directly into the expression vector pCAV/NOT also cut at the Asp 718 and Not I sites in the polylinker region. The insert from clone 18 was blunt-ended with T4 polymerase followed by ligation into the vector pCAV/NOT cut with Sma I and dephosphorylated.

Plasmid DNA from both IL-4 receptor expression plasmids were used to transfect a sub-confluent layer of monkey COS-7 cells using DEAE-dextran followed by chloroquine treatment, as described by Luthman et al. (*Nucl. Acids Res.* 11:1295, 1983) and McCutchan et al. (*J. Natl. Cancer Inst.* 41:351, 1968). The cells were then grown in culture for three days to permit transient expression of the inserted sequences. After three days, cell culture supernatants and the cell monolayers were assayed (as described in Example 1) and IL-4 binding was confirmed.

B. Expression in CHO Cells. IL-4R was also expressed in the mammalian CHO cell line by first ligating an Asp718/NotI restriction fragment of clone 18 into the pCAV/NOT vector as described in Example 8. The pCAV/NOT vector containing the insert from cone 18 was then co-transfected using a standard calcium phosphate method into CHO cells with the dihydrofolate reductase (DHFR) cDNA selectable marker under the control of the SV40 early promoter. The DHFR sequence enables methotrexate selection for mammalian cells harboring the plasmid. DHFR sequence amplification events in such cells were selected using elevated methotrexate concentrations. In this way, the contiguous DNA sequences are also amplified and thus enhanced expression is achieved. Mass cell cultures of the transfectants secreted active soluble IL-4R at approximately 100 ng/ml.

C. Expression in HeLa Cells. IL-4R was expressed in the human HeLa-EBNA cell line 653-6, which constitutively expresses EBV nuclear antigen-1 driven from the CMV immediate-early enhancer/promoter. The expression vector used was pHAV-EO-NEO, described by Dower et al., *J. Immunol.* 142:4314, 1989), a derivative of pDC201, which contains the EBV origin of replication and allows high level expression in the 653-6 cell line. pHAV-EO-NEO is derived from pDC201 by replacing the adenovirus major late promoter with synthetic sequences from HIV-1 extending from –148 to +78 relative to the cap site of the viral mRNA, and including the HIV-1 tat gene under the control of the SV-40 early promoter. It also contains a Bgl II-Sma I fragment containing the neomycin resistance gene of pSV2NEO (Southern & Berg, *J. Mol. Appl. Genet.* 1:332, 1982) inserted into the Bgl II and Hpa I sites and subcloning downstream of the Sal I cloning site. The resulting vector permits selection of transfected cells for neomycin resistance.

A 760 bp IL-4R fragment of clone C-18 from the CTLL 19.4 library was released from the Bluescript® plasmid of the λZAP® cloning system (Stratagene, San Diego, Calif., USA) by digesting with EcoN I and Sst I restriction enzymes. This fragment of clone C-18 corresponds to the nucleotide sequence set forth in FIG. 2, with the addition of a 5' terminal nucleotide sequence of TGCAGGCACCTTTTGTGTCCCCA, a TGA stop codon which follows nucleotide 615 of FIG. 2A, and a 3' terminal nucleotide sequence of CTGAGTGACCTTGGGGGCT-GCGGTGGTGAGGAGAGCT. This fragment was then blunt-ended using T4 polymerase and subcloned into the Sal I site of pHAV-EO-NEO. The resulting plasmid was then transfected into the 653-6 cell line by a modified polybrene transfection method as described by Dower et al. (*J. Immunol.* 142:4314, 1989) or by electroporation with the exception that the cells were trypsinized at 2 days post-transfection and split at a ratio of 1:8 into media containing G418 (Gibco Co.) at a concentration of 1 mg/ml. Culture media were changed twice weekly until neomycin-resistant colonies were established. Colonies were then either picked individually using cloning rings, or pooled together, to generate mass cultures. These cell lines were maintained under drug selection at a G418 concentration of 250 ug/ml.

In an effort to select cell colonies expressing high levels of soluble IL-4 receptor, a membrane filter assay was set up as follows. High expressing cell clones were isolated by seeding 450 HeLa IL-4R transfectant cells in a 20 cm plate and allowing the cells to grow for 10 days. Cell monolayers were then washed with a Tris-buffered saline (TBS) solution and overlayed with a nitrocellulose membrane. The overlay technique is essentially that of McCracken and Brown, *Biotechniques* 2:82, 1984, except that the nitrocellulose was overlayed with small glass beads to ensure that the membrane was kept flat. Cells were incubated for an additional 24 hours to allow secretion and adsorption of soluble IL-4 receptor to the nitrocellulose membrane. Finally the membrane was removed, washed gently in TBS containing 1% bovine serum albumin (BSA) for 30 minutes at room temperature, then incubated in TBS with 3% BSA containing $^{125}$I-IL-4 ($4\times10^{-11}$M, specific activity ~$1\times10^{16}$ cpm/mmol) for hours at 4° C. Membranes were then washed 3 times with PBS, dried and exposed on Kodak X-omat™ film overnight at –70° C.

The developed film showed spots aligned with cells growing on the plates in culture. Cell colonies aligned with the darkest spots on the film (indicating the highest level of IL-4 receptor production by cells) were harvested, and grown up in culture. When the individual clones reached confluency, supernatants were tested for the presence of soluble IL-4 receptor in a binding inhibition assay as follows. Inhibition assays were performed by first incubating various concentrations of unlabeled IL-4 or soluble IL-4 receptor with 50 ul of $^{125}$I-IL-4 ($1.65\times10^{-10}$M) for thirty minutes at 37° C. in binding medium (RPMI with 2.5% BSA, 0.2% sodium azide, 0.2% M Hepes, pH 7.4). Subsequently $2\times10^6$ CTLL-2 cells were added in 50 ul of binding medium and the incubation continued for an additional thirty minutes. Free and cell-bound $^{125}$I-IL-4 were then separated by the pthalate oil separation method (Dower, S. K. et al., *J. Immunol.* 132:751, 1984). Percent specific inhibition was calculated using incubation of $^{125}$I-IL-4 with excess unlabeled IL-4 ($4\times10^{-9}$M) as a positive control and 50 ul of binding medium as a negative control. The binding data were calculated and graphed using RS/1 (BBN Software Products, Cambridge, Mass.) as previously described (Dower, S. K. et al., *J. Exp. Med* 162:501, 1985).

Initial cultures of cells produced ~100–600 ng/ml of soluble IL-4R protein, and several cell clones isolated with the membrane-trapping technique produced as much as 2–3 ug/ml of IL-4R protein. These cell lines are currently maintained under drug selection in G418 at a concentration of 250 ug/ml. The establishment of a stable cell clone, HeLa E3C3, producing soluble IL-4R enabled us to begin scaling up production and purification of the soluble recombinant IL-4 receptor. For soluble IL-4 receptor production, the HeLa E3C3 cells were seeded in expanded surface area roller bottles (1:20 split ratio), and were grown for four days with 250 ml of modified Dulbecco's Eagles medium, 5% fetal bovine serum and 1% penicillin, streptomycin and glutamine. Roller bottles were then switched to serum free media (300 ml/roller bottle) for three days. Soluble IL-4 receptor protein was purified from HeLa E3C3 culture supernatants by affinity chromatography on IL-4 linked to Affigel-10. Recombinant murine IL-4 was coupled to Affigel®-10 (BioRad) according to the manufacturer's suggestions. Briefly, 1.0 ml of washed Affigel®-10 was added to a solution of IL-4 (3.4 mg/ml in 0.4 ml of 0.1M Hepes pH 7.4). The solution was rocked overnight at 4° C. and an aliquot of the supernatant tested for protein by a BioRad protein assay per the manufacturer's instructions using BSA as a standard. Greater than 95% of the protein had coupled to the gel, suggesting that the column had a final load of 1.3 mg IL-4 per ml gel. Glycine ethyl ester was added to a final concentration of 0.05M to block any unreacted sites on the gel. The gel was washed extensively with PBS-1% Triton® followed by 0.1 Glycine-HCl, pH 3.0. A 0.8×4.0 cm column was prepared with IL-4-coupled Affigel® prepared as described (4.0 ml bed volume) and washed with PBS containing 1% Triton® X-100 for purification of murine IL-4R. Alternatively, 50 µl aliquots of 20% suspension of IL-4-coupled Affigel® were incubated with $^{35}$S-cysteine/ methionine-labeled cell extracts for small-scale affinity purifications and gel electrophoresis.

Aliquots (25 ml) of HeLa E3C3 culture supernatants (containing soluble IL-4 receptor) were slowly applied to the murine IL-4 affinity column at 4° C. (flow rate of 3.0 ml/hr). The column was then washed sequentially with PBS to remove all contaminating material except the bound mIL-4R. The column was then eluted with 0.01M acetic acid, 0.15M sodium chloride, pH 3.0 to remove the IL-4R and washed subsequently with PBS. One ml fractions were collected for the elution and 2 ml fractions collected during the wash. Immediately following elution, samples were neutralized with 80 ul of 1M Hepes, pH 7.4. The presence of receptor in the fractions was detected by the inhibition binding assay described above.

From 100 ml of HeLa E3C3 culture supernatant approximately 600 ug of soluble IL-4 receptor protein was purified on a 4.0 ml affinity column. Purified receptor consisted of three major bands ranging from 30–39,000 daltons on SDS-PAGE. Heterogeneity in size of this preparation is due to variability in protein glycosylation, as treatment of the protein with N-glycanase to remove N-linked carbohydrates reduces the size of the protein to ~25,000 daltons on SDS-PAGE. In addition, amino acid sequencing confirmed that the bands have the same N-terminal sequence. Purity and protein concentrations were also confirmed by amino acid analysis.

Example 9

Expression of IL-4R in yeast cells

For expression of mIL-4R, a yeast expression vector derived from pIXY120 was constructed as follows. pIXY120 is identical to pYαHuGM (ATCC 53157), except that it contains no cDNA insert and includes a polylinker/ multiple cloning site with an Nco I site. This vector includes DNA sequences from the following sources: (1) a large Sph I (nucleotide 562) to EcoR I (nucleotide 4361) fragment excised from plasmid pBR322 (ATCC 37017), including the origin of replication and the ampicillin resistance marker for selection in E. coli, (2) S. cerevisiae DNA including the TRP-1 marker, 2µ origin of replication, ADH2 promoter; and (3) DNA encoding an 85 amino acid signal peptide derived from the gene encoding the secreted peptide α-factor (See Kurjan et al., U.S. Pat. No. 4,546,082). An Asp 718 restriction site was introduced at position 237 in the α-factor signal peptide to facilitate fusion to heterologous genes. This was achieved by changing the thymidine residue at nucleotide 241 to a cytosine residue by oligonucleotide-directed in vitro mutagenesis as described by Craik, BioTechniques, January 1985, pp.12–19. A synthetic oligonucleotide containing multiple cloning sites and having the following sequence was inserted from the Asp718 site at amino acid 79 near the 3' end of the α-factor signal peptide to a SpeI site in the 2µ sequence:

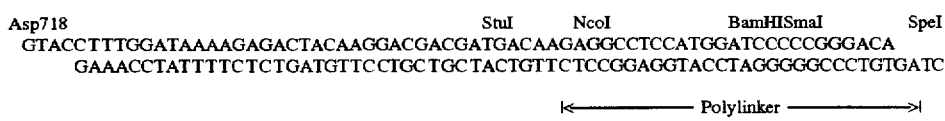

pBC120 also varies from pYαHuGM by the presence of a 514 bp DNA fragment derived from the single-stranded phage f1 containing the origin of replication and intergenic region, which has been inserted at the Nru I site in the pBR322 sequence. The presence of an f1 origin of replication permits generation of single-stranded DNA copies of the vector when transformed into appropriate strains of E. coli and superinfected with bacteriophage f1, which facilitates DNA sequencing of the vector and provides a basis for in vitro mutagenesis. To insert a cDNA, pIXY120 is digested with Asp 718 which cleaves near the 3' end of the α-factor leader peptide (nucleotide 237) and, for example, BamH I which cleaves in the polylinker. The large vector fragment is then purified and ligated to a DNA fragment encoding the protein to be expressed.

To create a secretion vector for expressing mIL-4R, a cDNA fragment encoding mIL-4R was excised from the Bluescript® plasmid of Example 8 by digestion with Ppum I and Bgl II to release an 831 bp fragment from the Ppum I site (see FIGURE) to an Bgl II site located 3' to the open reading frame containing the mIL-4R sequence minus the first two 5' codons encoding Ile and Lys. pIXY120 was digested with Asp 718 near the 3' end of the α-factor leader and BamH I. The vector fragment was ligated to the Ppum I/Bgl II hIL-4R cDNA fragment and the following fragment created by annealing a pair of synthetic oligonucleotides to recreate the last 6 amino acids of the α-factor leader and the first two amino acids of mature mIL-4R.

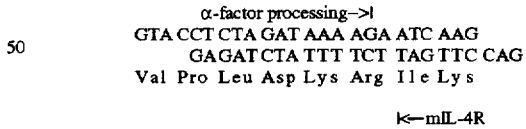

The oligonucleotide also included a change from the nucleotide sequence TGG ATA to CTA GAT which introduces a Xba I restriction site, without altering the encoded amino acid sequence.

The foregoing expression vector was then purified and employed to transform a diploid yeast strain of S. cerevisiae (XV2181) by standard techniques, such as those disclosed in EPA 165,654, selecting for tryptophan prototrophs. The resulting transformants were cultured for expression of a secreted mIL-4R protein. Cultures to be assayed for biological activity were grown in 20–50 ml of YPD medium (1% yeast extract, 2% peptone, 1% glucose) at 37° C. to a cell density of 1–5×10⁸ cells/ml. To separate cells from medium, cells were removed by centrifugation and the medium filtered through a 0.45μ cellulose acetate filter prior to assay. Supernatants produced by the transformed yeast strain, or crude extracts prepared from disrupted yeast cells transformed the plasmid, were assayed to verify expression of a biologically active protein.

Example 10

Isolation of full-length and truncated forms of murine IL-4 receptor cDNAs from unsorted 7B9 cells Polyadenylated RNA was isolated from 7B9 cells, an antigen-dependent helper T cell clone derived from C57BL/6 mice, and used to construct a cDNA library in λZAP (Stratagene, San Diego), as described in Example 7. The λZAP library was amplified once and a total of 300,000 plaques were screened as described in Example 7, with the exception that the probe was a randomly primed $^{32}$P-labeled 700 bp EcoR I fragment isolated from CTLL 19.4 clone 16. Thirteen clones were isolated and characterized by restriction analysis.

Nucleic acid sequence analysis of clone 7B9-2 revealed that it contains a polyadenylated tail, a putative polyadenylation signal, and an open reading frame of 810 amino acids (shown in FIG. 2), the first 258 of which are identical to those encoded by CTLL 19.4 clone 16, including the 25 amino acid putative signal peptide sequence. The 7B9-2 cDNA was subcloned into the eukaryotic expression vector, pCAV/NOT, and the resulting plasmid was transfected into COS-7 cells as described in Example 8. COS-7 transfectants were analyzed as set forth in Example 12.

A second cDNA form, similar to clone 18 in the CTLL 19.4 library, was isolated from the 7B9 library and subjected to sequence analysis. This cDNA, clone 7B9-4, is 376 bp shorter than clone 7B9-2 at the 5' end, and lacks the first 47 amino acids encoded by 7B9-2, but encodes the remaining N-terminal amino adds 23–199 (in FIG. 2). At position 200, clone 7B9-4 (like clone 18 from CTLL 19.4) has a 114 bp insert which changes the amino acid sequence to Pro Ser Asn Glu Asn Leu followed by a termination codon. The 114 bp inserts, found in both clone 7B9-4 and CTLL 19.4 clone 18 are identical in nucleic acid sequence. The fact that this cDNA form, which produces a secreted form of the IL-4 receptor when expressed in COS-7 cells, was isolated from these two different cell lines indicates that it is neither a cloning artifact nor a mutant form peculiar to the sorted CTLL cells.

Example 11

Isolation of human IL-4 receptor cDNAs from PBL and T22 libraries by cross-species hybridization Polyadenylated RNA was isolated from pooled human peripheral blood lymphocytes (PBL) that were obtained by standard Ficoll purification and were cultured in IL-2 for six days followed by stimulation with PMA and Con-A for eight hours. An oligo dT primed cDNA library was constructed in λgt10 using techniques described in example 7. A probe was produced by synthesizing an unlabeled RNA transcript of the 7B9-4 cDNA insert using T7 RNA polymerase, followed by $^{32}$P-labeled cDNA synthesis with reverse transcriptase using random primers (Boehringer-Mannheim). This murine single-stranded cDNA probe was used to screen 50,000 plaques from the human cDNA library in 50% formamide/ 0.4M NaCl at 42° C., followed by washing in 2×SSC at 55° C. Three positive plaques were purified, and the EcoR I inserts subcloned into the Bluescript® plasmid vector.

Nucleic acid sequencing of a portion of clone PBL-1, a 3.4 kb cDNA, indicated the clone was approximately 67% homologous to the corresponding sequence of the murine IL-4 receptor. However, an insert of 68 bp, containing a termination codon and bearing no homology to the mouse IL-4 receptor clones, was found 45 amino acids downstream of the predicted N-terminus of the mature protein, suggesting that clone PBL-1 encodes a non-functional truncated form of the receptor. Nine additional human PBL clones were obtained by screening the same library (under stringent conditions) with a $^{32}$P-labeled random-primed probe made from the clone PBL-1 (the 3.4 kb EcoR I cDNA insert). Two of these clones, PBL-11 and PBL-5, span the 5' region that contains the 68 bp insert in PBL-1, but lack the 68 bp insert and do not extend fully 3', as evidenced by their size, thus precluding functional analysis by mammalian expression. In order to obtain a construct expressible in COS-7 cells, the 5' Not I-Hinc II fragment of clones PBL-11 and PBL-5 were separately ligated to the 3' Hinc II-BamH I end of clone PBL-1, and subcloned into the pCAV/NOT expression vector cut with Not I and Bgl II described in Example 8. These chimeric human IL-4R cDNAs containing PBL-11/PBL-1 and PBL-5/PBL-1 DNA sequences have been termed clones A5 and B4, respectively, as further described in Example 12. These constructs were transfected into COS-7 cells, and assayed for IL-4 binding in a plate binding assay substantially as described in Sims et al. (*Science* 241:585, 1988). Both composite constructs encoded protein which exhibited IL-4 binding activity. The nucleotide sequence and predicted amino acid sequence of the composite A5 construct correspond to the sequence information set forth in FIGS. 4A–4C, with the exception that a GTC codon encodes the amino acid Val at position 50, instead of Ile. No other clones that were sequenced contained this change. The consensus codon from clones PBL-1, PBL-5 and T22-8, however, is ATC and encodes Ile$^{50}$, as set forth in FIG. 4A. The nucleotide and predicted amino acid sequence of the composite B4 construct also shows that the 25 amino acid leader sequence of PBL-11 is replaced with the sequence Met-Gln-Lys-Asp-Ala-Arg-Arg-Glu-Gly-Asn.

Constructs expressing a soluble form of the human IL-4 receptor were made by excising a 5'-terminal 0.8 kb Sma I-Dra III fragment from PBL-5 and the corresponding 0.8 kb Asp718-Dra III fragment from PBL-11, of which the Dra III overhangs were blunt-ended with T4 polymerase. The PBL-5 and PBL-11 fragments were separately subcloned into CAV/NOT cut with Sma I or Asp 718 plus Sma I, respectively; these are called soluble hIL-4R-5 and soluble hIL-4R-11, respectively.

A second library made from a CD4+/CD8– human T cell clone, T22, (Acres et al., *J. Immunol.* 138:2132, 1987) was screened (using duplicate filters) with two different probes synthesized as described above. The first probe was obtained from a 220 bp Pvu II fragment from the 5' end of clone PBL-1 and the second probe was obtained from a 300 bp Pvu II -EcoR I fragment from the 3' end of clone PBL-1. Five additional cDNA clones were identified using these two probes. Two of these clones span the 5' region containing the 68 bp insert, but neither contain the insert. The third of these clones, T22-8, was approximately 3.6 kb in size and contained an open reading frame of 825 amino acids, including a 25 amino acid leader sequence, a 207 amino acid mature external domain, a 24 amino acid transmembrane region and a 569 amino acid cytoplasmic domain. The sequence of clone T22-8 is set forth in FIGS. 4A–4C. FIGS. 5A–5B compare the predicted human IL-4R amino acid sequence with the predicted murine IL-4R sequence and show approximately 53% sequence identity between the two proteins.

Example 12

Analysis and purification of IL-4 receptor in COS transfectants

Equilibrium binding studies were conducted for COS cells transfected with murine IL-4 receptor clones 16 and 18 from the CTLL 19.4 library. In all cases analysis of the data in the Scatchard coordinate system (Scatchard, Ann. N.Y. Acad. Sci. 51:660–672, 1949) yielded a straight line, indicating a single class of high-affinity receptors for murine IL-4. For COS pCAV-16 cells the calculated apparent $K_a$ was $3.6 \times 10^9$ $M^{-1}$ with $5.9 \times 10^5$ specific binding sites per cell. A similar apparent $K_a$ was calculated for COS pCAV-18 cells at $1.5 \times 10^9$ $M^{-1}$ but receptor number expressed at the cell surface was $4.2 \times 10^4$. Equilibrium binding studies performed on COS cells transfected with IL-4R DNA clones isolated from the 7B9 cell library also showed high affinity binding of the receptor to IL-4. Specifically, studies using COS cells transfected with pCAV-7B9-2 demonstrated that the full length murine IL-4 receptor bound $^{125}$I-IL-4 with an apparent $K_a$ of about $1.4 \times 10^{10}$ $M^{-1}$ with $4.5 \times 10^4$ specific binding sites per cell. The apparent $K_a$ of CAV-7B9-4 IL-4R was calculated to be about $1.7 \times 10^9$ $M^{-1}$. Although absolute values for $K_a$ and binding sites per cell varied between transfections, the binding affinities were generally similar ($1 \times 10^9$–$1 \times 10^{10}$ $M^{-1}$) and matched well with previously published affinity constants for IL-4 binding.

Inhibition of $^{125}$I-mIL-4 binding to CTLL cells by conditioned media from COS cells transfected with plasmid pCAV, pCAV-18, or pCAV-7B9-4 was used to determine if these cDNAs encoded functional soluble receptor molecules. Approximately 1.5 μl of COS pCAV-18 conditioned media in a final assay volume of 150 μl gives approximately 50% inhibition of $^{125}$I-IL-4 binding to the IL-4 receptor on CTLL cells. $^{125}$I-IL-4 receptor competing activity is not detected in control pCAV transfected COS supernatants. From quantitative analysis of the dilution of pCAV-18 supernatant required to inhibit $^{125}$I-IL-4 binding by 50%, it is estimated that approximately 60–100 ng/ml of soluble IL-4 receptor has been secreted by COS cells when harvested three days after transfection. Similar results were obtained utilizing supernatants from COS cells transfected with pCAV-7B9-4.

Conditioned medium from COS cells transfected with pCAV-18 or pCAV-7B9-4 (see Example 8) and grown in DMEM containing 3% FBS was harvested three days after transfection. Supernatants were centrifuged at 3,000 cpm for 10 minutes, and frozen until needed. Two hundred ml of conditioned media was loaded onto a column containing 4 ml of muIL-4 Affigel prepared as described above. The column was washed extensively with PBS and IL-4 receptor eluted with 0.1M glycine, 0.15M NaCl pH 3.0. Immediately following elution, samples were neutralized with 80 μl of 1M Hepes pH 7.4. Samples were tested for their ability to inhibit binding of $^{125}$I-muIL-4 to CTLL cells as set forth in Example 1B. Additionally samples were tested for purity by analysis on SDS-PAGE and silver staining as previously described. Alternative methods for testing functional soluble receptor activity or IL-4 binding inhibition include solid-phase binding assays, as described in Example 1C, or other similar cell free assays which may utilize either radio iodinated or colorimetrically developed IL-4 binding, such as RIA or ELISA. The protein analyzed by SDS-PAGE under reducing conditions has a molecular weight of approximately 37,500, and appears approximately 90% pure by silver stain analysis of gels.

Purified recombinant soluble murine IL-4 receptor protein may also be tested for its ability to inhibit IL-4 induced $^3$H-thymidine incorporation in CTLL cells. Pursuant to such methods, soluble IL-4 receptor has been found to block IL-4 stimulated proliferation, but does not affect IL-2 driven mitogenic response.

Molecular weight estimates were performed on mIL-4 receptor clones transfected into COS cells. Utilizing M2 monoclonal antibody prepared against murine CTLL 19.4 cells (see Example 13), IL-4 receptor is immunoprecipitated from COS cells transfected with CAV-16, CAV-7B9-2 and CAV-7B9-4 and labeled with $^{35}$S-cysteine and $^{35}$S-methionine. Cell associated receptor from CAV-7B9-4 shows molecular weight heterogeneity ranging from 32–39 kDa. Secreted CAV-7B9-4 receptor has molecular weight between 36 and 41 kDa. Cell associated receptor from CAV-16 transfected COS cells is about 40–41 kDa. This is significantly smaller than molecular weight estimations from crosslinking studies described by Park et al., J. Exp. Med. 166:476, 1987; J. Cell. Biol., Suppl. 12A, 1988. Immunoprecipitation of COS CAV-7B9-2 cell-associated receptor showed a molecular weight of 130–140 kDa, similar to the estimates of Park et al., J. Cell. Biol., Suppl. 12A, 1988, estimated to be the full length IL-4 receptor. Similar molecular weight estimates of cell-associated CAV-16 and CAV-7B9-2 IL-4 receptor have also been made based on cross-linking $^{125}$I-4 to COS cells transfected with these cDNAs. Heterogeneity of molecular weight of the individual clones can be partially attributed to glycosylation This data, together with DNA sequence analysis, suggests that the 7B9-2 cDNA encodes the full length cell-surface IL-4 receptor, whereas both 7B9-4 and clone 18 represent soluble forms of murine IL-4 receptor.

Receptor characterization studies were also done on COS cells transfected with hIL-4R containing expression plasmids. The two chimeric human IL-4R molecules A5 and B4 (defined in Example 11) were transfected into COS cells and equilibrium binding studies undertaken. The COS monkey cell itself has receptors capable of binding hIL-4; therefore the binding calculations performed on COS cells transfected with and overexpressing hIL-4R cDNAs represent background binding from endogenous monkey IL-4R molecules subtracted from the total binding. COS cells transfected with hIL-4R A5 had $5.3 \times 10^4$ hIL-4 binding sites with a calculated $K_a$ of $3.48 \times 10^9$ $M^{-1}$. Similarly, the hIL-4R B4 expressed in COS cells bound $^{125}$I-hIL-4 with an affinity of $3.94 \times 10^9$ $M^{-1}$ exhibiting $3.2 \times 10^4$ receptors per cell.

Molecular weight estimates of human IL-4R expressed in COS cells were also performed. COS cells transfected with clones A5 or B4 in pCAV/NOT were labeled with $^{35}$S-cysteine/methionine and lysed. Human IL-4R was affinity purified from the resulting lysates with hIL-4-coupled Affigel® (as described in Example 4). The hIL-4R A5 and B4 eluted from this affinity support migrated at about 140,000 daltons on SDS-PAGE, agreeing well with previous estimates of hIL-4R molecular weight by cross-linking (Park et al., J. Exp. Med. 166:476, 1987), as well as with estimates of full-length mIL-4R presented here.

Because no soluble human IL-4R cDNA has thus far been found occurring naturally, as was the case for the murine receptor (clones 18 and 7B9-4), a truncated form was constructed as described in Example 11. Following expression in COS cells, supernatants were harvested three days after transfection with soluble hIL-4R-11 and soluble hIL-4R-5 and tested for inhibition of $^{125}$I-hIL-4 binding to the human B cell line Raji. Supernatants from two of the soluble hIL-4R-11 and one of the soluble hIL-4R-5 transfected plates contained 29–149 ng/ml of IL-4R competing activity into the medium. In addition, the truncated protein could be detected in $^{35}$S-methionine/cysteine-labeled COS cell transfectants by affinity purification on hIL-4-coupled Affigel® as approximately a 44 kDa protein by SDS-PAGE.

Example 13

Preparation of monoclonal antibodies to IL-4R

Preparations of purified recombinant IL-4 receptor, for example, human or murine IL-4 receptor, transfected COS cells expressing high levels of IL-4 receptor or CTLL 19.4 cells are employed to generate monoclonal antibodies against IL-4 receptor using conventional techniques, such as those disclosed in U.S. Pat. No. 4,411,993. Such antibodies are likely to be useful in interfering with IL-4 binding to IL-4 receptors, for example, in ameliorating toxic or other undesired effects of IL-4.

To immunize rats, IL-4 receptor bearing CTLL 19.4 cells were used as immunogen emulsified in complete Freund's adjuvant and injected in amounts ranging from 10–100 μl subcutaneously into Lewis rats. Three weeks later, the immunized animals were boosted with additional immunogen emulsified in incomplete Freund's adjuvant and boosted every three weeks thereafter. Serum samples are periodically taken by retro-orbital bleeding or tail-tip excision for testing by dot-blot assay, ELISA (enzyme-linked immunosorbent assay), or inhibition of binding of $^{125}$I-IL-4 to extracts of CTLL cells (as described in Example 1). Other assay procedures are also suitable. Following detection of an appropriate antibody titer, positive animals were given a final intravenous injection of antigen in saline. Three to four days later, the animals were sacrificed, splenocytes harvested, and fused to the murine myeloma cell line AG8653. Hybridoma cell lines generated by this procedure were plated in multiple microtiter plates in a HAT selective medium (hypoxanthine, aminopterin, and thymidine) to inhibit proliferation of non-fused cells, myeloma hybrids, and spleen cell hybrids.

Hybridoma clones thus generated were screened for reactivity with IL-4 receptor. Initial screening of hybridoma supernatants utilized an antibody capture and binding of partially purified $^{125}$I-mIL-4 receptor. Two of over 400 hybridomas screened were positive by this method. These two monoclonal antibodies, M1 and M2, were tested by a modified antibody capture to detect blocking antibody. Only M1 was able to inhibit $^{125}$I-rmIL-4 binding to intact CTLL cells. Both antibodies are capable of immunoprecipitating native mIL-4R protein from CTLL cells or COS-7 cells transfected with IL-4R clones labelled with $^{35}$S-cysteine/methionine. M1 and M2 were then injected into the peritoneal cavities of nude mice to produce ascites containing high concentrations (>1 mg/ml) of anti-IL-4R monoclonal antibody. The resulting monoclonal antibody was purified by ammonium sulfate precipitation followed by gel exclusion chromatography, and/or affinity chromatography based on binding of antibody to Protein G.

A series of experiments (Examples 14–19) was conducted to show that sIL-4R inhibits IL-4 mediated B cell growth, differentiation and function in vitro. Each of these experiments utilized soluble IL-4R produced as described in Example 8C. Example 14 shows that sIL-4R inhibits the proliferation of stimulated B cells. Examples 15, 16 and 17 show, respectively, that sIL-4R inhibits IL-4 dependent B cell differentiation as measured by induction of IgG1 and IgE secretion by LPS activated B cells, down regulation of IgG3 secretion by LPS activated B cells, and increased Ia and FceR (CD23) expression, respectively. In the following experiments, the activity of sIL-4R is compared with sIL-1R to show that the inhibitory effects of the soluble receptors are specific in that sIL-4R has no effect on IL-1 induced B cell activity and sIL-1R has no effect on IL-4 activity, thus demonstrating two independent pathways of B cell activation directed by IL-1 and IL-4.

Example 14

Inhibition of IL-4 Binding to B cells in vitro by Soluble IL-4R

Untreated B cells express low, but detectable levels of IL-4 receptors. Upon stimulation with the B cell mitogen LPS, these cells show enhanced cell surface IL-4 receptor expression. The following experiments were conducted to show that sIL-4R inhibits radiolabeled IL-4 binding to LPS activated B lymphocytes.

B lymphocytes were first purified from spleens of 8 to 12 week-old C57BL/6 mice (Jackson Laboratory, Bar Harbor, Me. and Simonson, Gilroy, Calif.) as described by Grabstein, et al., *J. Exp. Med.* 163:1405, 1986. Briefly, murine splenocytes were depleted of T cells by incubation in a cocktail containing T24 rat anti-Thy 1 mAb (Dennert et al., *J. Immunol* 131:2445 (1983), GK1.5 rat anti-mouse L3T4 mAb (Dialynas et al., *Cell. Immunol.* 53:350, (1980), rabbit anti-mouse thymocyte serum (absorbed with C57BL/6 liver and bone marrow), and rabbit complement (Pel-Freeze Biologicals, Rogers, Ark.). Cells were then passed over Sephadex G-10 (Pharmacia Uppsala, Sweden) to remove adherent cells. B lymphocytes were positively selected by panning on petri dishes coated with affinity purified goat anti-mouse IgM (Organon Teknika Corp., West Chester, Pa.). The resultant preparations were >98% B cells as determined by flow cytometry.

The purified B cells were then cultured in RPMI 1640 supplemented with 5% fetal calf serum (Hazelton), sodium pyruvate (1 mM), nonessential amino acids (0.1 mM), penicillin (100 U/ml), streptomycin (100 ug/ml), L-glutamine (2 mM), and 2-mercaptoethanol (50 uM), as well as *Salmonella typhimurium* LPS (10 ug/ml; Difco Laboratories, Detroit, Mich.) to produce activated B cells.

Human rIL-1β was produced in *Escherichia coli* and purified to homogeneity as described by Kronheim et al., *Bio/Technology* 4:1708, 1986. Recombinant murine IL-4 was produced in yeast, purified to homogeneity, and radiolabeled as described by Mosley et al., *Cell* 59:355, 1989, and Park et al., *Proc. Natl. Acad. Sci. USA* 84:1669, 1987.

Inhibition assays were performed by first incubating various concentrations of unlabeled cytokines (IL-1 or IL-4), soluble receptors (sIL-1R or sIL-4R), monoclonal antibody (11B11, a rat IgGI anti-murine IL-4 antibody produced as described by Ohara et al., *Nature* 315:333, 1985) or medium control with 50 ul $^{125}$I-labeled IL-4 ($1.65 \times 10^{-10}$M) for thirty minutes in 10% $CO_2$ at 37° C. in binding medium (RPMI/2.5% BSA/0.2% sodium azide/0.2M Hepes, pH 7.4). To these $2 \times 10^6$ murine B cells were added in 50 ul of binding medium for 30 min at 37° C. Cells were then separated by the phthalate oil method as described by Dower et al., *J. Immunol.* 132:751, 1984. Percent specific inhibition was calculated using incubation of $^{125}$I-IL-4 with excess unlabeled IL-4 ($4 \times 10^{-9}$M) as positive control and 50 ul of binding medium as negative control. Each assay was performed with 3-fold dilutions in duplicate of each competitor compound through binding medium, and incubations carried out in 96-well round bottom plates (Linbro, Hamden, Conn.).

Results of the inhibition assays indicate that IL-4 binding was inhibited by unlabeled sIL-4R, unlabeled IL-4, and 11B11, an anti-IL-4 specific mAb. The blocking effect was cytokine specific, and cross-competition between IL-4 and either 11B11 or sIL-4R generated similar inhibition constants as shown in Table A below. No competition of IL-4 binding was detected by IL-1 or sIL-1R.

TABLE A

Inhibition of Radiolabeled IL-4 Binding to LPS Blasts

| Inhibitor | Inhibition Constant (M$^{-1}$) |
| --- | --- |
| IL-4 | $4.9 \times 10^{10}$ |
| sIL-4R | $4.8 \times 10^9$ |
| 11B11 | $7.9 \times 10^9$ |
| IL-1 | No Inhibition |
| sIL-1R | No Inhibition |

Example 15

Inhibition of Lymphokine Induced B Cell Proliferation in vita by sIL-4R

Murine B cell proliferation is stimulated by treatment of anti-immunoglobulin and either IL-1 (Howard et al., *J. Exp. Med.* 157:1529, 1983; Booth et al., *J. Immunol* 33:1346, 1984) or IL-4 (Grabstein et al., *J. Mol. Cell. Immunol.* 2:199, 1986; Howard et al, *J. Exp. Med.* 155:914, 1982). The ability of sIL-1R and sIL-4R to inhibit these B cell mitogenic responses was tested in a B cell proliferation assay as follows.

B cells were purified and cultured as described in Example 14 above. In order to determine the effect of various doses of inhibitors on B cell proliferation, the purified B cells were seeded at 1×10⁵ cells/well in 96-well flat-bottom tissue culture plates (Costar) in the presence of affinity purified goat anti-mouse IgM (2.5 ug/ml; Zymed Laboratories, Inc., So. San Francisco, Calif.) and various concentrations of IL-4 (panel A) or IL-1 (panel B), either alone (○) or in the presence of 1000 ng/ml sIL-4R (□), 1000 ng/ml sIL-1R (■), or 555 ng/ml 11B11 (●) as inhibitors. After 2 days, cultures received 2 uCi/well of [$^3$H] thymidine (25 Ci/mmol; Amersham, Arlington Heights., Ill.) for 16 hours, and were then harvested onto glass fiber filters. Incorporation of radioactivity was measured by liquid scintillation spectrophotometry. Tritiated thymidine incorporation for triplicate wells was determined for the final 16 hours of a three day culture period. Results are presented as mean cpm±SEM.

In order to determine the effect of various doses of inhibitor on the inhibition of B cell proliferation by cytokines, purified B cells were seeded at 1×10⁵ cells/well in 96-well flat-bottom tissue culture plates (Costar) in the presence of affinity purified goat anti-mouse IgM (25 μg/ml; Zymed Laboratories, Inc., So. San Francisco, Calif.) and fixed concentrations of 10 (●), 1 (□), 0.1 (○), or 0 (Δ) ng/ml of IL-4 (panels A–C) or IL-1 (panels D–F). Culture wells also included three-fold dilutions of sIL-4R (panels A, D), 11B11 (panels B,E), or sIL-1R (panels C,F). After 2 days, cultures received 2 uCi/well of [$^3$H]thymidine (25 Ci/mmol; Amersham, Arlington Heights., Ill.) for 16 hours, and were then harvested onto glass fiber filters. Incorporation of radioactivity was measured by liquid scintillation spectrophotometry as indicated above. Tritiated thymidine incorporation for triplicate wells was determined for the final 15 hours of a three day culture period. Results are presented as mean cpm±SEM.

Figure 6A:
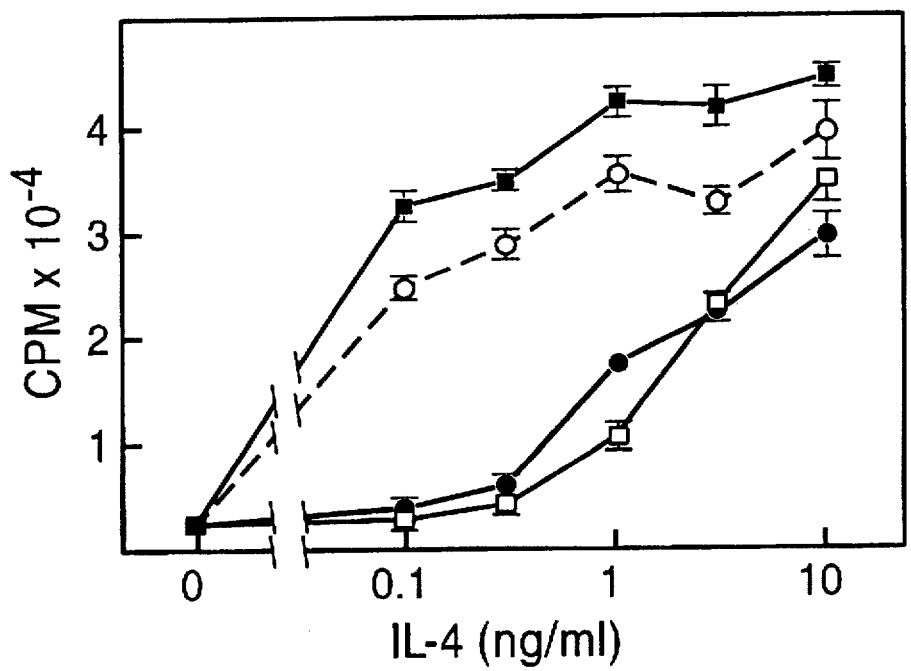
FIG. 6 shows the inhibition of B cell proliferation with IL-4 (panel A) or IL-1 (panel B) at various doses either alone (○) or in the presence of sIL-4R (□), sIL-1R (■) or anti-IL-4 antibody (●) as described in Example 15.
Figure 6B:
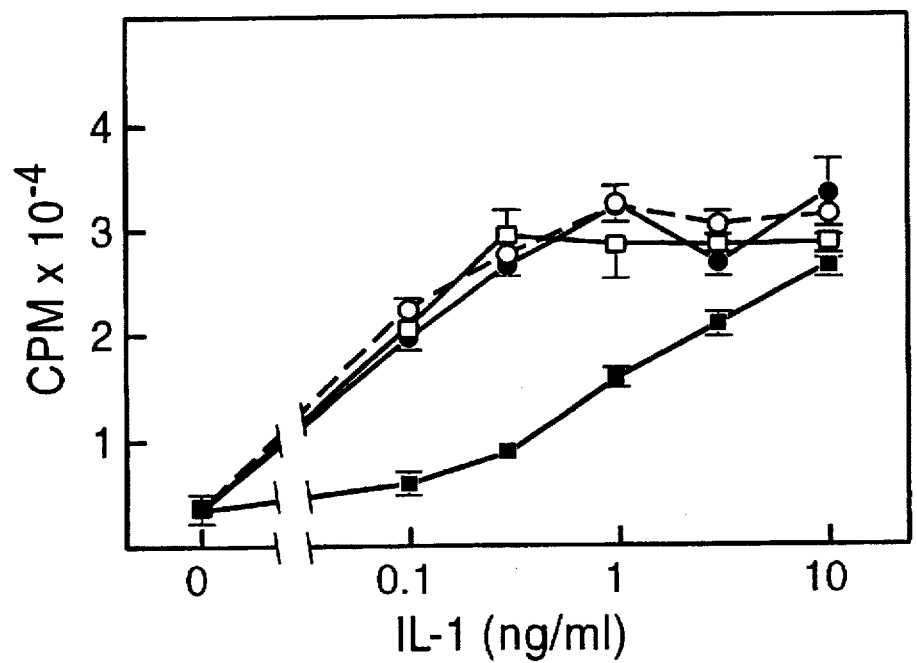
Figure 7A:
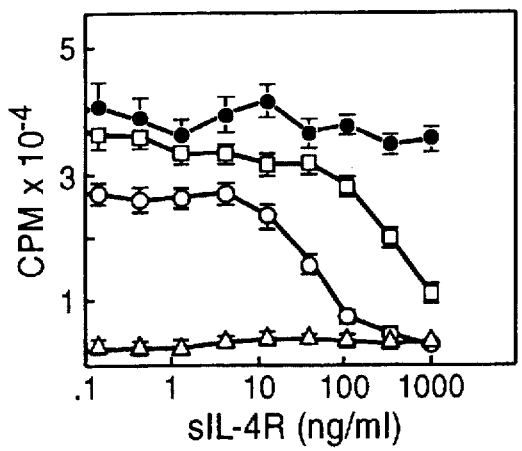
FIG. 7 shows the inhibition of B cell proliferation with fixed concentrations of 10 (●), 1 (□), 0.1 (○) or 0 (△) ng/ml of IL-4 (panels A–C) and IL-1 (panels D–F) at various doses of sIL-4R (panels A & D), anti-IL4 antibody (panels B & E) and sIL-1R (panels C & F) as described in Example 15.
Figure 7D:
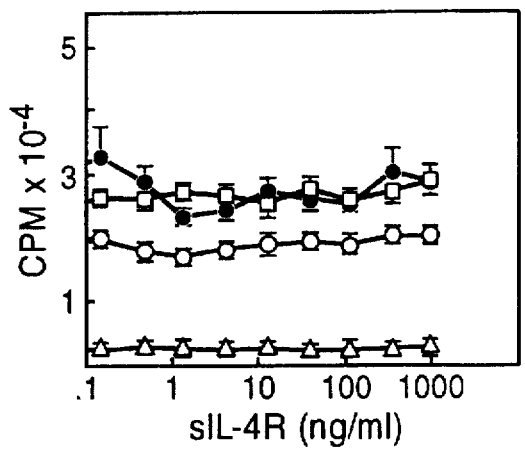
Figure 7B:
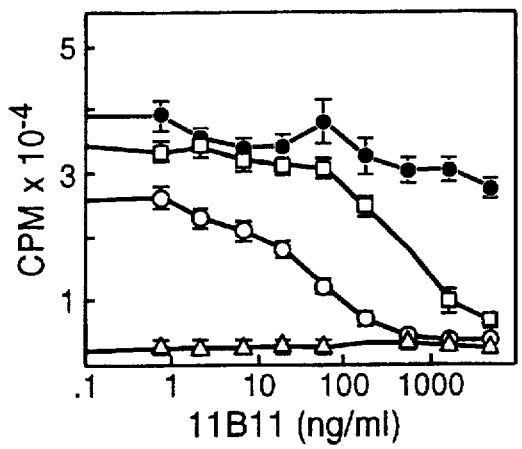
Figure 7E:
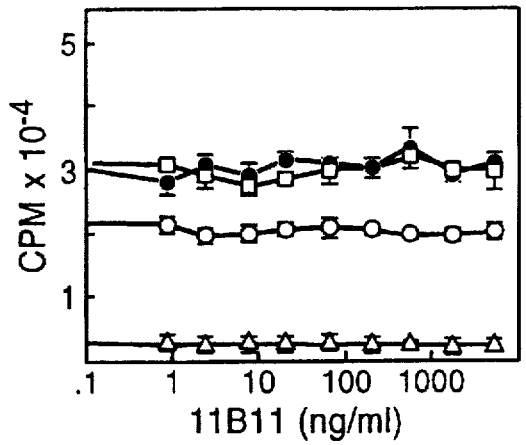
Figure 7C:
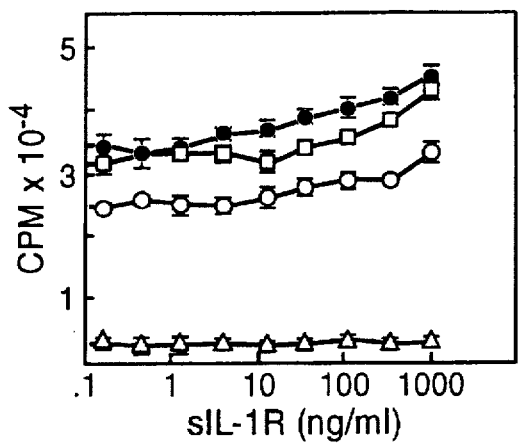
Figure 7F:
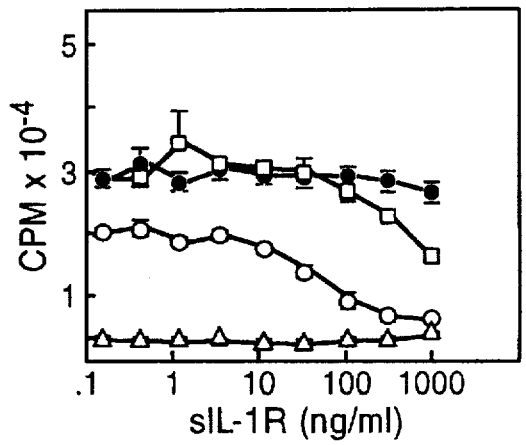

FIGS. 6 and 7 show that sIL-4R and sIL-1R inhibitory activity was dose dependent and specific for the respective ligands. The inhibitory effects of the sIL-4R and 11B11 were virtually equivalent on a molar basis, with half-maximal inhibition of IL-4-induced proliferation requiring a 100–200 fold molar excess of either inhibitor. Half-maximal inhibition of IL-1 activity was achieved with a 300–400 fold molar excess of sIL-1R.

Example 16

Inhibition of IL-4 Induced Immunoglobulin Secretion In Vitro by sIL-4R

IL-4 augments LPS-induced secretion of IgG1 and IgE and inhibits IgG3 production, possibly by a mechanism involving class switching from one isotype of an antibody to another isotype. The ability of sIL-4R to inhibit IL-4 induced class switching in LPS-stimulated B cells was tested in the following assay that measures immunoglobulin secretion from LPS treated B cells.

B cells were purified and cultured as described in Example 14 above. In order to determine the effect of various doses of IL-4 on IgG1, IgE and IgG3 secretion, the purified B cells (1×10⁵ cells/well) were grown in 96-well flat bottom plates in the presence of *Salmonella typhimurium* LPS (Difco Laboratories, Detroit, Mich.) and three-fold dilutions of IL-4 with sIL-4R (□), sIL-1R (■) or 11B11 (●), each at 555 ng/ml or medium control (Δ) (see FIG. 8). Six days after initiation of culture, cells were pelleted by centrifugation at 750×g and culture supernatant fluids were harvested.

Immunoglobulin (IgG1, IgG3, and IgE) levels were determined by an isotype specific sandwich ELISA technique as follows. 96-well flat-bottom Linbro plates (Flow Laboratories, Inc., McLean, Va.) were coated overnight with the appropriate (see below) first step isotype specific antibody (100 ul) and washed. This and all subsequent washing steps were done with phosphate buffered saline containing 0.05% Tween 20, 6 rinses per cycle. Nonspecific sites were blocked by incubation for one hour with 150 ul of 5% nonfat dry milk. Test material (100 ul), either culture supernatant or isotype standard curve solutions (all sample and antibody dilutions in PBS/3% BSA), was added to each well, incubated for 1 hour, then washed. 100 ul of the appropriate (see below) horseradish peroxidase-conjugated second step antibody was added and plates were incubated for 1 hour and washed. The presence of peroxidase-conjugated antibody was determined by using the TMB Microwell peroxidase substrate system (Kirkegaard & Perry Laboratories, Inc., Gaithersburg, Md.). Plates were read on a Dynatech ELISA reader. Immunoglobulin concentrations in test samples were determined by comparing triplicate test values with isotype control standard curves, using the DeltaSoft 1.8 ELISA analysis program for the Macintosh (Biometallics, Inc., Princeton, N.J.).

For the IgG1 and IgG3 assays, unconjugated and horseradish peroxidase-conjugated affinity purified goat anti-mouse isotype specific reagents (Southern Biotechnology Associates, Inc., Birmingham, Ala.) were used as plate coating and second step reagents, respectively. Standard curves for IgG1 and IgG3 were run with isotype matched murine myeloma proteins (Southern). For the IgE assay, the EM95 IgG2a anti-mouse IgE mAb (Baniyash et al., *Eur. J. Immunol.* 14:797, 1984) (provided by Dr. Fred Finkelman, Uniformed Services, Bethesda, Md.) was used as plate coating step reagent and biotinylated rat anti-mouse IgE (Bioproducts for Science, Inc., Indianapolis, Ind.) was used as second step reagent, and horse radish peroxidase-conjugated streptavidin (Zymed) was used in the third step. Standard curves were established with a murine antidinitrophenol specific IgE myeloma antibody (ATCC No. TIB 141). All three ELISA assays were determined to be specific based upon cross-reactivity experiments using all individual murine antibody isotypes as controls.

Figure 9A:
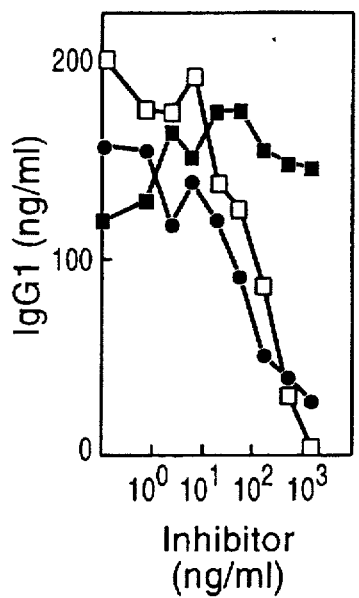
FIG. 9 shows the inhibition of IL-4-induced immunoglobulin class switching with fixed concentration of IL-4 and various doses of sIL-4R (□), sIL-1R (■), anti-IL-4 antibody (●) or medium control (△) as described in Example 16.
Figure 9B:
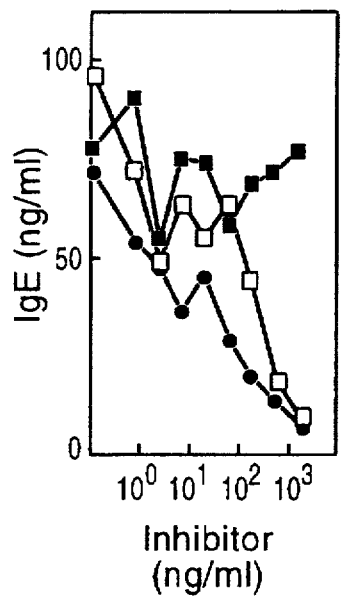
Figure 9C:
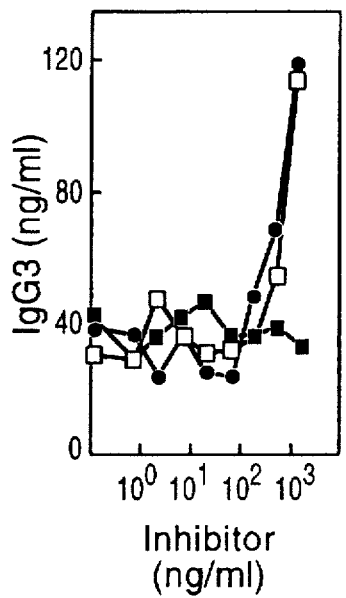
Figure 10A:
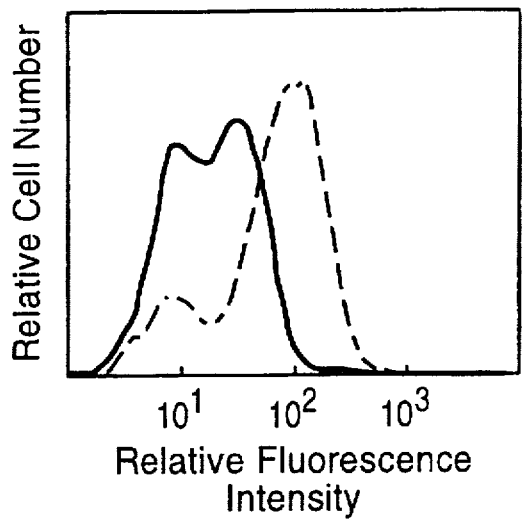
FIG. 10 shows the inhibition of MHC class II antigen expression with (dashed line) or without (solid line) IL-4 in the presence of medium control (panel A), sIL-4R (panel B), anti-IL-4 antibody (panel C) or sIL-1R (panel D) as described in Example 17.
Figure 10B:
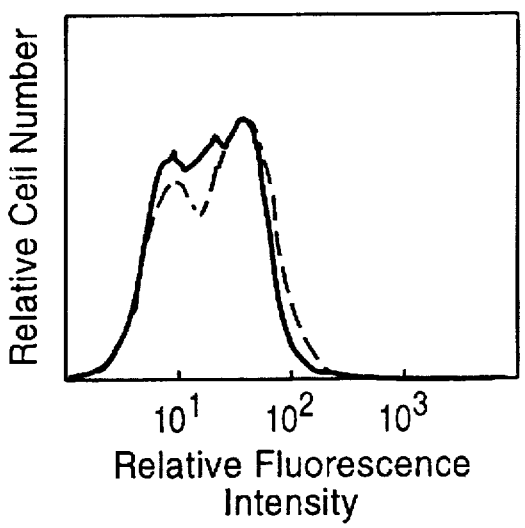
Figure 10C:
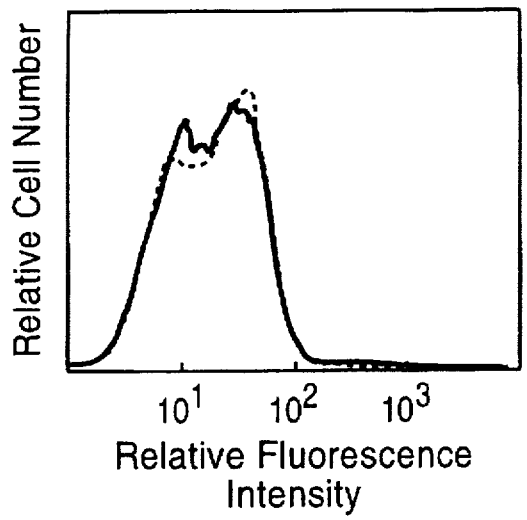
Figure 10D:
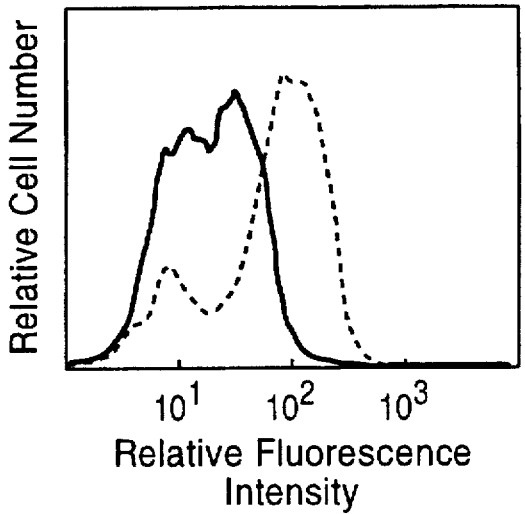
Figure 11A:
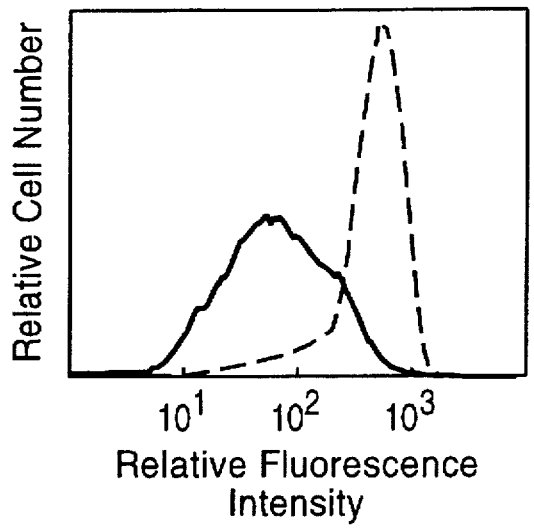
FIG. 11 shows the inhibition of FcεR (CD23) expression with (dashed line) or without (solid line) IL-4 in the presence of medium control (panel A), sIL-4R (panel B), anti-IL-4 antibody (panel C) or sIL-1R (panel D) as described in Example 17.
Figure 11B:
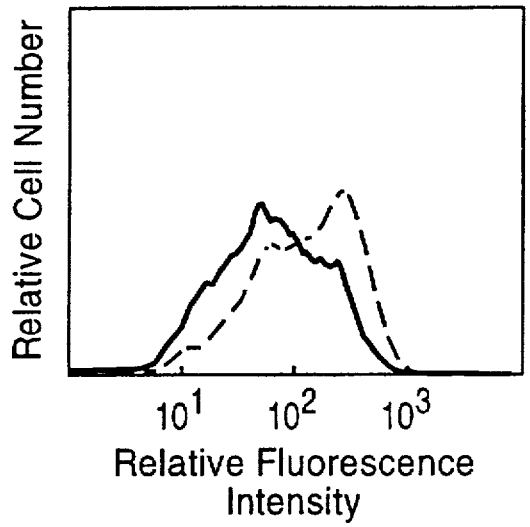
Figure 11C:
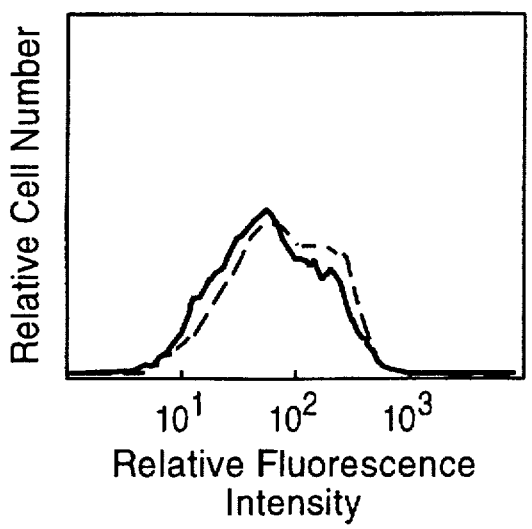
Figure 11D:
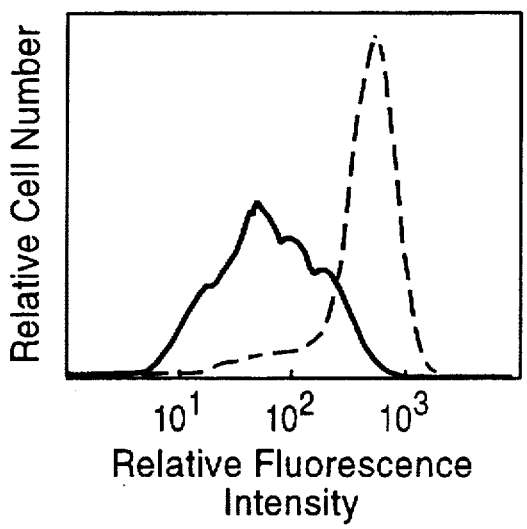

The effect of various doses of inhibitor on the inhibition of IgG1, IgG3 and IgE secretion is shown in FIG. 9. In this experiment, purified B cells ($1 \times 10^5$ cells/well) were grown in 96-well flat bottom plates in the presence of *Salmonella typhimurium* LPS (Difco Laboratories, Detroit, Mich.) and IL-4 (30 ng/ml for IgE; 3 ng/ml for IgG1 and IgG3) in the presence of three-fold dilutions of sIL-4R (□), sIL-1R (■) or 11B11 (●). Six days after initiation of culture, cells were pelleted by centrifugation at 750×g and culture supernatant fluids were harvested. The supernatants were analyzed for IgG1, IgG3 and IgE secretion using the isotype specific sandwich ELISA technique described above.

Figure 8A:
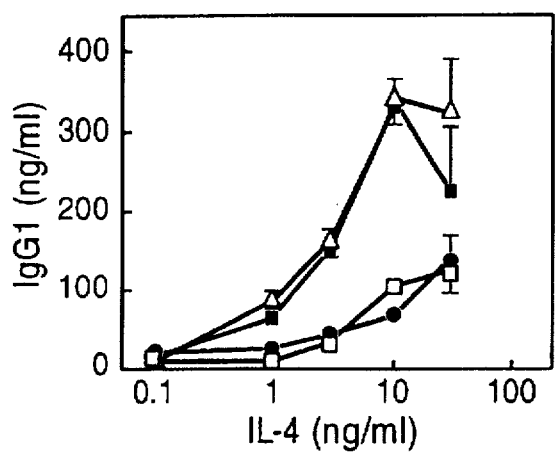
FIG. 8 shows the inhibition of immunoglobulin class switching with various doses of IL-4 and with sIL-4R (□), sIL-1R (■), or anti-IL-4 antibody (●) or medium control (△) as described in Example 16.
Figure 8B:
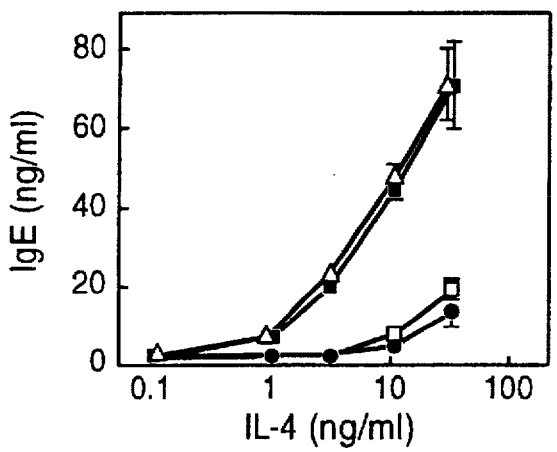
Figure 8C:
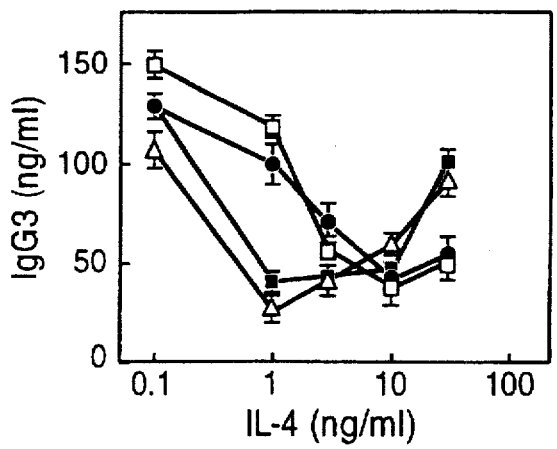

FIG. 8 (panels A and B) shows that IgG1 and IgE secretion from LPS treated B cells was induced by IL-4 and that these activities were inhibited by both the sIL-4R as well as 11B11. In contrast, panel C shows that IgG3 secretion was induced by LPS directly in the absence of exogenous cytokines. When IL-4 was present at concentrations of 10 ng/ml or less, LPS induced IgG3 secretion was ablated. sIL-4R blocked this inhibitory effect of IL-4, shifting the IL-4 dose response curve and effectively permitting induction of IgG3 secretion in the presence of otherwise inhibitory doses of IL-4.

FIG. 9 shows that the inhibition of IL-4 induced class switching by sIL-4R was dose dependent: with increasing concentrations of inhibitors, progressively lower levels of IgG1 and IgE and progressively higher levels of IgG3 were secreted. sIL-1R had no such effect, even at the higher concentrations (>1 ug/ml).

Example 17

Inhibition of IL-4 Induced Cell Surface Antigen Expression on B Cells In Vitro by sIL-4R IL-4 induces increased expression of various cell surface antigens on resting murine B cells. In order to determine the effect of sIL-4R on the inhibition of cell surface antigen expression, fluorescent-labeled antibodies to two specific cell surface antigens, MHC class II (Ia) antigens and FcεR (CD23), were used to measure the level of antigen expressed on B cells as follows.

Inhibition of MHC class II (Ia) Antigens. Purified B cells ($5 \times 10^5$ cells/ml) were cultured for 16 h in 24-well plates (Costar) with or without IL-4 (0.1 ng/ml) in the presence of sIL-4R, 11B11 or sIL-1R each at 500 ng/ml or medium control with or without inhibitors. Cells were washed and preincubated for 20 min on ice with the rat IgG2b anti-murine FcλR mAb 2.4G2 (Unkeless, et al., *J. Exp. Med.* 150:580, 1979) to block IgG Fc receptors. Fluorescinated mAbs (25-9-17, a murine IgG2a anti-murine I-A$^b$ antibody, described by Ozato et al., *J. Immunol.* 126:317, 1981; or control murine IgG1) were added directly and cells were incubated for 30 min at 4° C. and washed. The antibody diluent and wash solution was PBS/1% fetal calf serum/ 0.01% NaN$_3$. Stained cells were analyzed on a FACScan flow cytometer (Beckton-Dickinson, San Jose, Calif.) using a logarithmic fluorescence intensity scale.

FIG. 10 shows that in medium control (panel A) Ia expression in B cells is significantly greater in the presence of IL-4 (dashed line) than without IL-4 (solid line). Addition of sIL-4R (panel B) or 11B11 (panel C) at the onset of culture returned Ia expression to constitutive levels, whereas addition of sIL-1R (panel D) had no effect. The results shown in FIG. 10 are representative of 3 separate experiments.

Inhibition of FcεR (CD23). IL-4 also induces expression of CD23 on murine and human B cells. B cells were cultured without or without IL-4 in the presence of sIL-4R, 11B11, sIL-1R or medium control as described above. Cells were stained with FITC-labeled anti-CD23 antibody (B3B4, a rat IgG2a anti-murine FcεR [CD23], described by Rao et al., *J. Immunol.* 138:1845, 1987) as described above.

FIG. 11 shows that in medium control (panel A) CD23 expression in B cells is significantly greater in the presence of IL-4 (dashed line) than without IL-4 (solid line). Addition of sIL-4R (panel B) or 11B11 (panel C) returned cell surface CD23 expression to constitutive levels, whereas addition of sIL-1R (panel D) had no effect. As with Ia expression, the sIL-4R and 11B11 inhibitors did not diminish the constitutive expression of CD23, indicating that the inhibition was limited to the IL-4 dependent increase. The results shown in FIG. 10 are also representative of 3 separate experiments.

Examples 18 and 19 are experiments which show the effect of sIL-4R on the inhibition of IgE responses in vivo. Example 18 shows that sIL-4R inhibits an IgE response to a specific antigen. Example 19 shows that administration of sIL-4R in doses ranging from 1–25 ug twice daily on days −1, 0 and +1 do not inhibit an IgE response to a cocktail of anti-IgD antibodies.

Example 18

Inhibition of IL-4 Dependent Antigen-Specific IgE Response of B Cells by sIL-4R In Vivo Animals immunized with the hapten-carrier conjugate TNP-KLH (trinitrophenol-keyhole limpet hemocyanin) in alum generate a strong anti-TNP IgE antibody response. In order to determine the effect of sIL-4R administration on the IgE response, the following experiment was conducted.

Balb/c mice (3 mice/group, 7 groups) were immunized i.p. with 1 ug of TNP-KLH in alum on day 0. On day 21, the mice were boosted with the same amount of TNP-KLH, then bled 5 days later. Serum was then assayed by immunoglobulin isotype-specific ELISA for levels of both polyclonal and antigen-specific (TNP-specific) immunoglobulin. This secondary antibody response is characterized by, although not restricted to, the generation of a strong IgE response, most of which is anti-TNP specific.

On days −1, 0, and +1 of the secondary immunization, mice were given twice-daily injections of sIL-4R in total daily doses of 25, 5, and 1 ug/mouse. Thus, each mouse received a total of 75, 15, or 3 ug of sIL-4R over the three day treatment period. Serum was prepared from each animal, and analyzed for polyclonal and anti-TNP IgE concentrations.

Figure 12:
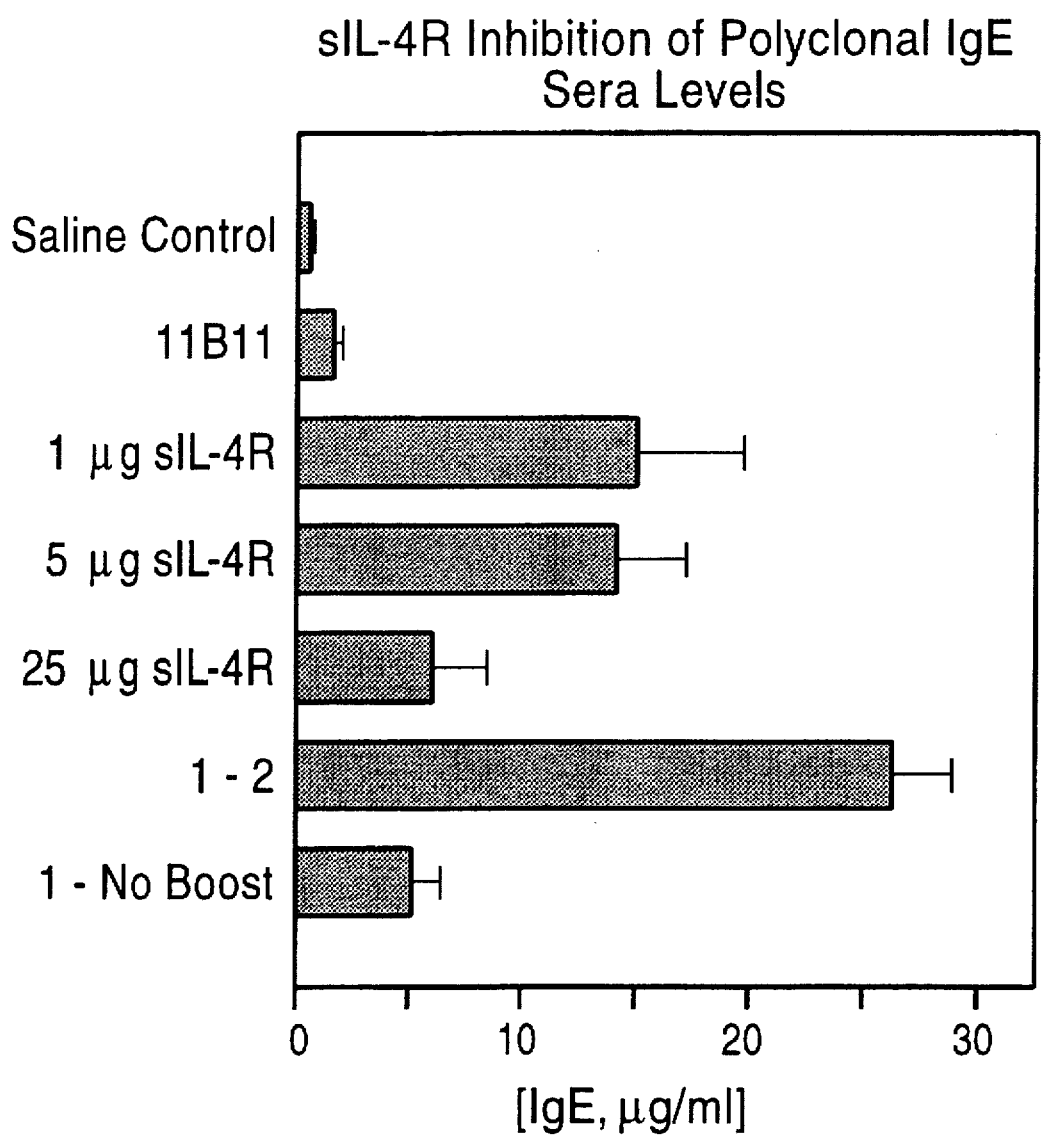
FIG. 12 shows the inhibition of antigen specific polyclonal IgE levels by sIL-4R as described in Example 18.

The results of these experiments, shown in FIG. 12, indicate that untreated mice (saline control), primary-immunized mice (1—no boost), and primed and boosted mice (1–2) displayed polyclonal IgE levels of approximately 1 ug/ml, 5 ug/ml, and 25 ug/ml, respectively. Treatment of boosted mice with 11B11 anti-IL-4 antibody lowered IgE levels to approximately 2 ug/ml. Treatment of boosted mice with sIL-4R lowered IgE levels significantly, with the highest concentration of sIL-4R (25 ug/hit) resulting in greater than 80% reduction in IgE. Lower doses of sIL-4R inhibited the polyclonal IgE response, although less dramatically. Thus, the sIL-4R acts as an inhibitor of an antigen-induced polyclonal IgE response.

Figure 13:
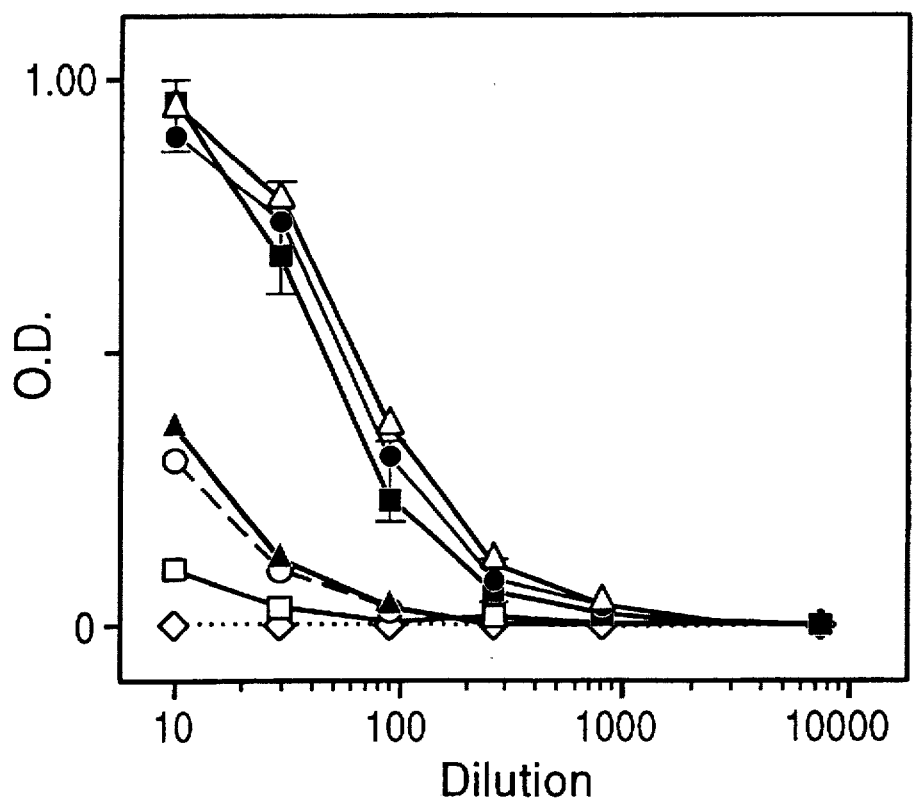
FIG. 13 shows the inhibition of antigen specific anti-TNP-KLH IgE levels by sIL-4R as described in Example 18.

FIG. 13 shows that priming of mice with TNP-KLH (1—no boost) resulted in a detectable anti-TNP response of the IgE isotype. Boosting with TNP-KLH caused a significant increase in the anti-TNP IgE titre. Treatment of primed and boosted mice with 11B11 at the time of secondary immunization diminished the antigen-specific IgE levels to less than levels seen in primed-only mice. The highest concentration of sIL-4R also dramatically decreased anti-TNP specific levels. Lower concentrations of sIL-4R had no discernible effect upon the secondary IgE response to TNP-KLH.

Example 19

In Vivo Inhibition of IL-4-Dependent Polyclonal IgE Response of B Cells by sIL-4R Animals immunized with a cocktail of monoclonal IgD antibodies specific for murine IgD (allotype specific) generate a strong polyclonal IgE antibody response. One likely mechanism of anti-IgD action involves crosslinking of surface immunoglobulin on B cells, internalization and processing of the anti-IgD, and presentation to helper T cells. The Ig-allotype specific T cells are thus triggered to provide signals (presumably cytokines) which induce immunoglobulin class switching and secretion by B cells.

Figure 14:
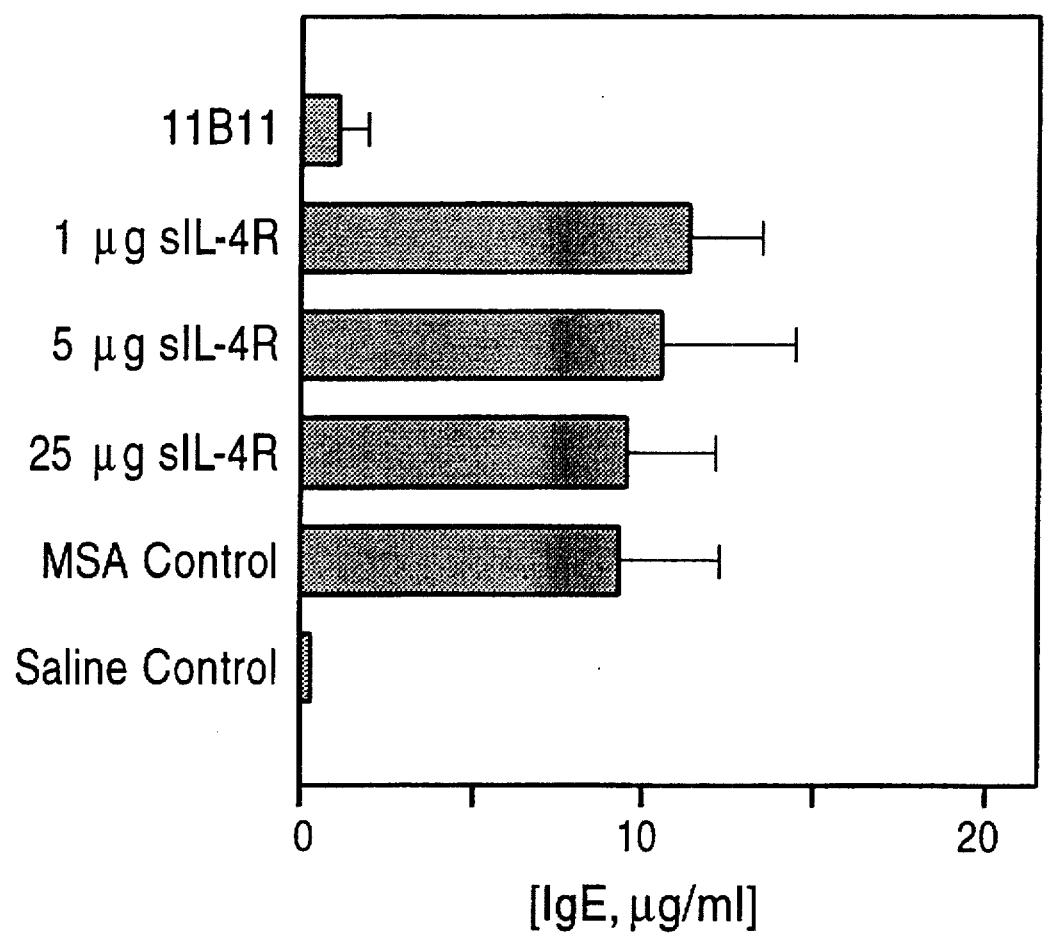
FIG. 14 shows that sIL-4R doses of 1, 5 or 25 ug on days −1, 0 and +1, as described in Example 19, do not significantly inhibit antigen specific anti-IgD IgE levels.

In order to determine the effect of sIL-4R administration on the IgD-induced polyclonal IgE response, the following experiment was conducted. BALB/c mice (3 mice/group) immunized i.v. with 800 ug of anti-IgD were treated twice daily with three different doses of sIL-4R (12.5, 2.5, or 0.5 ug/injection) on days −1, 0, and +1. Mice were bled on day 9 and serum IgE levels were determined. FIG. 14 shows that anti-IgD treatment (MSA control) caused large increases in levels of secreted IgE when compared with unimmunized controls (saline control). This effect was blocked by anti-IL-4 (11B11) administration, but not by any of the doses of sIL-4R. Anti-IgD treatment also caused large increases in IgG1, IgG2a, and IgG3. Whereas sIL-4R administration had no effect upon these isotypes, 11B11 administration resulted in increased IgG2a and IgG3 secretion.

The failure of sIL-4R to inhibit the IgE stimulatory effect of anti-IgD may be due to the fact that the inhibitor must be present for longer than one day after anti-IgD treatment, that the 11B11 antibody has a longer serum half-life than the sIL-4R, or that higher doses of sIL-4R are required.

Example 20

Figure 15:
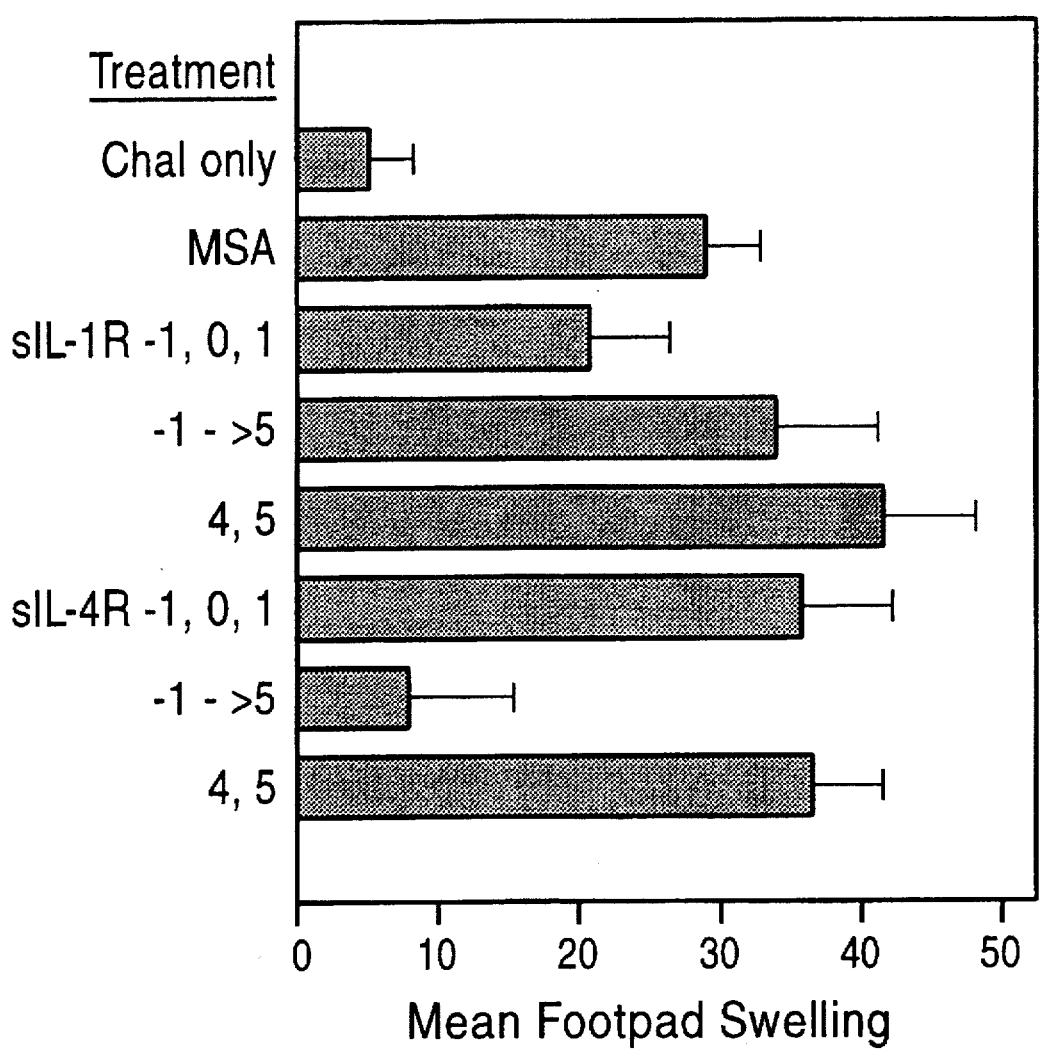
FIG. 15 shows the inhibition of contact hypersensitivity responses to DNFB with sIL-4R as described in Example 20.

Use of Soluble IL-4 Receptor to Inhibit Contact Hypersensitivity Responses to DNFB The effect of soluble IL-4 receptor (sIL-4R) and soluble IL-1 receptor (sIL-1R) on contact hypersensitivity (CHS) responses were evaluated in a murine system using 2,4-dinitrofluorobenzene (DNFB) as the contact sensitizer. Groups of female BALB/c mice (5 mice per group) were treated with either sIL-4R or sIL-1R on either days −1 through +1, days 4 and 5 or days −1 through 5 with 500 ng, b.i.d. via intraperitoneal injection. Control mice were treated with equivalent doses of the carrier solution containing mouse serum albumin (MSA). Epicutaneous sensitization with DNFB was performed by application of 25 ul of a solution of 0.5% DNFB in 4:1 mixture of acetone:olive oil to the shaved backs of mice on day 0. Negative control mice were not sensitized to DNFB. CHS responses were elicited by challenging all groups of mice on day 5 by application of 10 ul of the DNFB solution to the right rear footpads of the mice in each of the treatment groups. The extent of CHS induction was determined by measuring the difference in thickness (in units of $10^{-2}$ mm) between the challenged right and unchallenged left rear footpads (as measured with a dial micrometer) 24 hours later. FIG. 15 shows the results of these experiments. The data are presented as mean footpad swelling±SEM.

As shown in FIG. 15, mice treated with sIL-1R developed CHS responses that were not significantly different from control mice treated with MSA regardless of the treatment regimen used. Mice treated with sIL-4R on days −1 through 1 developed CHS responses that were not significantly different from the MSA control group. Although there appeared to be a slight increase in the CHS responses to DNFB induced in mice treated with sIL-4R on days 4 and 5, inspection of the data indicated that this was primarily due to the enhanced response of only one out of five of the mice in the group. No significant effect of treatment (either enhancement or inhibition) is observed if the response of this single mouse is considered to be an outlier and is not considered in the evaluation of the data (FIG. 15). However, mice treated with sIL-4R during the entire period (days −1 through 5) were significantly (p<0.001) inhibited relative to MSA-treated control mice, and not significantly different from mice which had not been sensitized, but only challenged, with DNFB. This data thus indicates that sIL-4R is effective in inhibiting contact hypersensitivity responses to DNFB.

Example 21

Figure 16:
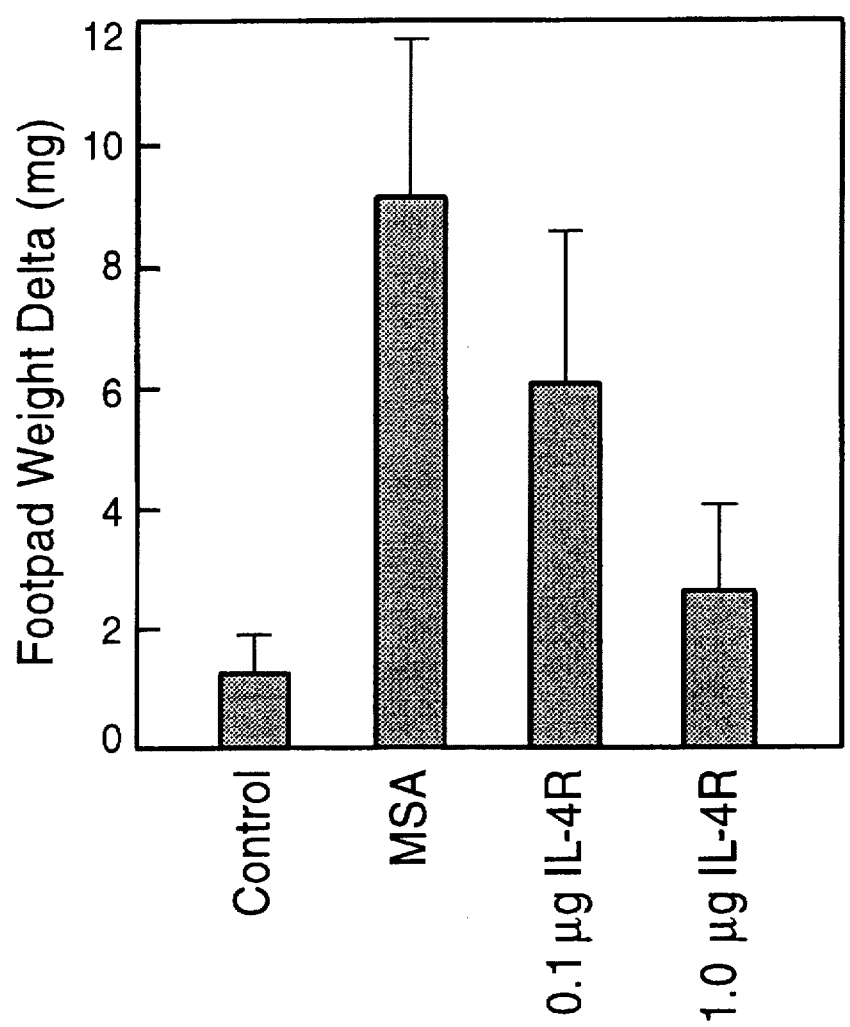
FIG. 16 shows the inhibition of delayed-type hypersensitivity responses to SRBC with sIL-4R as described in Example 21.

Use of Soluble IL-4 Receptor to Inhibit Delayed-Type Hypersensitivity Responses to SRBC The effect of soluble IL-4 receptor (sIL-4R) and soluble IL-1 receptor (sIL-1R) on delayed-type hypersensitivity (DTH) responses to sheep red blood cells (SRBC) were evaluated in a murine system as described by Kitamura, J. *Immunol. Meth.* 39:277, 1980. Three groups of female BALB/c mice (4 mice per group) were sensitized on day 0 by i.v. injection of $2\times10^5$ SRBC. A fourth group of negative control mice were not sensitized to SRBC. DTH responses were elicited in the sensitized mice by challenging the mice on day 4 with $1\times10^8$ SRBC via intracutaneous injection in the right rear footpads of the mice and 100 ul normal saline in the contralateral footpad as a control. The mice were treated with either 0.1 ug or 1.0 ug of sIL-4R in 100 ul MSA via intraperitoneal injection, on the day of challenge and the day of immunization. Control mice were treated with equivalent doses of the carrier solution (100 ul) containing mouse serum albumin (MSA). The fourth group of negative control mice not sensitized to SRBC were treated with 100 ul of MSA. The extent of the DTH response induced was determined by excising the footpads at the tarsus and measuring the difference in weight between SRBC challenged and saline challenged footpads. FIG. 16 shows the results of these experiments. The data are presented as mean footpad swelling±SEM.

As shown in FIG. 16, the DTH response was almost totally blocked by intraperitoneal injection with 1 ug sIL-4R on the day of challenge and the day of immunization. Treatment with 0.1 ug sIL-4R was less effective. Treatment with 0.2 ug or 2 ug of sIL-1R inhibited the response (not shown). These data thus indicate that sIL-4R is effective in inhibiting delayed-type hypersensitivity responses.

Example 22

Use of Soluble IL-4R to Suppress Immune Response to Alloantigen in vivo

Experiments were conducted to show that systemic administration of sIL-4R suppresses a localized, T cell-dependent, immune response to alloantigen presented by allogeneic cells. The response to allogeneic cells in vivo was quantified using the popliteal lymph node enlargement assay described by Twist et al., *Transplantation* 15:182, 1973, which is used as a measure of allograft transplant immunity (see Grebe et al., Adv. Immunol. 22:119, 1976). In this assay mice are injected in the footpad with irradiated, allogeneic spleen cells. The mice are then injected in the contralateral footpad with irradiated, syngeneic spleen cells. An alloreactive response (marked by proliferation of lymphocytes and inflammation) occurs in the footpad receiving the allogeneic cells, which can be measured by determining the increase in size and weight of the popliteal lymph node draining the site of antigen deposition relative to controls or by an increase in cellularity.

Specific pathogen free 8–12 week old BALB/c (H-$2^d$) and C57BL/6 (H-$2^b$) mice (Jackson Laboratory, Bar Harbor, Me.) were used in this experiment. 9 BALB/c mice were divided into 3 groups, each having 3 mice. Each group of mice received a different mode of treatment as indicated below in Tables B. On day 0 the left footpads of all mice were injected intracutaneously with $10^7$ irradiated (2500R), allogeneic spleen cells from C57BL/6 mice in 50 ul of RPMI-1640 (Gibco) as antigen and the right contralateral footpads of the same mice were injected with $10^7$ irradiated (2500R), syngeneic spleen cells from BALB/c mice. All doses of soluble murine IL-4 receptor (sIL-4R) were diluted in phosphate buffered saline (PBS). On days −1, 0 and +1 three mice were injected (intravenously on days −1 and 0, and subcutaneously on day +1) with 100 ng of purified smuIL-4R, three mice were injected intravenously with 1 ug of smuIL-4R, three mice were injected with 2 ug of smuIL-4R and three mice were injected with MSA (control).

Seven days after antigen administration, the mice were sacrificed and the popliteal lymph nodes (PLN) were removed from the right and left popliteal fossa by surgical dissection. Lymph nodes were weighed and the results expressed as the difference (Δ) in weight (mg) of the lymph node draining the site of allogeneic cell injection and the weight of the node draining the syngeneic cell injection site (Table B). The mean difference in weight of the lymph nodes from the sites of allogeneic and syngeneic spleen cells was approximately 2.5 mg for the mice treated with MSA, 1 mg for the mice treated with 100 ng of sIL-4R, and 0.5 mg for mice treated with 1 ug sIL-4R. No detectable difference in weight of lymph nodes was ascertainable for the mice treated with 2 ug sIL-4R. Lymph nodes draining the syngeneic cell injection site weighed approximately 1 mg, regardless of whether they were obtained from mice treated with MSA or smuIL-4R, and did not differ significantly in weight from nodes obtained from mice given no cell injection. Values for statistical significance were calculated using the two-tailed Student's t-test. Thus, IL-4R significantly ($p<0.1$ in all groups, using a two-tailed T test) suppressed the in vivo lymphoproliferative response in a dose dependent fashion relative to control mice.

TABLE B

Effect of smuIL-4R Administration on Proliferation of Lymph Node Cells

| Treatment Group | Weight (mg) of Lymph Node | | |
|---|---|---|---|
| | Allogeneic | Syngeneic | Δ |
| MSA | 3.9 ± 0.06 | 1.27 ± 0.07 | 2.63 ± 0.1 |
| 100 ng smuIL-4R | 2.3 ± 0.03 | 1.3 ± 0.03 | 1.0 ± 0.06 |
| 1 ug smuIL-4R | 2.1 ± 0.9 | 1.9 ± 0.3 | 0.23 ± 0.6 |
| 2 ug smuIL-4R | 1.6 ± 0.3 | 1.5 ± 0.1 | 0.0 ± 0.4 |

Table B shows that systemic administration of sIL-4R for 3 days beginning on day −1 relative to alloantigenic challenge resulted in a dramatic decrease in the size of lymph nodes, indicating that the lymphoproliferative response is inhibited. The effect was dose dependent and, in some cases, the response was virtually eliminated.

Example 23

Use of Soluble IL-4 Receptor to Suppress Allograft Rejection

Soluble murine IL-4 receptor also suppresses rejection of organ grafts in vivo. In order to demonstrate this, neonatal C57BL/6 (H-$2^b$) hearts were transplanted into the ear pinnae of adult BALB/c (H-$2^d$) recipients utilizing the method of Fulmer et al., Am. J. Anat. 113:273, 1963, modified as described by Trager et al., Transplantation 47:587, 1989, and Van Buren et al., Transplant. Proc. 15:2967, 1983. Survival of the transplanted hearts was assessed by visually inspecting the grafts for pulsatile activity. Pulsatile activity was determined by examining the ear-heart grafts of anesthetized recipients under a dissecting microscope with soft reflected light beginning on day 5 or 6 post transplant. The time of graft rejection was defined as the day after transplantation on which contractile activity ceases.

Recipient mice were divided into two groups, a primary treatment group and a secondary treatment group. The primary treatment group were not exposed to antigen from C57BL/6 mice previous to being treated, while the secondary treatment group had been exposed to antigen. All mice were transplanted on day 0 and injected with either smuIL-4R (1000 ng/day) plus MSA (mouse serum albumin, 100 ng) or with MSA alone on days 0 through 2, i.p. The results of this experiment are reported below in Table C. The probability (p value) that the survival time for the group treated with smuIL-4R differs by chance alone from the group treated with MSA is less than 0.04 when analyzed by the Student's t-test for the primary treatment group. The corresponding p values for secondary treatment group are not significant.

TABLE C

Effects of smuIL-4R Treatment on Nonvascularized Heterotopic Cardiac Allograft Survival

| Treatment Group | Survival Time (days) | Median Survival Time ± S.D. |
|---|---|---|
| Primary Treatment | | |
| MSA(100 ng) | 9, 10, 12, 14 | 11.3 ± 1.1 |
| smuIL-4R (100 ng) | 10, 10, 10, 12 | 10.5 ± 0.5 |
| smuIL-4R (1000 ng) | 12, 14, 14, 16, 17, 19 | 15.3 ± 1.0 |
| Secondary Treatment | | |
| MSA(100 ng) | 8, 8, 8 | 8 ± 0.0 |
| smuIL-4R (1000 ng) | 8, 10, 12 | 10 ± 1.2 |

Table C shows that heart allografts survived 9–14 days in individual control mice treated with MSA. When primary allograft recipients were given 3 daily injections of 1000 ng smuIL-4R, graft survival was prolonged. The median graft survival time in smuIL-4R treated mice (12–19 days) was approximately four days longer than the median graft survival time of identical grafts in control mice. A subtle increase in graft survival following secondary transplantation suggests that acute rejection episodes are influenced by smuIL-4R administration as well. This data is evidence of the therapeutic potential of soluble human IL-4 receptor in humans for the suppression of heart allograft rejection.

We claim:

1. A method for suppressing or inhibiting an IL-4-mediated immune or inflammatory response in a human, which comprises:

administering to a human an amount of a soluble IL-4 receptor (sIL-4R) and a suitable diluent or carrier effective to suppress or inhibit the IL-4-mediated immune or inflammatory response, wherein said sIL-4R is a soluble form of the IL-4R protein of FIGS. 4A–4C.

2. A method according to claim 1, wherein said immune or inflammatory response is an alloantigen induced IL-4-mediated immune or inflammatory response.

3. A method according to claim 1, wherein said IL-4-mediated immune or inflammatory response is an allergic or asthmatic reaction.

4. A method according to claim 1, wherein said immune or inflammatory response is a hypersensitivity reaction.

5. A method according to claim 4, wherein said hypersensitivity reaction is allergic rhinitis.

6. A method according to claim 4, wherein said hypersensitivity reaction is bronchial asthma.

7. A method according to claim 4, wherein said hypersensitivity reaction is atopic dermatitis.

8. A method according to claim 4, wherein said hypersensitivity reaction is a gastrointestinal food allergy.

9. A method according to claim 1, wherein said sIL-4R is expressed by a host cell containing a recombinant expression vector comprising nucleotides −75 to 621 of FIG. 4A.

10. A method according to claim 3, wherein said sIL-4R is expressed by a host cell containing a recombinant expression vector comprising nucleotides −75 to 621 of FIG. 4A.

11. A method according to claim 1, wherein said sIL-4R comprises an amino acid sequence selected from the group consisting of:

a) amino acids 1–207 of FIG. 4A; and b) amino acids 1–207 of FIG. 4A, with the proviso that the residue at position 50 is valine in place of isoleucine.

12. A method according to claim 3, wherein said sIL-4R comprises an amino acid sequence selected from the group consisting of:

a) amino acids 1–207 of FIG. 4A; and b) amino acids 1–207 of FIG. 4A, with the proviso that the residue at position 50 is valine in place of isoleucine.

13. A method of treating IL-4 mediated asthma in a human, comprising administering to a human afflicted with IL-4 mediated asthma an effective amount of an sIL-4R, wherein said sIL-4R is a soluble form of the IL-4R protein of FIGS. 4A–4C.

14. A method according to claim 13, wherein said sIL-4R has the amino acid sequence of amino acids 1–207 of FIG. 4A.

15. A method according to claim 13, wherein said sIL-4R is expressed by a host cell containing a recombinant expression vector comprising nucleotides −75 to 621 of FIG. 4A.

16. A method according to claim 13, wherein said sIL-4R comprises an amino acid sequence selected from the group consisting of:

a) amino acids 1–207 of FIG. 4A; and b) amino acids 1–207 of FIG. 4A, with the proviso that the residue at position 50 is valine in place of isoleucine.

17. A method for suppressing IL-4-mediated proliferation of lymphocytes in a human, which comprises:

administering to a human an amount of a soluble IL-4 receptor (sIL-4R) and a suitable diluent or carrier effective to suppress the IL-4-mediated proliferation of lymphocytes, wherein said sIL-4R is a soluble form of the IL-4R protein of FIGS. 4A–4C.

18. A method according to claim 17, wherein said sIL-4R is expressed by a host cell containing a recombinant expression vector comprising nucleotides −75 to 621 of FIG. 4A.

19. A method according to claim 17, wherein said sIL-4R comprises an amino acid sequence selected from the group consisting of:

a) amino acids 1–207 of FIG. 4A; and b) amino acids 1–207 of FIG. 4A, with the proviso that the residue at position 50 is valine in place of isoleucine.

20. A method of treating an IL-4 mediated IgE-induced condition in a human, comprising administering to a human afflicted with an IL-4 mediated IgE-induced condition an effective amount of an sIL-4R, wherein said sIL-4R is a soluble form of the IL-4R protein of FIGS. 4A–4C.

21. A method according to claim 20, wherein said IL-4-mediated IgE-induced condition is an allergy.

* * * * *